United States Patent
de los Reyes et al.

(10) Patent No.: US 8,157,999 B2
(45) Date of Patent: Apr. 17, 2012

(54) METHOD AND APPARATUS FOR THE FILTRATION OF BIOLOGICAL SOLUTIONS

(75) Inventors: Gaston de los Reyes, Somerville, MA (US); Leon Mir, Brookline, MA (US)

(73) Assignee: SPF Innovations, LLC, Somerville, MA (US)

(*) Notice: Subject to any disclaimer, the term of this patent is extended or adjusted under 35 U.S.C. 154(b) by 0 days.

(21) Appl. No.: 13/107,917

(22) Filed: May 15, 2011

(65) Prior Publication Data
US 2011/0215051 A1 Sep. 8, 2011

Related U.S. Application Data

(62) Division of application No. 12/685,192, filed on Jan. 11, 2010, now Pat. No. 7,967,987, which is a division of application No. 12/114,751, filed on May 3, 2008, now Pat. No. 7,682,511, which is a division of application No. 11/615,028, filed on Dec. 22, 2006, now Pat. No. 7,384,549.

(60) Provisional application No. 60/755,009, filed on Dec. 9, 2005, provisional application No. 60/754,813, filed on Dec. 29, 2005.

(51) Int. Cl.
*B01D 63/06* (2006.01)

(52) U.S. Cl. .......... 210/321.72; 96/8; 96/9; 210/321.75; 210/321.79; 210/321.8; 210/321.81

(58) Field of Classification Search ................... 96/4–10; 210/321.65, 321.71, 321.72, 321.74–321.81, 210/321.88–321.9, 335, 637, 641, 650, 652, 210/500.23
See application file for complete search history.

(56) References Cited

U.S. PATENT DOCUMENTS

| | | |
|---|---|---|
| 3,799,806 A | 3/1974 | Madsen |
| 3,933,646 A | 1/1976 | Kanamaru et al. |
| 3,965,012 A | 6/1976 | Eguchi et al. |
| 3,984,319 A | 10/1976 | Hubbard et al. |
| 4,105,547 A | 8/1978 | Sandblom |
| 4,200,533 A | 4/1980 | Gaddis et al. |
| 4,212,742 A | 7/1980 | Solomon et al. |
| 4,222,874 A | 9/1980 | Connelly |
| 4,235,723 A | 11/1980 | Bartlett, Jr. |
| RE30,632 E | 6/1981 | Breysse et al. |

(Continued)

FOREIGN PATENT DOCUMENTS
WO 98/50699 B2 11/1998
(Continued)

OTHER PUBLICATIONS

Cheryan, Ultrafiltration and Microfiltration Handbook,1998, pp. 316-317, Techmonic Publising company, inc., Lancaster, PA, U.S.A.

(Continued)

*Primary Examiner* — Joseph Drodge
(74) *Attorney, Agent, or Firm* — Barry Gaiman

(57) ABSTRACT

A system, method and device are disclosed for bio-processing a feed stream and providing a constant output by operating a continuous single-pass tangential-flow process. The single-pass process provides high conversion concentration while operating at relatively low feed flow rates, and the process can also be used to provide constant output diafiltration.

12 Claims, 31 Drawing Sheets

U.S. PATENT DOCUMENTS

| | | | |
|---|---|---|---|
| 4,312,755 A | 1/1982 | Hwang | |
| 4,343,705 A | 8/1982 | Legg | |
| 4,369,112 A | 1/1983 | Vincent et al. | |
| 4,430,218 A | 2/1984 | Perl et al. | |
| 4,478,506 A | 10/1984 | Miyoshi et al. | |
| 4,540,492 A | 9/1985 | Kessler | |
| RE32,089 E | 3/1986 | Blatt et al. | |
| 4,605,503 A | 8/1986 | Bilstad et al. | |
| 4,619,639 A | 10/1986 | Nose et al. | |
| 4,639,316 A | 1/1987 | Eldegheidy | |
| 4,643,902 A | 2/1987 | Lawhon et al. | |
| 4,668,399 A | 5/1987 | Duggins | |
| 4,716,044 A | 12/1987 | Thomas et al. | |
| 4,729,829 A | 3/1988 | Duggins | |
| 4,751,003 A | 6/1988 | Raehse et al. | |
| 4,755,297 A | 7/1988 | Nerad et al. | |
| 4,761,230 A | 8/1988 | Pacheco et al. | |
| 4,765,906 A | 8/1988 | Downing et al. | |
| 4,781,831 A * | 11/1988 | Goldsmith | 210/247 |
| 4,789,482 A | 12/1988 | DiLeo et al. | |
| 4,839,037 A | 6/1989 | Bertelsen et al. | |
| 4,855,058 A | 8/1989 | Holland et al. | |
| 4,879,098 A | 11/1989 | Oberhardt et al. | |
| 4,902,417 A | 2/1990 | Lien | |
| 4,952,751 A | 8/1990 | Blume et al. | |
| 4,973,404 A | 11/1990 | Weber et al. | |
| 5,009,781 A * | 4/1991 | Goldsmith | 210/247 |
| 5,108,601 A * | 4/1992 | Goldsmith | 210/247 |
| 5,147,542 A | 9/1992 | Proulx | |
| 5,200,090 A | 4/1993 | Ford et al. | |
| 5,248,418 A | 9/1993 | Munch | |
| 5,256,294 A | 10/1993 | van Reis | |
| 5,256,297 A | 10/1993 | Feimer et al. | |
| 5,258,122 A | 11/1993 | Ha et al. | |
| 5,366,630 A | 11/1994 | Chevallet | |
| 5,431,811 A | 7/1995 | Tusini et al. | |
| 5,490,937 A | 2/1996 | van Reis | |
| 5,520,816 A | 5/1996 | Kuepper | |
| 5,589,076 A | 12/1996 | Womack | |
| 5,593,580 A | 1/1997 | Kopf | |
| 5,597,486 A | 1/1997 | Lutz | |
| 5,628,909 A | 5/1997 | Bellhouse | |
| 5,641,332 A | 6/1997 | Faber et al. | |
| 5,647,990 A | 7/1997 | Vassarotti | |
| 5,654,025 A | 8/1997 | Raghunath et al. | |
| 5,660,728 A | 8/1997 | Saaski et al. | |
| 5,674,394 A | 10/1997 | Whitmore | |
| 5,674,395 A | 10/1997 | Stankowski et al. | |
| 5,683,916 A | 11/1997 | Goffe et al. | |
| 5,685,990 A | 11/1997 | Saugmann et al. | |
| 5,693,229 A | 12/1997 | Hartmann | |
| 5,762,789 A | 6/1998 | de los Reyes et al. | |
| 5,922,210 A | 7/1999 | Brody et al. | |
| 5,947,689 A | 9/1999 | Schick | |
| 5,958,244 A | 9/1999 | Hartmann | |
| 5,961,834 A | 10/1999 | Hjerten | |
| 5,985,151 A | 11/1999 | Ahmadi | |
| 6,054,051 A | 4/2000 | van Reis | |
| 6,068,775 A | 5/2000 | Custer et al. | |
| 6,077,435 A | 6/2000 | Beck et al. | |
| 6,077,436 A | 6/2000 | Rajnik et al. | |
| 6,110,699 A | 8/2000 | Ruiz et al. | |
| 6,126,833 A * | 10/2000 | Stobbe et al. | 210/650 |
| 6,197,191 B1 | 3/2001 | Wobben | |
| 6,197,194 B1 | 3/2001 | Whitmore | |
| 6,221,249 B1 | 4/2001 | van Reis | |
| 6,296,770 B1 | 10/2001 | Wilcox et al. | |
| 6,312,591 B1 | 11/2001 | Vassarotti et al. | |
| 6,342,157 B1 | 1/2002 | Hood, III | |
| 6,350,382 B1 | 2/2002 | Schick | |
| 6,357,601 B1 | 3/2002 | Bowers et al. | |
| 6,368,505 B1 | 4/2002 | Grummert et al. | |
| 6,375,847 B1 | 4/2002 | Hartmann | |
| 6,387,270 B1 | 5/2002 | van Reis | |
| 6,406,623 B2 | 6/2002 | Petersen et al. | |
| 6,478,969 B2 | 11/2002 | Brantley et al. | |
| 6,506,300 B2 | 1/2003 | Kuss et al. | |
| 6,536,605 B2 | 3/2003 | Rice et al. | |
| 6,555,006 B2 | 4/2003 | van Reis | |
| 6,561,172 B1 | 5/2003 | Chestnut et al. | |
| 6,579,494 B1 | 6/2003 | Chevallet et al. | |
| 6,592,763 B1 | 7/2003 | Benedictus et al. | |
| 6,607,669 B2 | 8/2003 | Schick | |
| 6,635,180 B2 | 10/2003 | Olapinski et al. | |
| 6,692,702 B1 | 2/2004 | Burshteyn et al. | |
| 6,692,968 B2 | 2/2004 | Burshteyn et al. | |
| 6,702,941 B1 | 3/2004 | Haq et al. | |
| 6,716,356 B2 | 4/2004 | Collins et al. | |
| 6,764,653 B2 | 7/2004 | Zermani | |
| 6,852,219 B2 | 2/2005 | Hammond | |
| 6,893,563 B2 | 5/2005 | Grummert | |
| 6,916,420 B2 | 7/2005 | Schmidt et al. | |
| 6,926,833 B2 | 8/2005 | van Reis | |
| 6,929,743 B2 | 8/2005 | Diel | |
| 6,932,907 B2 | 8/2005 | Haq et al. | |
| 7,048,855 B2 | 5/2006 | de la Cruz | |
| 7,141,171 B2 | 11/2006 | Lightfoot, Jr. | |
| 7,169,213 B2 * | 1/2007 | Liu et al. | 96/4 |
| 7,255,792 B2 | 8/2007 | Livington | |
| 7,384,549 B2 * | 6/2008 | de los Reyes et al. | 210/321.72 |
| 7,410,587 B2 | 8/2008 | Schick | |
| 7,967,987 B2 * | 6/2011 | de los Reyes et al. | 210/637 |
| 2002/0108907 A1 | 8/2002 | Van Reis | |
| 2003/0116487 A1 | 6/2003 | Petersen | |
| 2003/0146156 A1 | 8/2003 | Siwak et al. | |
| 2003/0178367 A1 | 9/2003 | van Reis | |
| 2003/0178368 A1 | 9/2003 | van Reis | |
| 2004/0129678 A1 | 7/2004 | Crowley et al. | |
| 2004/0188351 A1 | 9/2004 | Thiele et al. | |
| 2004/0221897 A1 | 11/2004 | Schubmehl et al. | |
| 2005/0035044 A1 | 2/2005 | Requate et al. | |
| 2005/0077229 A1 | 4/2005 | Ishii | |
| 2005/0126981 A1 | 6/2005 | Connors et al. | |
| 2005/0205489 A1 | 9/2005 | Siwak | |
| 2006/0027500 A1 | 2/2006 | Schick | |
| 2006/0043021 A1 | 3/2006 | Pesakovich et al. | |
| 2006/0060518 A1 | 3/2006 | Perreault | |
| 2006/0121555 A1 | 6/2006 | Lean et al. | |
| 2006/0249455 A1 | 11/2006 | Siwak et al. | |
| 2007/0029236 A1 | 2/2007 | Gaignet et al. | |
| 2007/0056894 A1 | 3/2007 | Connors, Jr. | |

FOREIGN PATENT DOCUMENTS

WO      03/033120 B3      4/2003

OTHER PUBLICATIONS

Zeman, Leos J. et al., Microfiltration and ultrafiltration: principles and applications, 1996, pp. 359-361, Marcel Dekker, Inc. New York, NY, U.S.A.

Ho, W. S. Winston et al., Membrane handbook, 1992, pp. 321-322, Van Nostrand Reinhold, New York, NY, U.S.A.

Flow Configuration, Jan. 23, 2001, pp. 1-8, Hydranautics Inc.

Search Report and Written Opinion of the USPTO as ISA mailed Jan. 10, 2008 (U.S. Appl. No. 11/615,028).

Thoma, Sonja et al., Pervaporation, ENVE 436, Dec. 4, 1998.

Knops, et al., The transversal flow microfiltration module Theory, design, realization and experiments, Journal of Membrane Science, 73 (1992) pp. 153-161 Elsevier Science Publishers B V, Amsterdam.

* cited by examiner

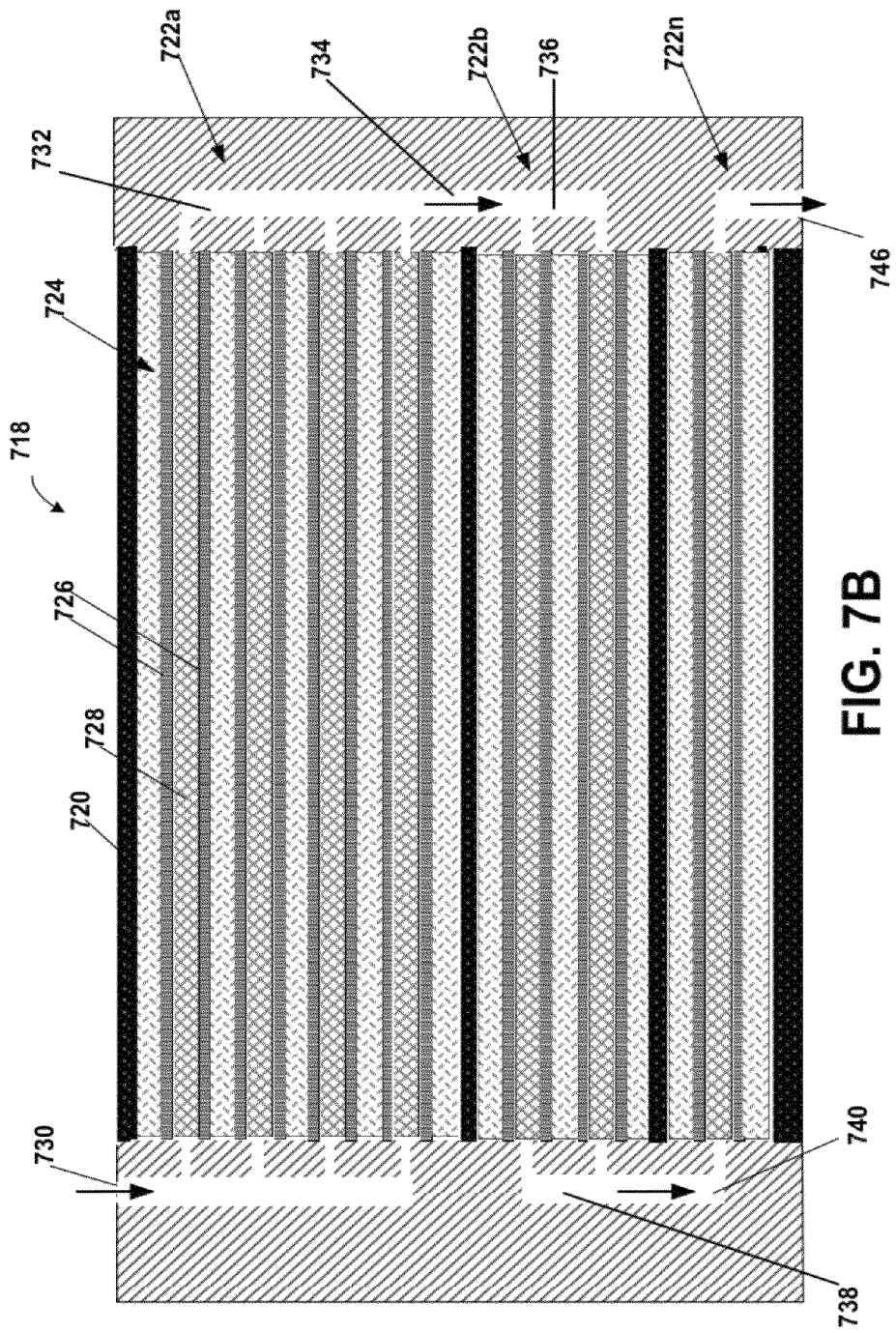

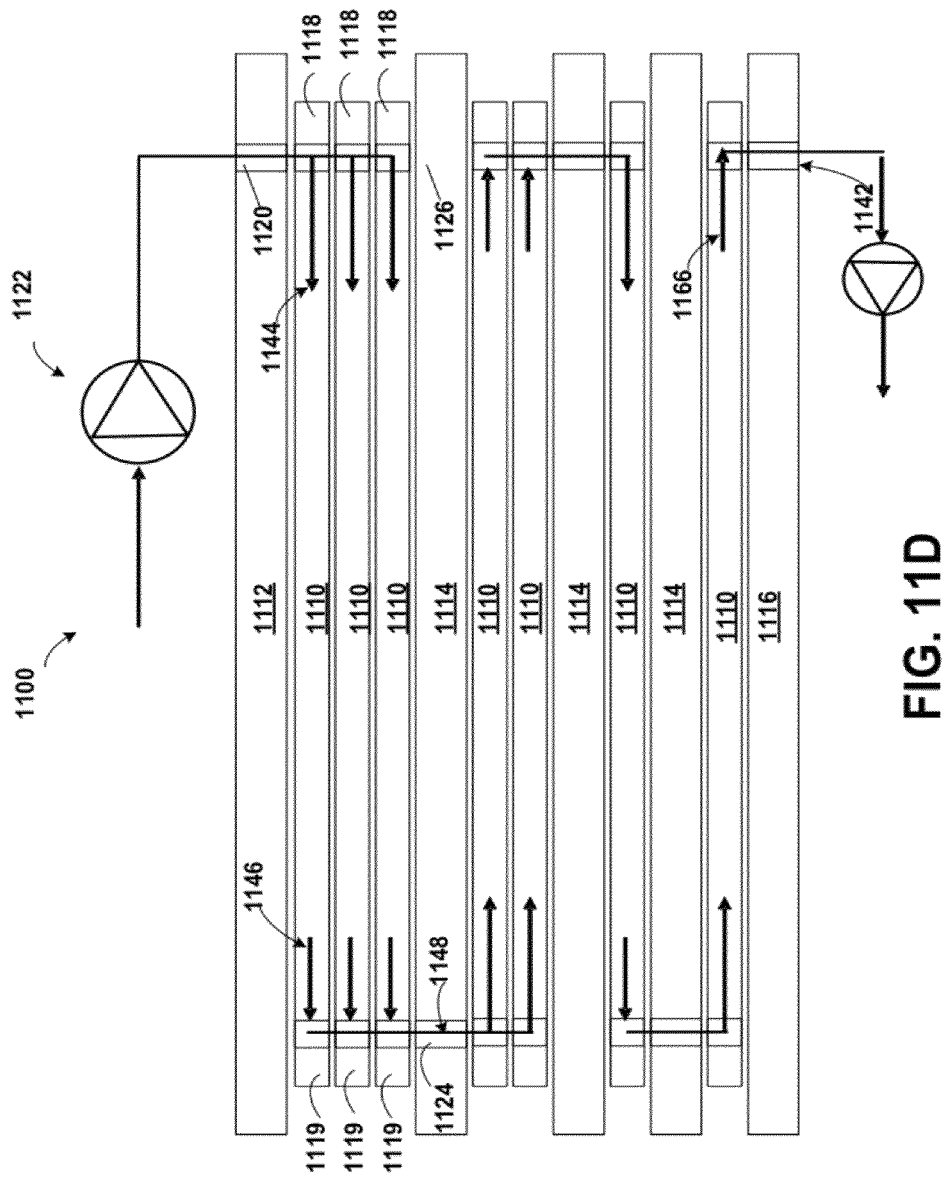

METHOD AND APPARATUS FOR THE FILTRATION OF BIOLOGICAL SOLUTIONS

RELATED APPLICATIONS

This is a division of pending application Ser. No. 12/685,192 filed Jan. 11, 2010 now U.S. Pat. No. 7,967,987, granted Jun. 28, 2011 which is a division of application Ser. No. 12/114,751 filed May 3, 2008 now U.S. Pat. No. 7,682,511, granted Mar. 23, 2010, which is a division of application Ser. No. 11/615,028 filed Dec. 22, 2006 now U.S. Pat. No. 7,384,549, granted Jun. 10, 2008, and which claims the benefit of U.S. Provisional Application No. 60/755,009, filed Dec. 29, 2005, and U.S. Provisional Application No. 60/754,813, filed Dec. 29, 2005, which applications are hereby incorporated herein by reference in their entireties.

STATEMENTS REGARDING FEDERALLY SPONSORED RESEARCH

Not applicable.

BACKGROUND OF THE INVENTION

1. Field of the Invention

The invention relates generally to a membrane separation systems, modules and methods and more specifically to single-pass tangential flow filtration operation for concentration and diafiltration of feed streams.

2. Description of the Related Art

Ultrafiltration (UF) and microfiltration (MF) membranes have become essential to the separation and purification in the manufacture of biomolecules. Biomolecular manufacturing, regardless of its scale, generally employs one or more steps using filtration. The attractiveness of these membrane separations rests on several features including, for example, high separation power, and simplicity, requiring only the application of pressure differentials between feed and permeate. This simple and reliable one-stage filtering of the sample into two fractions makes membrane separation a valuable approach to separation and purification.

In one class of membrane separations, the species of interest is that which is retained by the membrane, in which case the objective of the separation is typically to remove smaller contaminants, to concentrate the solution, or to affect a buffer exchange using diafiltration. In another class of membrane separations, the species of interest is that which permeates through the filter, and the objective is typically to remove larger contaminants. In MF, the retained species are generally particulates, organelles, bacteria or other microorganisms, while those that permeate are proteins, colloids, peptides, small molecules and ions. In UF the retained species are typically proteins and, in general, macromolecules, while those that permeate are peptides, ions and, in general, small molecules.

Permeation flux, also referred to as flux, is the flow of a solution through a filter. The ability to maintain a reasonably high flux is essential in the membrane separation filtration process. Low flux can result in long filtration times or require large filter assemblies, resulting in increased cost and large hold-up volumes retained in the modules and associated filter system equipment. The filtration process itself induces the creation of a highly concentrated layer of the retained species on the surface of the membrane, a phenomenon referred to as "concentration polarization," which reduces the flux from initial membrane conditions. In the absence of counter measures, the accumulation of retained particles or solutes on the surface of the membrane results in decreased flux and if not corrected the filtering process ceases to function efficiently. One conventional approach to overcoming the effects of concentration polarization in the practice of microfiltration and ultrafiltration is to operate the separation process in tangential flow filtration (TFF) mode.

TFF filters, modules and systems include devices having flow channels formed by membranes through which the feed stream flows tangentially to the surface of the membrane. The tangential flow induces a sweeping action that removes the retained species and prevents accumulation, thereby maintaining a high and stable flux. Because higher tangential velocities produce higher fluxes, the conventional practice of TFF requires the use of high velocities in the flow channels, which in turn result in very high feed rates. These high feed rates result in low conversion, typically less than 10% and often less than 5%. Low conversion means that the bulk of the feed stream exits the module as retentate in a first pass without being materially concentrated in the retained solutes. Since many UF separations require high concentration factors, as high as 99%, the retentate is typically recirculated back to the inlet of that module for further processing. Systems with recirculation loops are complicated by the requirement of additional piping, storage, heat exchangers, valves, sensors and control instrumentation. Additionally, these systems are operated in batch mode resulting in undesirable effects, including subjecting the feed solution to processing conditions for a long time, often several hours.

A conventional recirculation TFF process including a recirculation loop is shown in the process and instrument (P&I) diagram of FIG. 1. A TFF module 1 having a feed port 9, a retentate port 12 and a permeate port 10 receives a feed stream 7 from a batch tank 22 through a recirculation pump 6. Conventional TFF processes use commercially available TFF modules with flow channels of constant cross-section independent of where along the length of the channel the cross-section is measured. A feed compartment 2 is pressurized by the combined action of a pump 6 and backpressure valve 15 downstream of the retentate port 12. Pressure sensors 8 and 13 monitor the feed and retentate pressures, respectively. A permeate compartment 3 typically at or close to atmospheric pressure produces a permeate stream 11 from the permeate port 10 for further downstream processing or storage. A retentate stream 14 returns to the batch tank 22 through a heat exchanger 16. The heat exchanger 16 is often necessary to cool-down the retentate stream 14, which can heat up as a result of the pressure energy dissipated through, the backpressure valve 15. Although the temperature increase across the backpressure valve 15 is typically only about 1° F., the cumulative effect of recirculation can gradually increase the temperature of the batch by about 10 to 30° F. in the absence of an effective heat exchanger. To control the temperature of the batch, a temperature sensor 5 can be used to send a control signal 17 to a temperature controller 18, which in turn can automatically operate a flow control valve 19. The valve 19 controls the flow of cooling water 20 through the heat exchanger 16. Spent cooling water 21 returns to a central water chilling system (not shown). To control this process the flow rate of the feed pump 6 can be set according to the module supplier's recommendations followed by throttling retentate valve 15 until the desired feed pressure is obtained. Typically, these two process components need to be repeatedly adjusted to account for the increased viscosity of the feed stream 7 as the feed stream concentration increases as the separation progresses.

These conventional TFF processes possessing recirculation loops typically utilize flow rates greater than 4 liters/min/ m², and more typically less than 20 liters/min/m². These high flow rates are typically necessary to obtain practical fluxes and result in low single-pass conversion, f, typically between 5 and 10%. This in turn can require that the recirculation pump 6 be very large and the pipes carrying the feed stream 7 and the pipes carrying the retentate stream 14 have a flow capacity 10-20 times larger than those carrying the permeate stream 11. The need for a heat exchanger 16 and associated instrumentation, large recirculation pump 6, and large-capacity feed and retentate pipes makes conventional TFF systems with recirculation loops complex and costly. Additionally, the large capacity of the recirculation loop can result in a large system hold-up volume (i.e. a volume which remains in the system when processing is complete). The hold-up volume is a factor that typically leads to yield losses and that limits the maximum concentration factor achievable with such systems. Finally, because the process shown in FIG. 1 is inherently a batch process it takes several hours to process the volume in the feed stream 7 from the batch tank 22 before the desired output is ready for further processing. As a result, the solution being separated is exposed to the process for a long time, which can be a particularly undesirable feature for sensitive solutions. Furthermore, in these conventional processes the operating conditions are typically repeatedly adjusted as the process progresses to accommodate the changing volume of the batch and the increase in viscosity that can result from the increased concentration of the feed solution.

Several attempts have been made to improve conventional TFF module performance by modifying flow channel topology. U.S. Pat. No. 4,839,037, Bertelsen et al., discloses a spiral wound module with a tapered channel for the purpose of maintaining relatively constant velocities. U.S. Pat. No. 4,855,058, Holland et al., discloses maintaining flow velocities constant as material permeates, as applied to spiral wound membranes; using reverse osmosis, ultrafiltration and micro filtration membranes, and it describes the control of flow velocities by changing the channel height, the channel width and the channel length. U.S. Pat. No. 6,926,833, and related U.S. Pat. Nos. 5,256,294, 5,490,937, 6,054,051, 6,221,249, 6,387,270, 6,555,006, all issued to van Reis, and U.S. Pat. App. Pub. Nos. 2002/0108907 and 2003/0178367, van Reis, disclose improving the selectivity of ultrafiltration, including maintaining a constant TMP along the channel length by establishing a tangential flow of the fluid media over a second surface of the membrane and using converging channels having decreasing cross-sectional area. U.S. Pat. No. 6,312,591, Vassarotti, et al., discloses a filtration cell for carrying out a tangential flow filtration of a sample liquid feeding a flow of sample liquid tangentially over the membranes such that each channel is connected in parallel. Each channel includes in its longitudinal direction a number of subsequent channel sections separated by transitional zones and is constructed and arranged such that the main flow direction in subsequent sections changes abruptly in the transitional zones. The cell operates using a conventional TFF process and recirculates the sample liquid through a loop.

In conventional membrane processes such as reverse osmosis, gas permeation and ultrafiltration the desired separation can be enhanced or its costs reduced by staging. Systems with permeate staging devices process the permeate from a membrane module or a number of modules into another membrane stage or module, as the feed stream of this second stage. This is generally done to further remove impurities from the permeate. In some gas separation processes both the permeate and the retentate from a module or series of modules is further processed in one or more membrane stages. Typical of these processes is that described in U.S. Pat. No. 5,383,957, Barbe, et al., which discloses producing pure nitrogen from air.

Retentate staging is used in both ultrafiltration and reverse osmosis processes practiced on a large scale. In retentate staging the retentate from a stage serves as a feed to the next stage. Typical reverse osmosis processes include two to four retentate stages. The transition between stages is typically defined by a change in total flow cross-section of the flow channels in each stage. Typically each stage contains three to six spiral wound modules in a vessel. In reverse osmosis it is usual for the overall process to permeate between 50% and 75% of the feed. In order to maintain a fairly uniform flow rate through the membrane modules, the number of modules in each stage is reduced to compensate for the reduced feed rate to that stage. This configuration is known in the art as a "Christmas tree" design. In ultrafiltration systems, feed-and-bleed stages are used. In this design the effluent from each stage is partly recirculated to the feed of the stage by means of a recirculation pump. These conventional reverse osmosis multi-stage systems generally do not exceed four stages because of the requirement for additional external piping, instrumentation, controls and pumps. The efforts to apply retentate staging to UF systems based on the use feed-and-bleed systems have been generally unsuccessful for bio-processing applications. These retentate staged systems use circulation pumps in each stage, and while they are used extensively in the food industry for very large scale processes, these systems are too complex for use in the pharmaceutical industry and too difficult to validate for compliance with regulatory requirements. Retentate staged systems are used for water purification by reverse osmosis. Almost universally these systems use spiral wound modules. Because of the low permeability of RO membranes, thick flow channels are used without reducing fluxes materially. Because the fluxes are low very long stages are needed to achieve a reasonable concentration factor per stage.

Attempts have been made to develop single-pass TFF processes, however these attempts often require very high pressures, a multiplicity of very long modules in series and with the use of circulation pumps or re-pressurization pumps between stages. The modules usually have channels with relatively large channel dimensions. These conventional attempts result in large hold-up volumes and the additional complexity of intermediate pumps, tanks, valves, and instrumentation. In addition to concentration, staged filtration processes are used to carry out diafiltration. The most common form of diafiltration in continuous processes is the "parallel" diafiltration in which diafiltrate is added to each stage. Counter current diafiltration is sometimes used to reduce diafiltrate requirements. In counter current diafiltration fresh diafiltrate is added to the last stage and permeate of each stage serves as diafiltrate to the preceding stage. In both these forms of staged diafiltration process the total amount of diafiltrate required to achieve a given degree of permeating impurity removal decreases as the total membrane area is subdivided into a larger number of stages. The limit on the number of stages used is the increased cost as the total membrane area is divided into smaller stages. Conventional diafiltration systems generally use recirculation pumps with diafiltrate injected just before the pumps and do not operate as a single-pass TFF process.

Thus, the need still exists for a simple tangential flow process suited for the needs of pharmaceutical and biotech processes which is able to yield high reliable flux and high conversion without the need of recirculation loops and intermediate pumps, and that can be readily driven by the low-pressure differentials between the feed and the permeate. It would be desirable to operate a bio-processing separation in a single pass mode without a recirculation loop while providing a high conversion with a relatively low hold up volume. It would be further desirable to operate the separation without the requirement of a high capacity feed pump and associated system interconnections. Operation of a diafiltration process in a single pass mode would also be desirable. It would also be desirable to reduce bio-processing system cost by reducing some of the system complexity by using more versatile separation modules.

SUMMARY OF THE INVENTION

In accordance with one aspect of the present invention, a filtration system includes a plurality of stages, each stage having a plurality of channels providing at least one serial flow path. Each stage is in fluid communication with each adjacent stage preceding it and is in fluid communication with each adjacent stage that follows it. Each of the channels includes a filtration membrane and has a length, a membrane area, a void volume, a specific membrane area expressed as a ratio of the membrane area to the void volume, and a dimensionless length expressed as a product of the channel length and the specific membrane area. The dimensionless length of a stage is the sum of the dimensionless lengths of each channel in the longest serial flow path in the stage and the dimensionless length of the system is the sum of the dimensionless lengths of the stages. The specific membrane area of at least one channel in this system is greater than about 40 cm$^{-1}$ and the dimensionless length of the system is greater than about 2,000 and the dimensionless length of at least one of the of stages is less than about 6,000. Such a system, either internally or externally staged, is capable of operating efficiently in single pass mode and therefore eliminates the requirement of a recirculation loop and feed tank, and reduces feed pump size resulting in lower system costs, and a smaller equipment footprint. The system can also be scaled in a linear fashion to provide fluid stream processing over a wide range of feed volumes.

In accordance with a further aspect of the invention an internally staged filtration system includes a housing and stages within the housing. Each stage has a number of channels which are formed by a filtration membrane, and each stage is in fluid communication with each adjacent stage preceding it and is in fluid communication with each adjacent stage that follows it. At least two stages are fluidly coupled to form a serial flow path, and there is a change in a filtration property between the two stages in order to maintain separation performance. Such a system is able to yield high reliable flux and high conversion without the need of recirculation loops and intermediate pumps.

In accordance with still another aspect of the invention, a separation module for the filtration of liquids includes a housing, and at least one hollow fiber membrane which has a hydraulic permeability greater than about 2 lmh/psi. The hollow fiber is inside the housing and forms a flow channel. The flow channel has a membrane area, a void volume, a length, a specific membrane area expressed as a ratio of the membrane area to the void volume and a dimensionless length. The dimensionless length of the hollow fiber filtration membrane is greater than about 10,000, and the specific membrane area is greater than about 50 cm$^{-1}$. Such a device provides a simple, easily manufactured hollow fiber device capable of operating in single-pass TFF filtration (SPF) mode.

In accordance with still another aspect of the invention, a filter module for filtering a fluid mixture includes a housing, a membrane within the housing having a first surface, a feed spacer adjacent the first surface of the membrane. The spacer and the membrane form at least one channel, which is able to receive a tangential flow of fluid over the first surface of the membrane. The channel has a membrane area, a void volume, a length and a specific membrane area expressed as a ratio of the membrane area to the void volume and a dimensionless length expressed as a product of the channel length and the specific membrane area. The filter's specific membrane area is greater than about 40 cm$^{-1}$, the dimensionless length of the at least one channel is greater than about 3,000, and the at least one channel having a width generally decreasing in the direction of the tangential flow. This module is a more versatile separation module and reduces bio-processing system cost by reducing some of the system complexity. Such a module facilitates operation in a single pass mode without a recirculation loop while providing a high conversion with a relatively low hold up volume.

In one embodiment an internally staged filter module includes a housing, a plurality of stages within the housing. Each stage has channels with a filtration membrane and at least one manifold in fluid communication with the channels. Each stage is in fluid communication with each adjacent stage preceding it and is in fluid communication with each adjacent stage that follows it. At least one diafiltration distributor in the housing is in fluid communication with the manifold of selected stages and has an inlet for supplying a diafiltrate. Such a module allows a diafiltration process to operate with the advantages of operating in SPF mode.

In accordance with a further aspect of the invention a single pass filter system includes a top plate with a feed port stacked together with a set of cassettes. Each of the cassettes has a feed manifold, a retentate manifold, at least one permeate channel and at least one flow channel fluidly coupled to the feed manifold and to the retentate manifold, the flow channels of the plurality of cassettes fluidly coupled in parallel. A staging plate is stacked between the first set of cassettes and a second cassette which also has a feed manifold. The staging plate fluidly couples the retentate manifold of one of the cassettes of the first set of cassettes to the feed manifold of the second cassette and blocks the flow from the feed manifold of one of the cassettes of the first plurality of cassettes, thereby serializing the retentate flow. The second cassette has a retentate manifold. The system also includes a bottom plate in the stack with a retentate port in fluid communication with the flow channel of the second cassette. Such a system permits the use of conventional cassettes to be operated in an SPF mode by serializing at least one parallel flow path with another flow path and reduces the need for revalidation of the cassette and system performance.

In accordance with another aspect of the invention a method for filtering a liquid feed includes the steps of continuously supplying the feed stream into a membrane separation module at a specific feed flow rate of less than about 200 lmh and having at least one channel having specific membrane area greater than about 40 cm$^{-1}$ and operating the separation module in a single pass tangential flow filtration (SPF) mode. With such a technique used for concentration, highly concentrated output is available without waiting for the completion of a batch process. Other advantages of SPF operation include reduced complexity, shorter exposure time resulting in less protein damage, high concentration factors, lower hold-up volume, and reliable control of the process. SPF diafiltration provides similar advantages. In another aspect of the invention, the method further includes controlling the transmembrane pressure in the stages of a multi-stage systems and module independently of the feed pressure in the stages by using a permeate distributor to control permeate pressure.

In accordance with another aspect of the invention a method for processing a solute in a feed stream includes the steps of operating a plurality of stages having at least one stage comprising a plurality of substantially identical, long thin channels comprising the filtration membrane, in an SPF mode, maintaining separation performance in at least one of the plurality of stages by changing at least one property of at least one stage relative to a preceding stage, and continuously supplying the feed stream at a low specific feed flow rate. With such a technique, filtration membranes are efficiently used while achieving a high conversion factor and reducing system requirements, hold-up volume and processing time.

BRIEF DESCRIPTION OF THE DRAWINGS

The foregoing and other aspects, embodiments, objects, features and advantages of the present teachings can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the present teachings. The following drawings are illustrative of embodiments of the invention and are not meant to limit the scope of the invention as encompassed by the claims.

FIGS. 7B and 7C are schematic diagrams of internally-staged modules according to the invention wherein staging is accomplished by reducing the number of flow channels in each stage along the flow path;

FIG. 11D is a flow schematic of one embodiment of a single pass filtration concentration module in a 3-2-1-1 configuration according to the invention;

DETAILED DESCRIPTION OF THE INVENTION

Figure 1:
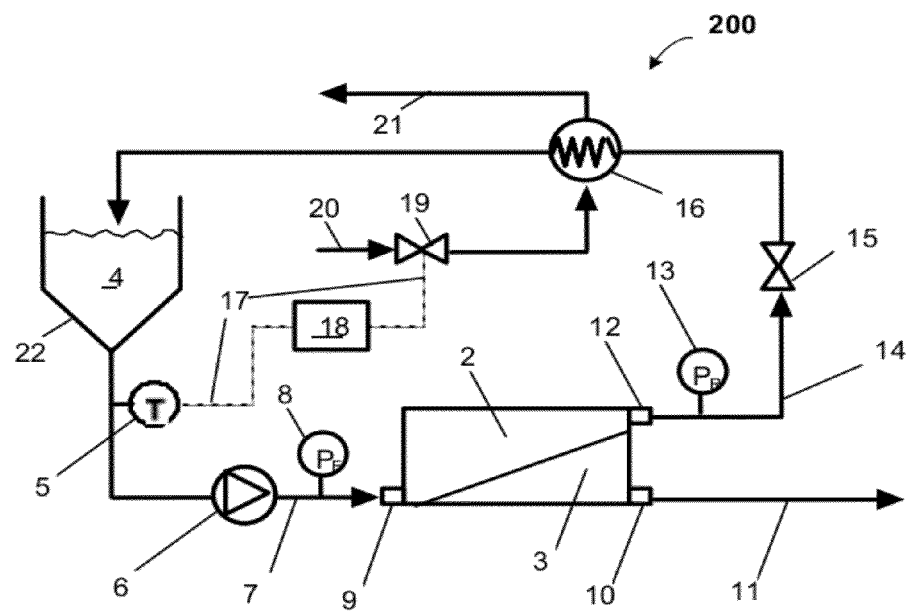
FIG. 1 shows a P&I diagram of prior art TFF process using a recirculation loop.

The present invention relates to the separation and purification of substances by membrane filtration, and more specifically, to SPF processes and devices. The devices and methods of the present invention utilize filtration membranes to separate components in a feed stream in a single pass at high conversion rates, in which a first driving force, transchannel pressure (TCP), is applied to drive liquid flow tangentially along the surface of the membrane, and a second independently controlled driving force, transmembrane pressure (TMP), drives the permeation through the membrane. As these are pressure-driven separations, the ultimate driving forces are pressure differentials. Suitable sources to induce the necessary pressure differentials include, but are not limited to, compressed gases, vacuum sources, pumps, and combinations thereof. The present invention matches these driving forces to devices having one or more of: a sufficiently large ratio of membrane area to flow channel void volume; ranges of channel lengths, permeate controls, and stage boundary transitions in multi-stage systems to allow effective operation in a single pass of the feed stream through the device. The use of thin channels results in high fluxes. The use of long flow paths in combination with selected driving forces provides for sufficiently long residence times in the flow channels resulting in high conversion and efficient diafiltration. The present invention depends, in part, upon the discovery that, when operating in a single pass mode using long, thin channels and low specific feed flow rates, the flux performance of the membrane is not degraded.

Before describing the invention, it may be helpful to an understanding thereof to set forth definitions of certain terms to be used herein. The term "separation" generally refers to the act of separating the feed sample into two streams, a permeate stream and a retentate stream. The terms "feed" and "feed stream" refer to the solution being fed to the filtration module for separation. The terms "permeate" and "permeate stream" refer to that portion of the feed that has permeated through the membrane. The terms "retentate" and "retentate stream" refer to the portion of the solution that has been retained by the membrane, and the retentate is the stream enriched in a retained species.

The expressions "flow channel" and "channel" are herein used synonymously to denote the separation channel comprising a membrane and in which the solution being separated is flowing in a tangential flow fashion. In certain embodiments, the separation channel comprises walls that are formed at least in part from an ultrafiltration membrane and in other embodiments from a microfiltration membrane. While channels can have an axis defined by the direction of the flow of liquid at any point of the channel, it should be understood that this does not require that the channels be straight. Channels can be straight, coiled, arranged in zigzag fashion, and in general can have any topology which supports tangential flow. Channels can be open, as in an example of channels formed by hollow fiber membranes, or they can have flow obstructions, as in the case, for example, of rectangular channels formed by flat-sheet membranes spaced apart by woven or non-woven spacers.

The expressions "single-pass conversion," "conversion per pass" and conversion are used herein to denote the fraction of the feed volume that permeates through the membrane in a single pass through the flow channels, expressed as a percentage of the feed stream volume. The terms "single pass concentration factor" and "concentration factor" as used herein describe the degree of concentration achieved for a specific species of interest as a result of a single pass through the flow channels. The concentration factor is a dimensionless quantity and expressed as the ratio of the concentration of the retained species in the retentate to that of the retained species in the feed. The concentration factor is also expressed as the volume of the feed divided by the volume of the retentate where the retained species is almost completely retained.

The expressions "liquid velocity" and "velocity" are herein used synonymously and refer to the velocity of the liquid within the channel in the direction of the flow path averaged across the channel cross-section. This definition recognizes that, in any flow channel, the velocity of the liquid is zero at any solid surface and increases away from a solid surface. The expressions "entrance velocity" and "inlet velocity" are herein used to refer to the velocity of the liquid at the entrance of a channel. The term "recovery" is used to denote the mass fraction of the species of interest recovered in the fraction of interest (permeate or retentate) expressed as a percentage of the mass contained in the feed stream. The terms "volumetric flux," "permeation flux" and "flux," designated by the symbol J, are used to describe the rate of permeation of the solution through the membrane, expressed herein with the units of liters per hour per $m^2$ of membrane area and abbreviated as "lmh"

The expressions "specific membrane area of the flow channel," "specific membrane area of the channel," and "specific membrane area," designated by the symbol $\sigma_c$, are herein used to denote the amount of membrane area contained in a channel per unit channel void volume. Expressed in units of $cm^{-1}$, $\sigma_c$ is defined by the following equation:

$$\sigma_c = \frac{\text{Membrane Area of Flow Channel [cm}^2\text{]}}{\text{Void Volume of Flow Channel [cm}^3\text{]}}. \tag{1}$$

In a multi-stage system, $\sigma_c$ for a stage is represented by the $\sigma_c$ of the channel having the largest $\sigma_c$ in that stage, and generally the channels in a stage have substantially equal values of $\sigma_c$.

The expressions "specific feed flow rate" and "specific feed rate" designated by the symbol F, are herein used synonymously to describe the flow rate of the feed stream divided by the membrane area of the module. F is expressed in units of lmh as follows:

$$F = \frac{\text{Module Feed Flow Rate}\left[\frac{\text{liters}}{\text{hr}}\right]}{\text{Module Membrane Area [m}^2\text{]}}. \tag{2}$$

The expressions "transmembrane pressure differential," "transmembrane pressure" and (TMP)" are herein used synonymously to describe the average pressure differential between the flow channel, and the permeate compartment, and given by:

$$TMP = P_F - P_P. \tag{3}$$

Where $P_F$=average of the pressure at the inlet and the outlet of the flow channel; and
$P_p$=pressure at the permeate compartment.

The expressions "transchannel pressure differential" and "transchannel pressure (TCP)" are herein used synonymously to describe the pressure differential between an inlet of a flow channel to an outlet of the flow channel, and is given by:

$$TCP = P_{inlet} - P_R; \tag{4}$$

where $P_{inlet}$=pressure at the inlet of the flow channel; and
$P_R$=pressure at the outlet of the flow channel.

The term "dimensionless length" is used herein to describe a product of channel length, L, and the specific membrane area, $\sigma_c$ from equation 1, of a channel, and is defined by the following equation:

$$\lambda = \sigma_c L \tag{5}$$

The dimensionless length of a stage in a multi-stage system is given by the sum of the dimensionless lengths of the channels in the longest serial path in the stage as follows:

$$\lambda_{stage} = \sum_{j=1}^{m} \sigma_{c,j} L_j; \quad (6)$$

where m is the number of channels in the longest serial path in the stage
$\sigma_{c,j}$ is the $\sigma_c$ of channel j in the longest serial path; and
$L_j$ is the length of the $j^{th}$ channel.
The dimensionless length of a system in a multi-stage system having n stages is given by the sum of the dimensionless length of the stages of the system as follows:

$$\lambda_{system} = \sum_{i=1}^{n} \lambda_{stage,i}; \quad (7)$$

where n is the number of stages in the system; and
$\lambda_{stage,i}$ is the $\lambda$ for the $i^{th}$ stage.

The term "ultrafiltration membranes" and "UF membranes" are used herein to refer to membranes that have pore sizes in the range between about 1 nanometer to about 100 nanometers. The term "microfiltration membranes" and "MF membranes" are used herein to refer to membranes that have pore sizes in the range between about 0.1 micrometers to about 10 micrometers. UF membranes are useful, for example, for the separation of polymeric molecules from water and other low molecular weight solutes. Molecules that are too large to penetrate these pores are retained while water, dissolved salts and small molecules can pass through these pores. The retention behavior of a membrane forms the basis for characterizing UF membranes, known as the "molecular weight cut off" of the membranes, expressed in units of Daltons, and abbreviated as MWCO. In various embodiments, the present invention utilizes ultrafiltration membranes having MWCO ratings in the range from about 1,000 Daltons to several million Daltons.

It is understood, that an SPF or conventional TFF filtering process is started at a specific feed rate equal to zero and operated for a period of time at specific feed flow rates at which SPF is practiced before settling at an operational specific feed rate. The conventional TFF processes operate at specific feed flow rates higher than SPF processes (e.g., rates time-averaged over a time interval of several minutes). It is also understood that there may be minor pressure variations that would cause an SPF process to operate at an instantaneous or short term specific feed flow rate higher than the desired specific feed flow rate. The term "continuously supplying the feed stream," as used herein, is understood to mean supplying the feed stream at an average specific feed flow rate, for example averaged over one minute to several minutes.

Figure 2:
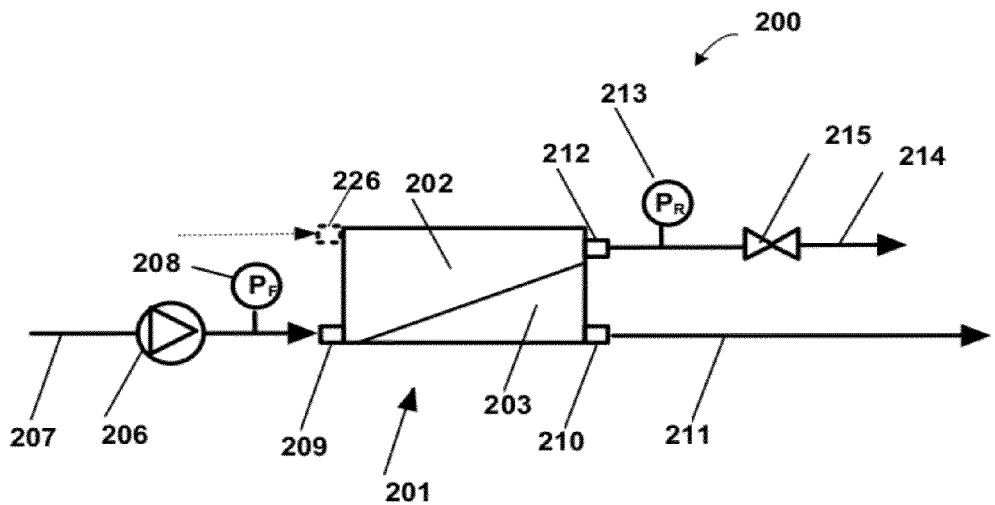
FIG. 2 shows a P&I diagram of an SPF process according to the invention.

Now referring to FIG. 2, a P&I diagram depicts an exemplary system 200 operating as an SPF process according to the invention. The system 200 includes an SPF membrane separation module 201 including a channel 202 which in one embodiment has specific membrane area greater than about 40 cm$^{-1}$. The channel 202 is fluidly coupled to a feed port 209 and a retentate port 212. The separation module 201 further includes a permeate compartment 203 fluidly coupled to a permeate outlet port 210. In one embodiment the permeate compartment 203 is at least partially formed by a filtration membrane and is disposed adjacent the channel 202, and except for the permeate outlet port 210 is otherwise sealed. The system 200 further includes a pressure device 206 feeding a feed stream 207 into the module 201, a feed pressure sensor 208 and a retentate pressure sensor 213 to monitor the feed pressure and retentate pressure, respectively. The system 200 includes a backpressure valve 215 (also referred to as retentate valve 215) is fluidly coupled to retentate port 212 and is located downstream from the retentate port 212. In an alternative embodiment a permeate distributor (as described below in conjunction with FIG. 21) can be used to further control the SPF process. In another embodiment, system 200 includes an optional diafiltrate stream supplied through optional diafiltration port 226 enabling an SPF diafiltration process (as described below in conjunction with FIGS. 13A, 16A, 18A, 19A and 20).

In operation, the pressure device 206, in one embodiment a feed pump, controls the process in conjunction with the back pressure valve 215. In contrast to conventional separation modules which operate at specific feed flow rates typically greater than 300 lmh, the pressure device 206 feeds fluid at a rate such that the SPF process operates at specific feed flow rates of less than about 200 lmh and in other embodiments at specific feed flow rates of less that about 100 lmh In one embodiment, the feed stream is continuously supplied at an inlet pressure greater than about 60 psi whereas conventional TTF processes are generally operated at much lower inlet pressures. It is understood, that upon startup a conventional system temporarily operates at a low specific feed flow rate beginning at about zero. The pressure device 206 continuously supplies the feed at low specific feed flow rates. The channel 202 is pressurized, for example, by the combined action of pressure device 206 and the backpressure valve 215. Pressure sensors 208 and 213 monitor the feed and retentate pressures, respectively. In various embodiments, the permeate compartment 203 is at or close to atmospheric pressure, and the permeate stream 211 is directed through the permeate port 210 for further downstream processing or storage, and in other embodiments, the pressure in the permeate compartment 203 may be elevated by means of suitable hydraulic resistors coupled to the permeate stream (not shown). The retentate stream 214 is directed through the retentate port 212 for further downstream processing or storage.

In certain embodiments, high conversion in a single pass is obtained by employing low specific feed rates. In general, when operating separation modules and systems in an SPF mode, the conversion is determined by selecting any two of the following parameters: the feed flow rate, the retentate flow rate, the permeate flow rate, specific feed rate, TMP and TCP. Selecting and controlling two of these parameters determines the values of the remaining parameters. In these embodiments, one direct method for controlling the process is to measure the conversion and adjust either the feed or retentate flow rates in an iterative manner. Referring again to FIG. 2, in one embodiment the following steps are used with a feed pump as the pressure device 206 and the retentate valve 215 to control the SPF process:

1. the permeation process is started by setting the flow rate of the pressure device 206 to obtain a suitably low specific feed rate, F;
2. retentate valve 215 is throttled until the desired TMP is obtained;
3. the conversion f is measured (by comparing flow rates or concentrations by means of suitable sensors) after the process is allowed to equilibrate;

4. if the conversion is not close enough to the desired value, then the flow rate through the pressure device 206 and the retentate valve 215 are adjusted, up or down as follows:
   a. if the conversion f is too high, the retentate valve 215 is opened slightly, then the flow rate of pressure device 206 is gradually increased until the feed pressure returns to its initial value; these two adjustments lead to a small increase of TCP and in turn a small increase of specific feed rate, F;
   b. if the conversion f is too low, the flow rate of the pressure device 206 is decreased by a small amount, then the retentate valve 215 is closed slightly until the feed pressure returns to its initial value; these two adjustments lead to a small decrease of TCP and in turn a small decrease of specific feed rate F; and
5. steps 3 and 4 are repeated until the desired conversion f is obtained.

Additionally, an SPF process can be operated by setting the conversion to a predetermined factor by controlling the ratio of the feed stream flow rate to the retentate stream flow rate. In one embodiment, the ratio of the feed stream flow rate to the retentate stream flow rate is provided by coupling the pumps in the feed and retentate streams. In various embodiments, a specific feed rate lower than about 200 lmh is used to obtain conversions exceeding about 50%, and in other embodiments a specific feed rate lower than about 100 lmh is used.

The pressure device 206 provides the driving forces to induce pressure differentials to affect the separation. SPF separations generally include two distinct pressure differentials: a first pressure differential to drive liquid flow tangentially along the surface of the membrane, the TCP, and a second pressure differential to drive the permeation across the membrane, the TMP. Pressure devices 206 for inducing the necessary pressure differentials include, but are not limited to, compressed gases, vacuum sources, pumps and combinations thereof. For example, a compressed gas can be used to drive the feed solution, the same compressed gas at a lower pressure connected to the retentate receptacle can be used to control the TCP, while the permeate is kept at atmospheric pressure. This combination of two pressure sources can be used to provide the desired TCP and TMP. Alternatively, a vacuum source may be used to drive the SPF separation process by connecting a vacuum source, controlled at different vacuum levels, to the permeate and retentate receptacles while the feed is kept at atmospheric pressure. This combination of two vacuum sources can also be used to provide the desired TCP and TMP. In some cases it may be convenient to use both pressure and vacuum sources. There are a wide variety of vacuum and pressure sources well known to those skilled in the art. For example, a vacuum source can be a liquid driven aspirator or venturi, a central vacuum supply of the type commonly found in laboratories, a dedicated vacuum pump, or combinations thereof. A detailed list of means and devices for generating vacuums is given in Perry's Chemical Engineering Handbook, $6^{th}$ edition, McGraw-Hill, 1984, at pp. 6-32 to 6-37. Suitable pressure sources include, for example, compressed gases from a cylinder with conventional means for regulating the applied pressure, using pressurized gas from a central source commonly available in laboratories, using a dedicated compressor from among the types described, for example, in Section 6 of Perry's Chemical Engineering Handbook. Another suitable pressure device is a liquid pump. A wide variety of pumps are suitable for providing driving forces in the methods and devices of the present invention. Examples include peristaltic, syringe, centrifugal, piston, rotary lobe, and gear pumps. A detailed list of pumps is given in Perry's Chemical Engineering Handbook, $6^{th}$ edition, McGraw-Hill, 1984, at pp. 6-4 to 6-17.

The separation module 201 comprises a filtration membrane including, but limited to, one of a tubular, sheet and monolithic structure. The separation module 201 can use filtration membranes fabricated into any of several topologies. Hollow fiber membranes are generally a tubular membrane, with an inner diameter of typically between about 0.1 and 2.0 millimeters whose inner or outer surface is the separating membrane. In various applications, the feed stream to be processed flows through the inside of the hollow fiber membrane, also referred to as the "lumen," and the permeate leaves on the outside of the fibers. Sheet membranes can be made in various forms and typically are laminated to some sort of cloth support. Two sheets of membrane separated by a highly permeable net-like structure, or spacer, form the flow channel. A wide variety of sheet membranes can be used in various embodiments of the present invention, including, but not limited to, non-planar sheets and monolithic membranes. For example, membranes with undulating, dimpled or corrugated surfaces are examples of non-planar sheet membranes. It is possible to implement the SPF process using various separation modules and housings including, but not limited to, a hollow fiber cartridge, a plate-and-frame assembly, a cassette and a spiral wound module.

In certain embodiments of the present invention, system 200 is used to concentrate a retained species. In one embodiment, the concentration process removes solvent from the feed stream as well as any other solute that permeates through the membrane in a single pass. The result is the concentration of those solutes that are retained by the membranes. Additionally, this concentration process purifies the retained species by the substantial removal of those species that permeate through the membrane. In other embodiments of the present invention, system 200 is used to perform a diafiltration processes in a single pass. In these diafiltration embodiments, the solution that permeates through the membrane is replaced with another solution (also referred to as a diafiltrate or buffer) in order to change the composition of the solution in which the retained solutes are dissolved. The addition of the diafiltrate can be performed, for example, substantially simultaneously with concentration, or sequentially in a series of alternating concentration and diafiltration steps, or by a combination of the two processes.

The specific membrane area of the channel 202, $\sigma_c$, is in some embodiments greater than about 40 $cm^{-1}$, in other embodiments greater than about 50 $cm^{-1}$, and in other embodiments greater than about 100 $cm^{-1}$. The specific feed rate, F, is in other embodiments less than about 200 lmh, and in other embodiments less than about 100 lmh The dimensionless length, $\lambda$, is in some embodiments greater than about 2,000, in other embodiments greater than about 3,000, and in yet other embodiments greater than about 4,000. The operation of system 200 in SPF mode and continuously supplying the feed at a specific feed flow rate of less than about 200 lmh overcomes or eliminates one or more of the drawbacks associated with conventional TFF requiring recirculating streams. As compared to a conventional TFF separation modules and processes, the SPF process is enabled by low feed rates and long and thin channels as listed in Table 1, resulting in higher conversion in a single-pass. As described below in conjunction with FIG. 7, the process of FIG. 2 can also be used in a multi-stage system provided either in an internally or externally staged configuration to provide similar advantages. SPF systems whether staged (internally or externally) or unstaged, and regardless of the means used to drive the filtration process in various embodiments have one or more of the following advantages over conventional TFF systems:

1. high conversion in a single-pass, obtaining conversions greater than about 50%, in other embodiments conversions greater than about 75%, and in yet other embodiments conversions greater than about 90%;
2. simple, easier to control processes with lower hold-up volume; and
3. average residence times greater than about 2 seconds in some cassette embodiments and greater than about 20 seconds for certain hollow fiber embodiments, where the average residence time is equal to the void volume of the flow channels divided by the average flow rate in the channel (the approximate average of the feed flow rate into the module and retentate flow rate out of the module).

TABLE 1

Conventional TFF Operation vs. SPF Operation

|  | TFF | SPF |
|---|---|---|
| Specific Feed Rate F | 300~1,500 lmh | <200 lmh |
| Specific Membrane Area | <75 cm$^{-1}$ | >40 cm$^{-1}$ |
| Process | Batch process requiring recirculation loops | Single-pass process |
| Conversion Per Pass f | <15% | >50% |

It is understood that a process using SPF devices and operating parameters could be operated in a batch mode. In these embodiments, the retentate stream from an SPF module is recirculated back to the feed. Such a process provides the advantage of smaller circulation rates and therefore requires smaller hydraulic components, pumps and piping.

Figure 3:
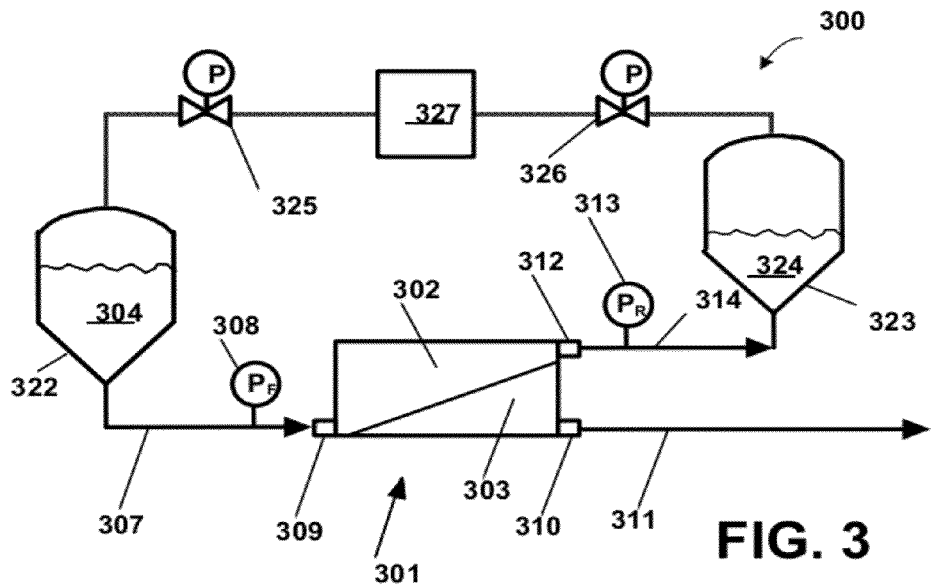
FIG. 3 shows a P&I diagram of a an SPF similar to the process of FIG. 2 in which two pressurized tanks drive and control the process.

Referring to FIG. 3, a process and instrument diagram of a SPF process and system 300 similar to system 200 of FIG. 2, includes a SPF membrane separation module 301 having pressurized tanks, feed tank 322 and retentate tank 323 in place of the pressure device 206 and the retentate valve 215 of FIG. 2, respectively. The system 300 further includes pressure regulators 325 and 326, connected to a compressed gas source 327. It is noted that the SPF system embodiment of FIG. 3 does not include any pumps.

In operation, the two tanks 322, 323 are maintained at the desired feed and retentate pressures by means of the pressure regulators 325 and 326. The following steps are used with the pressurized feed tank 322 and retentate tank 323 to operate the filtration process:

1. the permeation process is started by setting the feed pressure and the retentate pressure to initial values with pressure regulators 325 and 326, respectively, thereby obtaining an initial TCP, and a suitably low specific feed rate, F;
2. the conversion f is measured after the process is allowed to equilibrate;
3. if the conversion is not close enough to the desired value, then TCP is adjusted up or down by adjusting pressure regulator 326 as follows:
    a. if the conversion f is too high, reduce retentate pressure 313 slightly, which leads to a small increase of TCP and in turn a small increase of specific feed rate, F;
    b. if the conversion f is too low, increase retentate pressure 313 slightly, which leads to a small decrease of TCP and in turn a small decrease of specific feed rate, F;
4. steps 2 and 3 are repeated until the desired conversion is obtained.

Figure 4A:
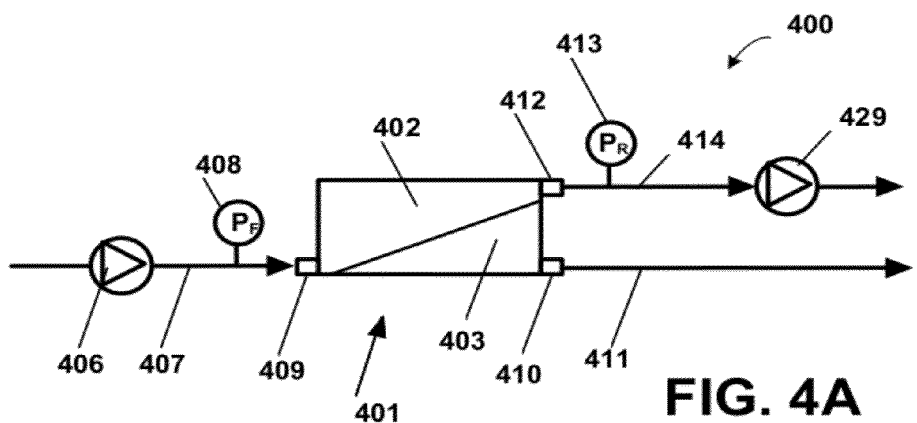
FIGS. 4A and 4B show P&I diagrams of an SPF processes according to various embodiments of the present invention in which two pumps are used to drive and control the process.
Figure 4B:
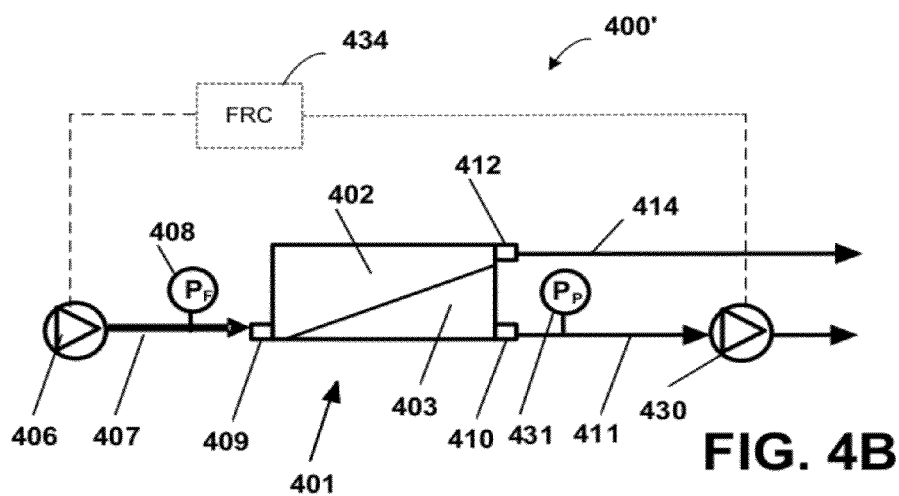

Referring to FIG. 4A, a process and instrument diagram of another SPF process and system 400 similar to system 200 of FIG. 2, includes an SPF membrane separation module 401 and a feed pump 406 and a retentate pump 429 instead of backpressure valve 215 to drive and control the process. The feed pump 406 is set to obtain a suitably low specific feed rate, F, while the retentate pump 429 can be set at the flow rate necessary to obtain the desired conversion, f. The feed pressure 408 of a feed stream 407 and retentate pressure 413 of a retentate stream 414 are not directly set but instead result from the previously set feed and retentate flow rates. If the feed pressure 408 exceeds the maximum allowed by the equipment, then the flow rates of pumps 406 and 429 are proportionately reduced in steps until the feed pressure 408 is at or below the maximum allowable pressure. Referring to FIG. 4B, a process and system 400' represented in FIG. 4B similar to system 400, includes an SPF membrane separation module 401 and a feed pump 406 and permeate pump 430 instead of retentate pump 429 to drive and control the process. The feed pump 406 can be set to obtain a suitably low specific feed rate, F, while the permeate pump 430 can be set at the flow rate necessary to obtain the desired conversion, f. The feed pressure 408 and the permeate pressure 431 are not directly set, but instead result from the feed and permeate flow rates previously set. If the feed pressure 408 exceeds the maximum allowed by the equipment, then the flow rates of pumps 406 and 430 is proportionately reduced in small steps until the feed pressure 408 is at or below the maximum allowable. In this case the permeate pressure 431 may be below atmospheric depending on the pressure of retentate stream 414 (if the retentate stream 414 is at or near atmospheric pressure, then the permeate 411 will be below atmospheric; if the permeate pressure 431 is close to a full vacuum, then the flow rates of both pumps 406 and 430 are reduced to achieve the desired conversion. In an alternative embodiment, system 400' optionally includes a flow ratio controller 434 interposed between the feed pump 406 and the permeate pump 430 and fluidly coupled to the feed stream 407 and retentate stream 414. The flow ratio controller 434 enables setting the conversion to a predetermined factor.

In the various embodiments of the SPF system and process according to the invention, as described in conjunction with the process and instrument diagrams of FIGS. 2, 3, 4A and 4B, the process can be partially controlled by controlling the transchannel pressure differential, TCP. In various embodiments of a TCP-control approach, for example using system 400', the feed pressure 408 is maintained at a targeted value, typically near the highest pressure allowed by the equipment, and by adjusting the feed rate and the retentate pressure to change the TCP until the desired conversion, f, is obtained. Generally, a higher TCP results in a lower conversion. In other embodiments, the process can be controlled by controlling the TMP. Such embodiments are useful, for example, whenever the flux is sensitive to changes in TMP. In various embodiments of a TMP-control approach, the TCP is maintained at a targeted value by maintaining a constant feed flow rate while adjusting the retentate pressure until the desired conversion, f, is obtained. Generally a higher TMP results in a higher conversion.

In various embodiments, the SPF systems and processes of the present invention, employing specific feed rates of less than about 200 lmh, and in other embodiments less than about 100 lmh, to obtain conversions greater than about 50%, have several practical advantages, as follows:

1. the single pass process is a substantially continuous processes, where the feed stream is exposed to the processing equipment for a decreased amount of time;
2. the single pass process has operating conditions that do not require continual adjustment since the feed stream does not change (e.g., in viscosity) unlike in a batch process; and 3. the single pass process has flow rates of feed stream and retentate stream that are typically 3-20 times smaller than those necessary on an equivalently-sized conventional TFF process utilizing recirculation loops, resulting in lower hold-up volume due to the smaller diameter of the pipes; and
4. the single pass process does not require a feed tank since the feed stream coming from an upstream process could be fed directly into the SPF module. The elimination of the tank reduces the equipment cost, the floor space occupied by the equipment, and the hold-up volume.

Figure 5:
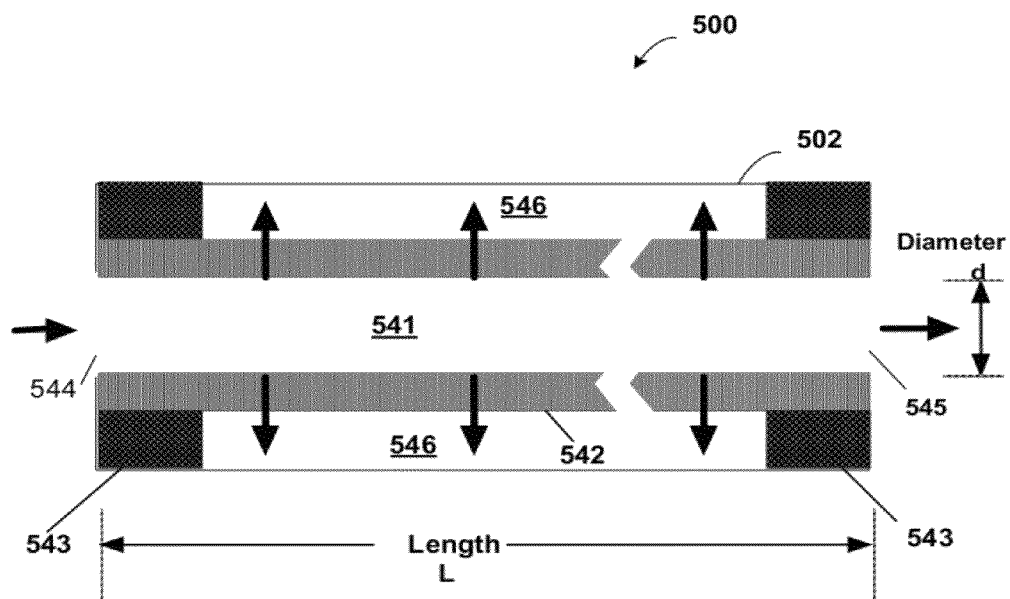
FIG. 5 is a schematic diagram of a longitudinal section of a flow channel of a hollow fiber module formed with hollow fiber membranes according to the invention.

Now referring to FIG. 5, an exemplary hollow fiber module 500 includes a housing 502 and a hollow fiber ultrafiltration membrane 542 disposed within the housing 502. The membrane 542 forms a flow channel 541. The module 500 further includes seals 543 disposed adjacent a channel inlet 544 and a channel outlet 545 to separate the feed stream in the channel 541 from the permeate compartment 546. In operation, the feed stream enters the flow channel 541 at the channel inlet 544, flowing tangentially over the membrane 542 towards the channel outlet 545, driven by, for example, a transchannel pressure differential, TCP, and a transmembrane pressure differential, TMP, generated by at least one pressure source (not shown). As a result of the TMP a portion of the feed permeates through the membrane 542, as indicated by flow arrows from the channel 541 into the permeate compartment 546, providing the permeate in the permeate compartment 546. The flow channel 541 formed by the hollow fiber membrane 542 is further described by its length, L, and lumen diameter, d, as shown in FIG. 5. Flow channels formed with hollow fiber membranes are typically open with no flow obstructions. The specific membrane area, $\sigma_C$ of the flow channel 541 is defined as the ratio of the membrane area contained in the channels divided by the void volume of the channel 541. For channels formed with hollow fiber membranes the specific membrane area is derived from equation 1 as:

$$\sigma_C = \frac{4}{d}. \quad (8)$$

Where d is the diameter of the lumen.

In one embodiment, the flow channel 541 has a specific membrane area greater than about 50 cm$^{-1}$, and in this embodiment the membrane has a hydraulic permeability greater than about 2 lmh/psi. In another embodiment the specific membrane area is greater than about 80 cm$^{-1}$, and in yet another embodiment the specific membrane area is at least about 130 cm$^{-1}$. High specific membrane areas result in higher flux and reduced hold-up-volume of the TFF module. For hollow fiber channels the dimensionless length is given by:

$$\lambda = 4\frac{L}{d}. \quad (9)$$

Where d is the diameter of the lumen; and L is the length of the lumen.

In one embodiment the dimensionless length, $\lambda$, of the flow channel of a module comprising hollow fiber flow channels is greater than about 2,000, in another embodiment greater than about 4,000 and in yet another embodiment greater than 10,000. The values of specific membrane area, $\sigma_C$, and dimensionless length, $\lambda$, in these embodiments enable the hollow fiber module 500 to function effectively in a SPF process similar to the process described in FIG. 2.

Figure 6:
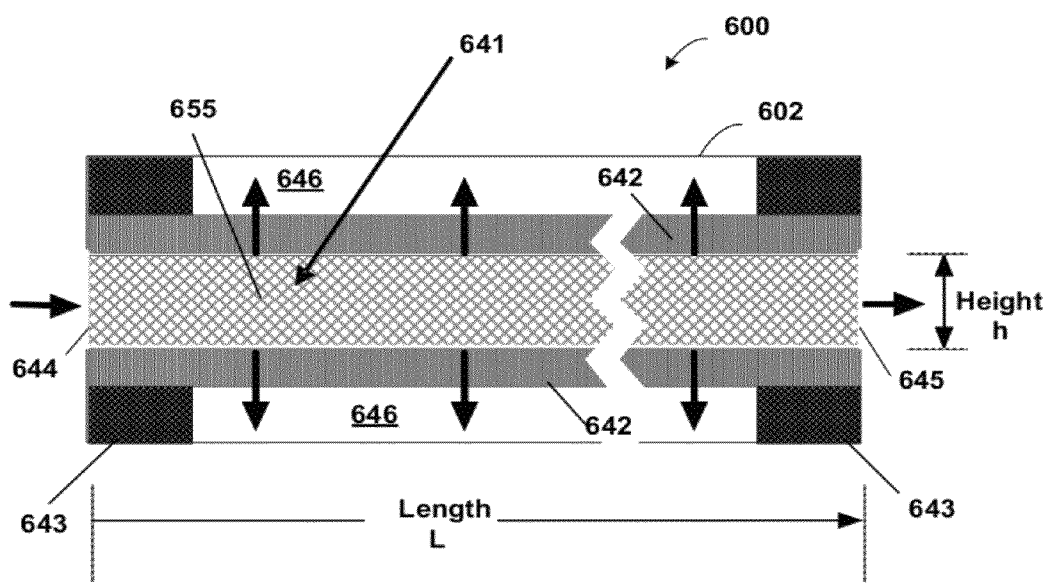
FIG. 6 is a schematic diagram of a longitudinal section of flow channel of a flat-sheet module formed with flat-sheet membranes according to the invention.

Referring to FIG. 6, an exemplary flat sheet module 600 includes a housing 602, an SPF channel 641, disposed within the housing 602, including a flat-sheet membrane 642 disposed adjacent a spacer 655 and seals 643 disposed adjacent a channel inlet 644 and a channel outlet 645 providing the channel 641 on one side of the membrane 642 and a permeate compartment 646 on the other side of the membrane 642. In one embodiment, channel 641 is formed by sandwiching the spacer 655 between two sheets of flat-sheet membrane 642. Channel 641 formed in this manner is referred to as a rectangular channel since it possesses a rectangular cross-section, although it is to be understood that SPF channels are not limited to rectangular cross-sections or any specific topology.

In operation the feed stream enters the channel inlet 644 of the channel 641 and flows tangentially over the membrane surface 642 towards channel outlet 645 of the channel 641, driven, for example, a transchannel pressure differential, TCP, and a transmembrane pressure differential, TMP, generated by at least one pressure source (not shown). As a result of the TMP a portion of the feed permeates through the membrane 642 as shown by flow arrows from the channel 641 thereby providing the permeate. The channel 641, here formed by the flat-sheet membrane 642 can be partially described by its length, L, width (not shown) and height, h. The feed stream can be distributed across the width of the channel 641 by appropriate feed distributors (not shown). The retentate can be collected along the width of the channel 641 by appropriate retentate distributors (not shown). The spacer 655 maintains the membranes in a spaced apart arrangement, and edge seals 643 enclose the channel 641 and form a portion of the permeate compartment 646. There are numerous techniques for forming edge seals known to those skilled in the art. The spacer 655 can be a woven, non-woven, or molded structure, or combinations thereof, that allow the percolation of liquid between its solid structures but are also sufficiently rigid to maintain the channel height h when exposed to compressive loads. The "void fraction" of the spacer 655, $\epsilon$, defined as the ratio of the void volume contained within the spacer to the total volume occupied by the spacer 655, is an parameter known to one skilled in the art, and the structure of the spacer 655 affects the void volume as well as the hydraulic resistance of the channel 641. In one embodiment the spacer 655 is a turbulence-promoting spacer.

The calculation of the specific membrane area $\sigma_c$, the dimensionless length $\lambda$, and the specific feed flow rate F can be provided for a specific channel geometry using the channel height h, and void fraction, $\epsilon$. For example, for rectangular channels, the specific membrane area of the channel is derived from equation 1 as follows:

$$\sigma_C = \frac{2}{\epsilon h}. \quad (10)$$

Where h is the height of the channel; and
$\epsilon$ is the void fraction of the spacer.
The dimensionless length $\lambda$ is derived from equation 5 as follows:

$$\lambda = 2\frac{L}{\epsilon h}. \quad (11)$$

Where L is the length of the channel
h is the height of the channel; and
$\epsilon$ is the void fraction of the spacer.
Specific formulas for these parameters for channels having alternative topologies can be derived from the dimensions of the channel 641 or can computed empirically as is known in the art. In one embodiment, the channel 641 has a specific membrane area greater than about 40 cm$^{-1}$ and in another embodiment the channel 641 has a specific membrane area greater than about 50 cm$^{-1}$. The specific values of specific membrane area, $\sigma_c$, and dimensionless length, $\lambda$, in these embodiments enable the channel 641 to function effectively in a single-pass process run continuously at low specific feed flow rates, F, similar to the process described in FIG. 2.

Figure 7A:
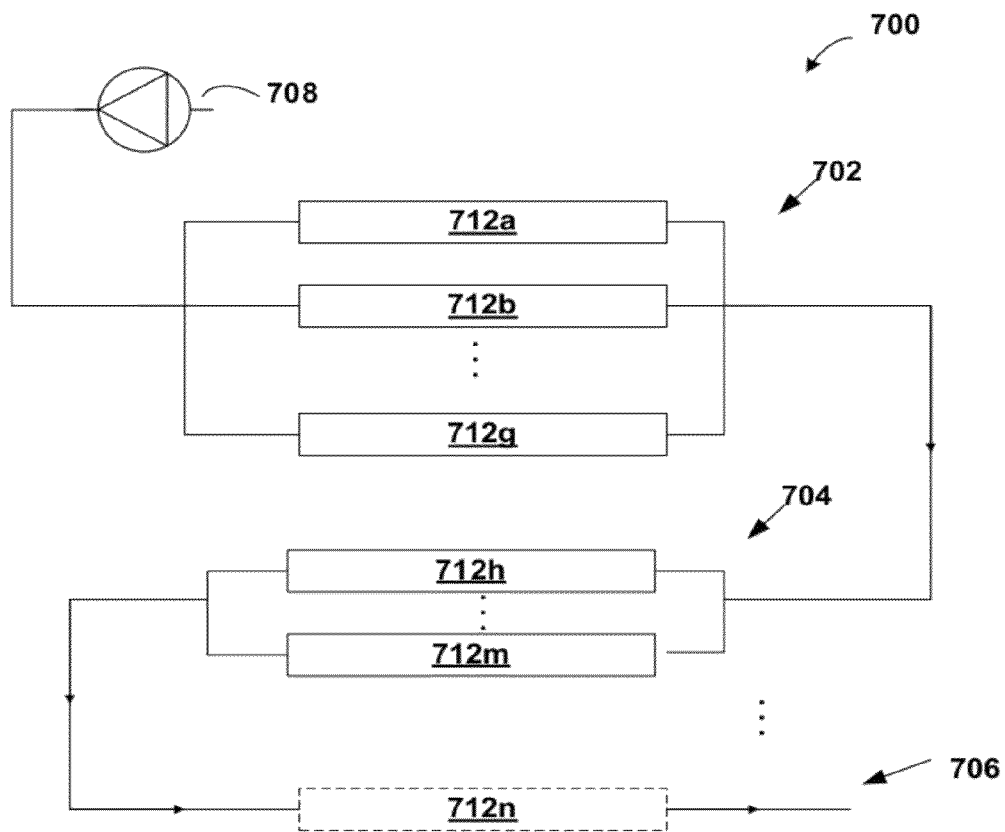
FIG. 7A is a schematic block diagram of a multi-stage system according to the invention.

Now referring to FIG. 7A, an SPF system 700 for the filtration of liquids using an SPF process, includes a plurality of stages 702 and 704, each stage having a plurality of channels 712a-712g and 712h-712m (collectively referred to as channels 712), respectively. The system 700 further includes a pressure device 708 fluidly coupled to the first stage. The system 700 can optionally include a stage 706 with a single channel 712m. The stages 702 and 704 are disposed such that each stage is in fluid communication with each adjacent stage preceding it and is in fluid communication with each adjacent stage that follows it (i.e., the retentate from the i$^{th}$ stage becomes the feed of the (i+1)$^{th}$ stage). Each of the channels 712 comprises a filtration membrane. As described above, each of the channels 712 has a length, a membrane area, a void volume, a specific membrane area expressed as a ratio of the membrane area to the void volume, and a dimensionless length expressed as a product of the channel length and the specific membrane area. In the configuration of FIG. 7A, the dimensionless length of each stage 702, 704 and 706 is equal to the dimensionless length of the longest of channel 712 in each stage. It is understood that the channels 712 could be identical or could have varying properties, a stage could have multiple channels in series, in parallel, in a series parallel arrangement, and that the number of stages in system 700 could be greater than three.

In one embodiment the channels 712 in any one of the stages 702 and 704 are substantially identical. In the embodiment of FIG. 7A the first stage 702 has a greater number of channels than the second stage 704 although in other embodiments the stages 702 and 704 could have the same number of channels. The system 700 can be implemented as either internally or externally staged system. In an internally staged system a housing, for example a cassette holder having two flat plates, includes the stages 702, 704 and 706 and is generally sealed and has external feed, permeate and retentate connections. In an externally staged system the stages are coupled together with discrete external connections. Here the flow paths through channels 712 are connected by serially connecting stages 702, 704, and 706 together, thereby forming a serial flow path in the feed/retentate compartments, instead of the conventional parallel connections in TFF systems. Thus the resulting effective channel (i.e., the serial combination of channels) in an SPF embodiment is characterized as being a relatively long thin channel as compared to channels in conventional systems.

System 700 is operated in SPF mode as described above in conjunction with FIG. 2, (i.e. continuously supplying the feed stream at a relatively low specific feed flow rate using a relatively small feed supply device). Separation performance is maintained in the stages 702, 704, and 706 by varying at least one filtration property of one stage relative to a preceding stage so as to match the separation properties of the stage to the conditions of the feed stream at that stage. A filtration property is a stage property which affects, for example, the conversion, the TMP, and flux performance, and includes but is not limited to, the cross-sectional flow area of the stage, the specific membrane area of the stage, the number of channels in the stage, the hydraulic diameter of a feed spacer disposed adjacent the membrane and within the channel of a stage, the dimensionless length, and the filtration membrane properties. Here the variation in stage properties of stages 702, 704, and 706, is the number of channels 712 per stage. One result of changing the number of channels 712 per stage is to affect the velocity of the feed stream so that flux performance is maintained under conditions of high conversion throughout the stages 702, 704 and 706. It is noted that varying the number of channels 712 per stage is similar to varying the cross sectional area of the stages.

A further advantage to staging in an SPF system is that staging allows a long flow path without excessive pressure drops. Another advantage of the present invention is the elimination of the need to include a pump or other pressure source between stages. Also, a biopharmaceutical feed stream can be efficiently processed using conventional filtration membranes with well understood properties in system 700 while achieving a relatively high conversion and reducing system complexity, hold-up volume and exposure time. There are numerous ways of arranging channels and stages in both internally-staged module and externally-staged systems, including, but not limited to, modules comprising different types of filtration membranes, for example, (a) hollow fiber membranes, (b) flat-sheet membranes, and (c) membrane monoliths. Staging in which the cross-sectional area for flow of the module decreases along the flow path, can be provided in several ways. In other embodiments, suitable for almost all membranes, one approach is to decrease the number of channels in each stage along the flow path, the dimensions of each channel being substantially the same in all stages. In other embodiments, where the stages comprise rectangular channels, one method is to reduce the width of the channel along the flow path while keeping the specific membrane area of the channel substantially the same. In still other embodiments, the channel width varies continuously along the flow path, with the width at an inlet of the channel of a stage being greater than the width at an outlet of the channel, and in one example the inlet width is about 1.2 times greater than the outlet width. In other embodiments the inlet width of the channel is about two times greater than the outlet width. In some other embodiments, channels having a continuously varying width are used in conjunction with a staged system, and in still other embodiments, un-staged modules include channels having a continuously varying width. These methods for reducing the cross-sectional area can be combined.

The staging in system 700 is generally referred to as retentate staging because the retentate from one stage serves as a feed to the next stage. The boundary between a stage and an adjacent following stage in an SPF multi-stage system can be provided in a number of additional ways. A transition in a physical property of the membrane in the channels can define a stage boundary. For example the membrane filter, the dimensionless length of the channels, the hydraulic diameter of the spacer in the channel, the thickness of the flow channels and the total cross-section for feed flow may change between stages. A stage transition also occurs where there is a discontinuity in the composition of the fluid between a stage and an adjacent stage. This type of discontinuity is affected, for example, by introducing a diafiltration stream at the boundary of two stages. In a diafiltration system, the stage can include the same number of substantially identical channels as the adjacent preceding stage, and SPF operation is enabled by the introduction of diafiltrate at the intersection of two stages as described below in conjunction with FIGS. 13A, 13B, 18A, 18B, 19A, 19B and 20. Another form of stage transition can be provided by a discontinuity in the operating conditions of the separation process, for example, transmembrane pressure in the adjacent stages. Such a transition can be achieved, for example, by a discontinuous change in the pressure of the permeate compartment, the feed compartment, or both. In alternative embodiments the property change can include providing permeate control in each stage as discussed below in conjunction with FIG. 21. A stage transition can also be provided by applying external controls. For example, providing heating or cooling at various stages in system 700. The tailoring of physical properties or operating conditions to each stage leads to improved separation processes. In certain multi-stage embodiments, SPF operation can be achieved without the requirement of $\sigma_c$ being greater than about 40 $cm^{-1}$.

In various embodiments, SPF modules with internal staging comprise one or more of: (a) decreased cross-sectional area for flow along the flow path so as to boost the liquid velocity within the flow channel to compensate for the lower velocity induced by permeation and thereby boost the flux performance of the flow channel; (b) increased specific membrane area of the channel along the flow path so as to boost the flux performance of the channel; (c) changed permeation properties of the membrane along the flow path so as to optimize the balance between flux and rejection in any given stage; and (d) ports and flow passages for the introduction of the diafiltrate at various points along the flow path. Internally-staged modules having some of the properties described above are described below in conjunction with FIGS. 8B, 8C, 9A, and 9B.

In one embodiment using flat-sheet membranes, the cross-sectional area of a channel is reduced by decreasing the width of the channel along the flow path. The channel height can be varied within the channel, but this alternative is less practical. It has been recognized that these property changes increase efficiency because high conversion leads to lower liquid velocities within a channel. The lower velocities have two potential consequences: reduced flux due to a diminished sweeping action, and reduced TCP. While the lower flux is generally an unfavorable consequence of high conversion, the lower pressure drop per unit of flow path length enables an increase in the overall flow path length which leads to higher single pass concentration factors without resulting in excessive inlet pressures. Property changes along the flow path are implemented so as to increase the flux of the module, for example, by taking advantage of the reduced TCP obtained by using the SPF process. Changing the sieving coefficient also leads to improved separation effectiveness. In certain embodiments, the channels in the module have a substantially continuously changing physical property along the flow path or can change discretely as in FIG. 7A. In other embodiments the property change is monotonic between each stage and an adjacent following stage. SPF modules and systems using membrane monoliths (e.g., ceramic membranes) are similar in structure and operate similarly to hollow fibers modules and systems as described below.

Figure 7C:
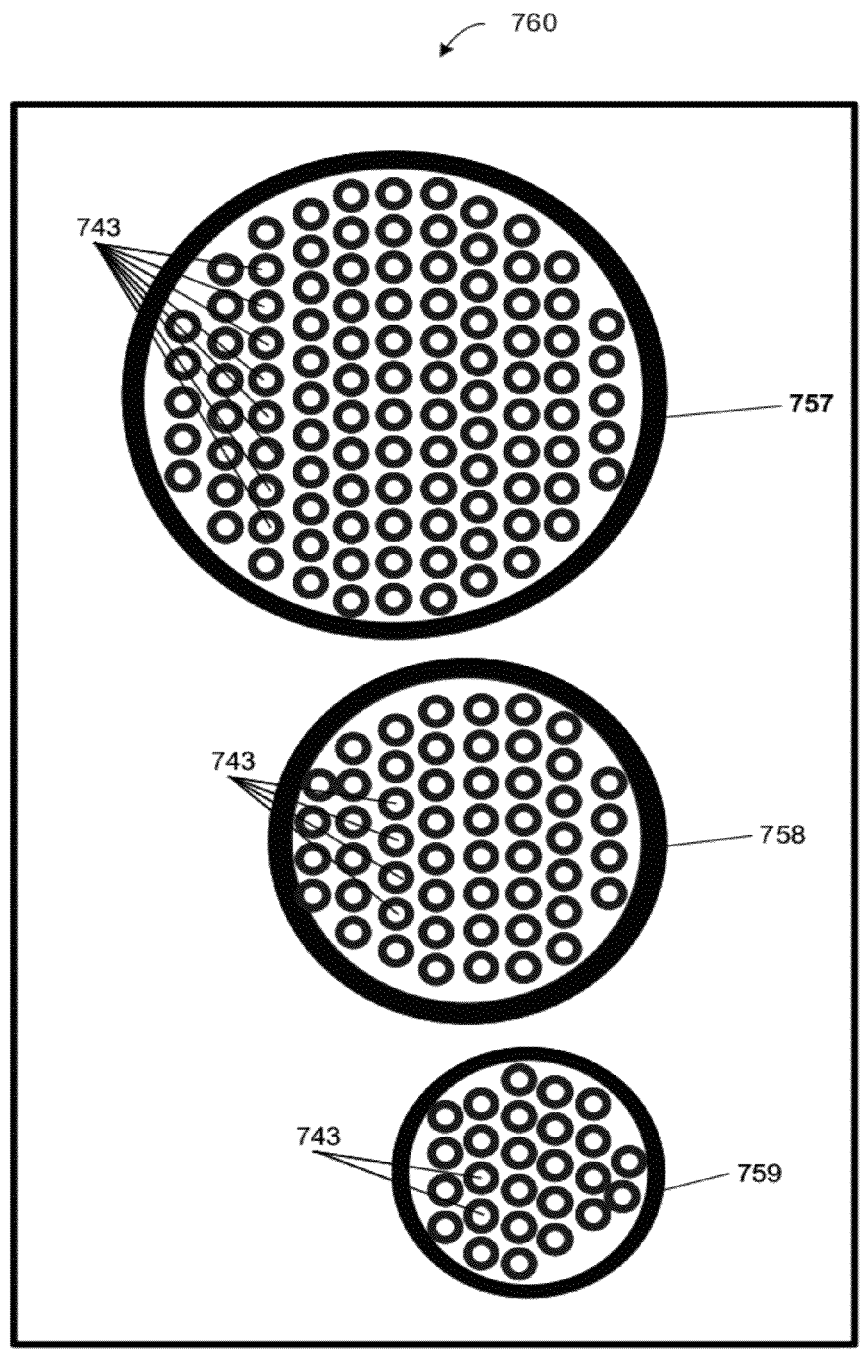

Further detailed descriptions of various embodiments of internally-staged modules with staging are discussed in the context of FIGS. 7B, 7C, 8B and 8C. FIGS. 7B and 7C are schematic diagrams of various embodiments of the cross-section of internally-staged modules in which the staging property change is accomplished by reducing the cross-sectional area for flow along the flow path while maintaining substantially the same channel dimensions, and therefore, maintaining substantially the same specific membrane area of the channel.

Referring to FIG. 7B, an exemplary module 718 comprises a housing 720, stages 722a, 722b-722n (collectively referred to as stages 722) having a plurality of substantially identical channels 724, here rectangular channels disposed within the housing 720. Each channel 724 comprises a membrane 726 disposed adjacent to a feed spacer 728 which provides support for the membrane 726. In one embodiment, the channels 724 have $\sigma_c$ values of greater than about 40 $cm^{-1}$ and $\lambda$ values of less than about 6,000. In this embodiment, $\lambda_{stage}$ is equal to $\lambda$ because there is one channel 724 in the longest serial flow path in the stage, and the $\lambda_{system}$ (i.e., the $\lambda$ of the module) for module 718 is the sum of the dimensionless lengths of the stages 722 and is in one embodiment greater than 2,000. The module 718 further includes an inlet manifold 730 and outlet manifold 732 fluidly coupled to the channels 724 of the first stage 722a, an inlet manifold 736 and outlet manifold 738 fluidly coupled to the channels 724 of the second stage 722b, and a passageway 734 fluidly coupling outlet manifold 732 with inlet manifold 736. It is understood that module 718 can comprise several additional stages 722 having the same or different number of channels 724 coupled preceding and following stages 722 in a similar way as stages 722a and 722b such that each stage 722 is in fluid communication with each adjacent stage 722 preceding it and is in fluid communication with each adjacent stage 722 that follows it. The module 718 further includes an inlet manifold 740 and outlet manifold 746 fluidly coupled to the channels 724 of the final stage 722n. The outlet manifold 746 disposed in the housing provides the retentate output for further processing through a retentate port (not shown). Module 718 also includes a feed and a permeate ports (not shown).

In the embodiment of FIG. 7B, the first stage 722a comprises four channels, and is followed by and is fluidly coupled to the adjacent second stage 722b which comprises two channels 724. Here the final stage 722n comprises a single channel 724. While the permeate from the three stages 722 can be collected together in parallel (for clarity permeate connections are not shown), the retentate from one stage 722 becomes the feed to the following adjacent stage 722; more specifically, the retentate of the first stage 722a becomes the feed of the second stage 722b, and the retentate of the second stage 722b becomes the feed to the final stage 722n. Since the channels 724 have substantially the same channel height, length and width in the stages 722, here for example, the cross-sectional area of the final stage 722n is half that of the second stage 722b, which in turn is half that of the first stage 722a. This results in adjacent stages having a cross-sectional area ratio equal to about 0.5.

In one embodiment, the channels 724 are straight. However, it is to be understood that the channels 724 need not be straight; but rather can be straight, coiled, arranged in zigzag fashion, and in general can have any topology wherein an effective tangential flow across the membrane 726 can be maintained. Although three stages 722 are shown in FIGS. 7B and 7C, it is understood that the embodiments of internally-staged modules of the present invention are not limited to three stages; rather other embodiments can include two-stages as well as those with more than three stages.

In various embodiments, the properties of the membrane 726 change in each stage 722 along the flow path. It is known to those skilled in the art that a small change in the retention of an ultrafiltration membrane (e.g., from 99% to 99.9%) often results in a significant change in the hydraulic permeability of the membrane. The membrane with the higher retention is referred to as a "tight" membrane, while the membrane with the lower retention is referred to as a "loose" membrane. This phenomenon is exploited in various embodiments by increasing the retention of the membrane 726 along the flow path. In various embodiments, the higher flux characteristic of looser membranes in the upstream stages can be used advantageously, while decreasing, or preventing, excessive permeation losses by using tighter membranes in the downstream stages. Different applications can take advantage of changing different membrane properties in this kind of staging.

In addition to the channel properties variations described above, channel properties can be changed by: changing the specific membrane area; changing the filtration membrane properties; changing the hydraulic diameter of the feed spacer 728. The hydraulic diameter is related to flow resistance and is a function of the spacer properties. A change in the membrane property includes a change in membrane permeability and a change in the MWCO of the membrane. In one embodiment the ratio of the cross-sectional area of a first stage to the cross-sectional area of a second stage is greater than about 1.1. In another embodiment, the ratio of the specific membrane area of a channel in the first stage to the specific membrane area of a channel in the second stage is greater than about 1.25. In still another embodiment, the ratio of the cross-sectional area of the first stage to the cross-sectional area of the second stage is less than about 0.8. The module 718 is operated in SPF mode as described above in conjunction with FIGS. 2 and 7A.

Certain higher flux applications are realized using embodiments comprising high permeability ultrafiltration membranes, with $\sigma_c$ values of greater than 40 cm$^{-1}$. In such embodiments, it is beneficial to limit the value of $\lambda_{stage}$ in order to limit the change in fluid velocity or concentration in a stage and thus to make the transition to the next stage, where the next stage has properties more suited to the reduced fluid velocity or higher concentration. If the viscosity of the flowing material rises significantly, it may be desirable to increase the hydraulic diameter of the channels in the stages at frequent intervals in order to limit the pressure drop. If the concentration of the species that is being retained becomes very high, it is beneficial to use tighter membranes or membranes with lower molecular weight cut-offs in the downstream stages in order to reduce losses of the retained species in the permeate. However, when using stages with limited values of $\lambda_{stage}$ the value of $\lambda_{system}$ must nevertheless be large enough to achieve the total concentration factor or conversion desired.

When diafiltration is used, limiting the value of $\lambda_{stage}$ results in the use of a larger number of stages for a given degree of impurity removal and results in a lower consumption of diafiltrate. In some embodiments, it is particularly beneficial to limit the value of $\lambda_{stage}$ to less than 3,500, while increasing the value of $\lambda_{system}$ to more than 2,000 in staged systems which use modules with a $\sigma_c$ value of greater than 40 cm$^{-1}$. There is no particular limit on the lowest value of $\lambda_{stage}$, aside from the expense of using a large number of small stages. In some embodiments, more that two stages are used and in other embodiments more than four stages are used. The shorter stages (i.e. having smaller values of $\lambda_{stage}$) allow for finer control of the property changes among stages and this control contributes to maintaining the fluid velocity along the flow path at a desirable value. It should be understood that the higher the flux (the higher the hydraulic permeability of the membrane) the shorter the stage needs to be. Therefore, there is an inverse relation between hydraulic permeability of the membrane and $\lambda_{stage}$. In one embodiment, the initial hydraulic permeability of the membrane (i.e., before the membrane is conditioned by use) is greater than about 0.5 lmh/psi. In other embodiments, staging maintains the separation performance in single pass operation by affecting at least one of: a transmembrane pressure (TMP); a feed stream velocity; and a bulk concentration of the solute. Each stage in these embodiments is designed to provide desirable conditions in each stage.

Referring to FIG. 7C, a module 760 comprises three stages 757, 758 and 759 comprising hollow fiber channels 743. The first stage 757 is followed by the second stage 758 and finally the third stage 759, each stage comprising, in this example, 104, 52, and 26 channels, respectively. The stages 757, 758 and 759 can be fluidly coupled using techniques known in the art and also in arrangements described in conjunction with FIGS. 16A-18B. In operation, the permeate from the three stages is collected together, the retentate from one stage becomes the feed to the adjacent following stage. The retentate of the first stage 757 becomes the feed of the second stage 758, and the retentate of the second stage 758 becomes the feed of third stage 759. Since the channels 743 in this example have substantially the same lumen diameter and length in the three stages 757, 758 and 759, the cross-sectional area of the third stage 759 is half that of the second stage 758, which in turn is half that of the first stage 757. This results in contiguous stages having a cross-sectional area ratio equal to about 0.5. The module 760 is operated in SPF mode as described above in conjunction with FIGS. 2 and 7A.

Figure 7D:
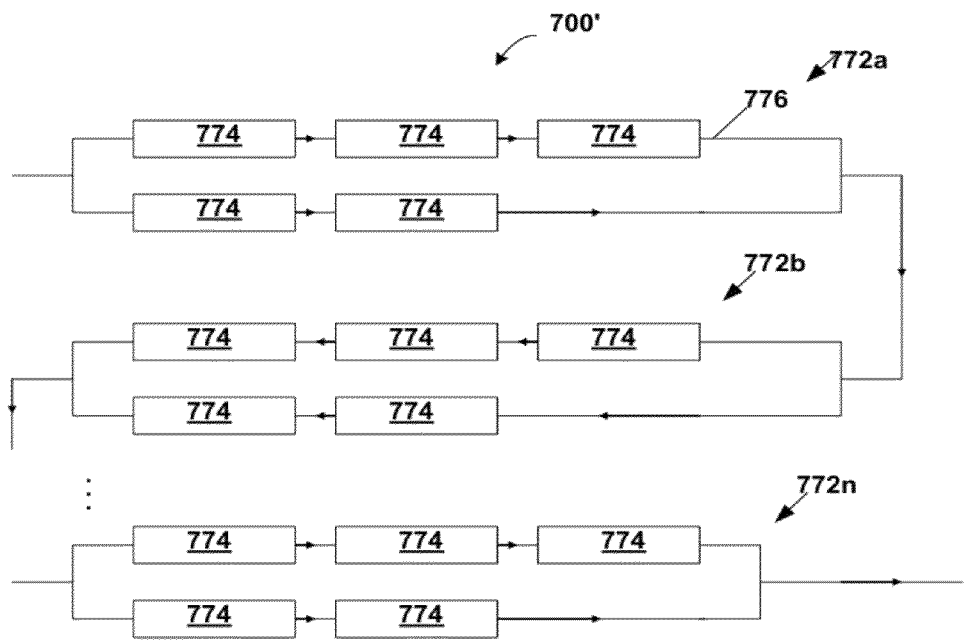
FIG. 7D is a schematic diagram of a multi-stage system having stages with multiple serial flow paths according to the invention.

Now referring to FIG. 7D, a system for the ultrafiltration of liquids 700' similar to the system 700 of FIG. 7A includes a plurality of substantially identical stages 772a-772n (collectively referred to as stages 772), each stage 772 having a plurality of channels 774. Here, each stage 772 has a series-parallel arrangement of channels in a "three over two" configuration. As described above, each of the channels 774 has a length, a membrane area, a void volume, a specific membrane area $\sigma_c$, expressed as a ratio of the membrane area to the void volume, and a dimensionless length $\lambda$ expressed as a product of the channel length and the specific membrane area. In the configuration of FIG. 7D, the dimensionless length of each stage 772 is equal to the dimensionless length of the longest serial flow path 776 of each stage 772. In this example, the dimensionless length of each stage 772 $\lambda_{stage}$ would be 3*$\lambda$, and dimensionless length of the system 700', $\lambda_{system}$ would be 9*$\lambda$. In one embodiment, the specific membrane area of channel 774 is greater than about 40 cm$^{-1}$, dimensionless length of the system is greater than about 2,000 and the dimensionless length of at least one of the plurality of stages is less than about 6,000. In an alternative embodiment, the dimensionless length of the system is greater than about 4,000 and the dimensionless length of the at least one of the plurality of stages is less than about 3,500. By using relatively short flow paths (i.e., small values of $\lambda_{stage}$) for individual stages the fluid velocity can be maintained at reasonable levels in any given stage. By using large values for the overall system flow path length (large values of $\lambda_{system}$) a high degree of concentration is achieved. Even though the stages 772 have flow path with unequal length, system 700' can be operated in SPF mode as described above in conjunction with FIGS. 2 and 7A although not as efficiently as a system with stages having equal flow path lengths.

Figure 8A:
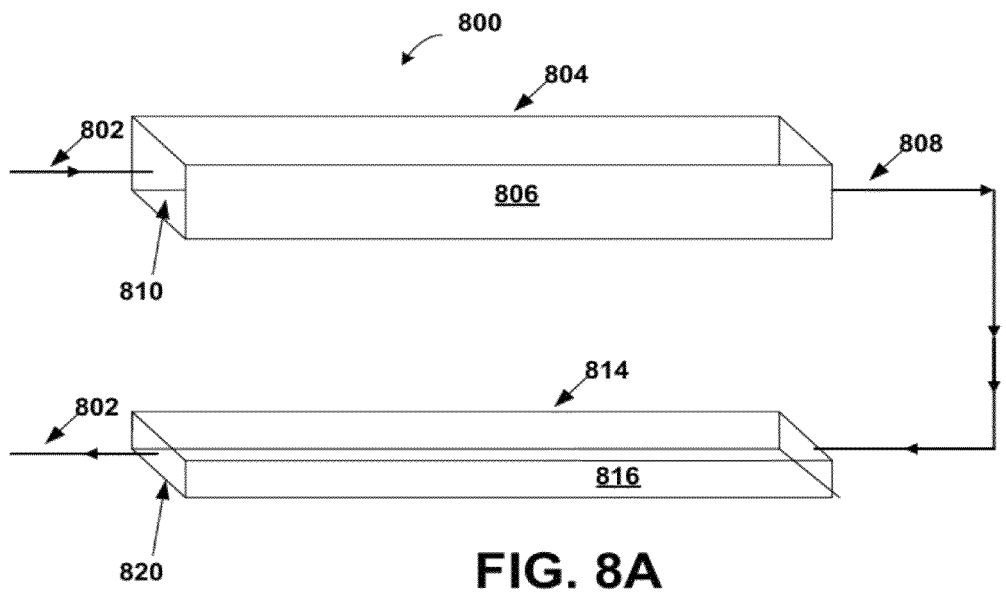
FIG. 8A is a perspective diagram of a multi-stage system according to the invention having stages including channels with differing specific membrane area.

Now referring to FIG. 8A, an exemplary module for the ultrafiltration of liquids 800 includes stages 804 and 814 in which the staging is accomplished by increasing the specific membrane area of the stage along the flow path while maintaining substantially the same number of channels in each stage, here, one channel. Here channel 816 in stage 814 is thinner than channel 806 in stage 804. Since the volumetric flow rate at the exit of 804 is the same as the volumetric flow rate at the inlet of 814, the effect of the thinner channel length is to increase the velocity in stage 814. It is understood that the specific membrane area of the stage and the height of the channels are related and that changing a spacer property can change the specific membrane area of the stage. Furthermore, the specific membrane area of a stage can be changed without changing the cross section for flow of the stage.

Figure 8B:
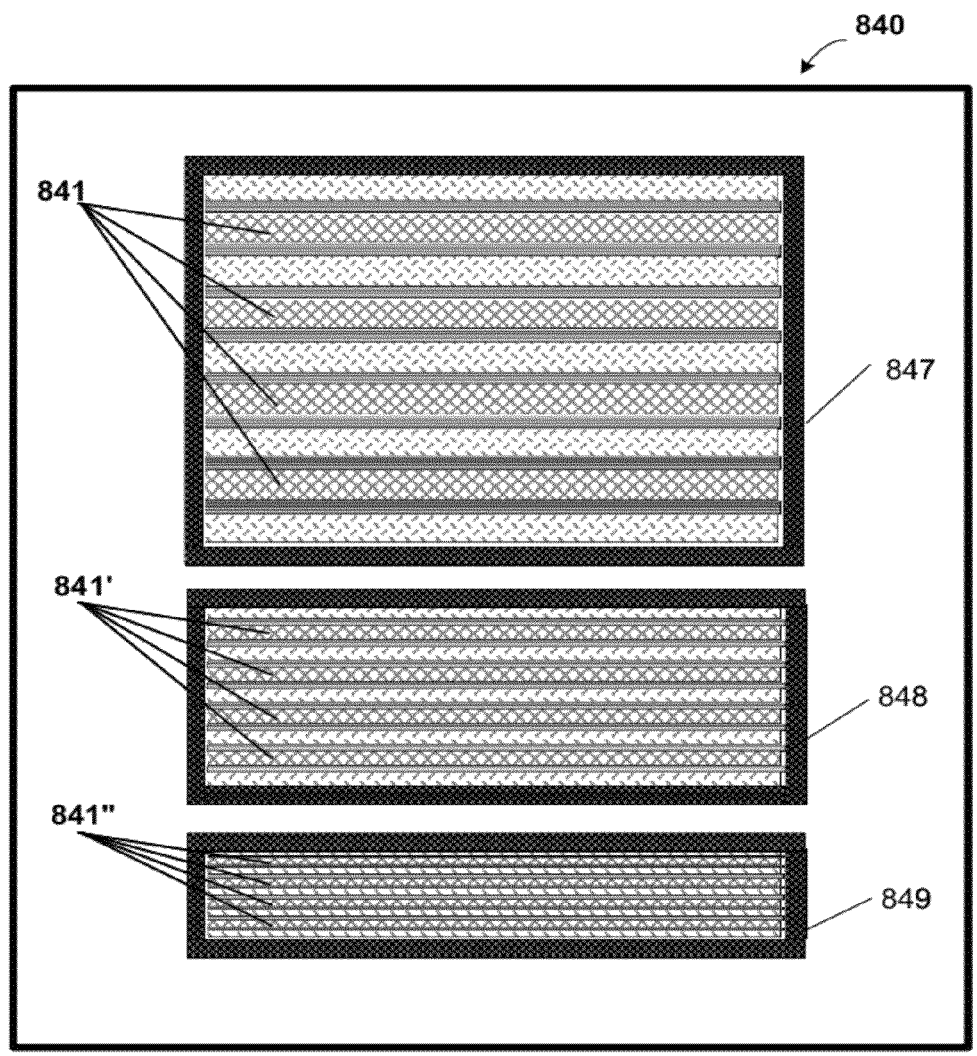
FIGS. 8B and 8C are schematic diagrams of internally-staged modules according to various embodiments of the present invention, where staging is accomplished by increasing the specific membrane area of channels in each stage along the flow path.
Figure 8C:
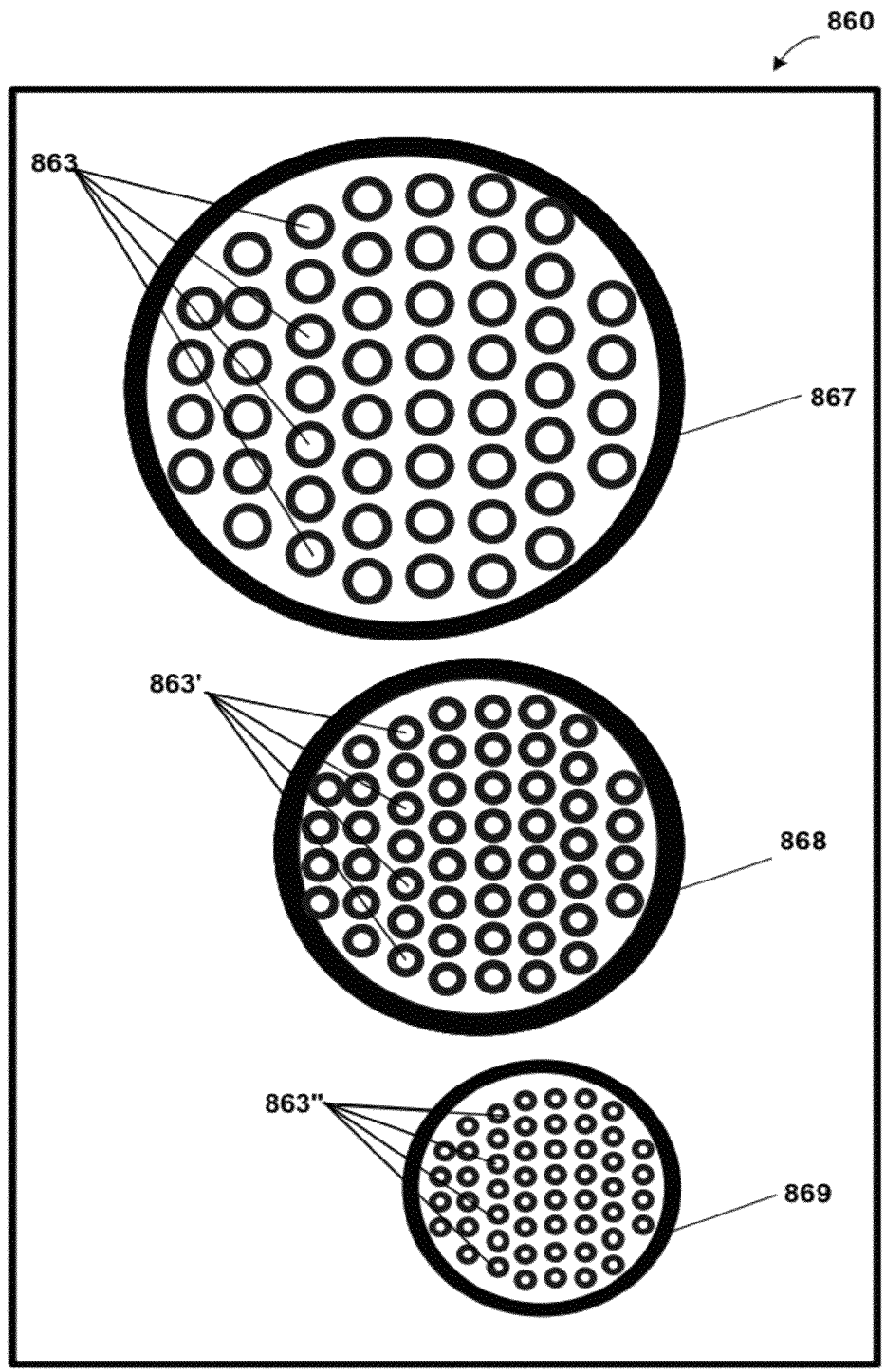

Referring to FIG. 8B, a module 840 comprises three stages 847, 848 and 849 made with rectangular channels 841. The first stage 847 is followed by the second stage 848 and finally the third stage 849, each stage having the same number of rectangular channels 841, 841' and 841", respectively. For clarity, the flow channels represented by FIGS. 8B and 8C are depicted as straight and rectangular. However, it is to be understood that the flow channels need not be straight or rectangular; but rather can be coiled, arranged in zigzag fashion, and in general can have any topology which supports tangential flow. Although three stages are shown in FIGS. 8B and 8C, it is to be understood that the internally-staged embodiments of the present invention are not limited to three stages. The stages 847, 848 and 849 can be fluidly coupled using techniques known in the art and similar to the arrangement described in conjunction with FIG. 13B (without the diafiltration distributor).

In operation, the permeate from the three stages is collected together and the retentate from one stage becomes the feed to the contiguous stage downstream, more specifically, the retentate of the first stage 847 becomes the feed of the second stage 848, and the retentate of the second stage 848 becomes the feed of the third stage 849. Here the rectangular channels 841, 841' and 841" have different heights. The specific membrane area of each stage increases along the flow path by virtue of a decreasing channel height, contiguous stages having a specific membrane area ratio, equal to about two, with a corresponding channel height ratio, equal to about 0.5. As a result, the cross-sectional area of the third stage 869 is half that of the second stage 848, which in turn is half that of the first stage 847. In this embodiment, the contiguous stages have a cross-sectional area ratio, equal to about 0.5. In various other embodiments it is possible to have a cross-sectional area ratio equal to 1.0 while still keeping the specific membrane area ratio equal to about 2.0, for example, by doubling the number of channels in each subsequent stage. Therefore, for embodiments in which the specific membrane area ratio increases it is possible to have the cross-sectional area ratio decrease as represented by FIG. 8A, stay the same as described here, or even increase, by changing the number of channels in each stage along the flow path.

Referring to FIG. 8C, a module 860 according to the invention comprises three stages 867, 868 and 869. Stage 867 comprises a plurality of hollow fiber channels 863, stage 868 comprises a plurality of hollow fiber channels 863' and stage 869 comprises a plurality of hollow fiber channels 863". The first stage 867 is followed by the second stage 868 and finally the third stage 869, here, each stage has the same number of hollow fiber channels, but the hollow fiber channels in each stage have different diameters. The specific membrane area of each stage 867, 868 and 869 increases along the flow path due to a decreasing lumen diameter. With a corresponding lumen diameter ratio, equal to about 0.707 for example, adjacent stages have a specific membrane area ratio equal to about 1.41. As a result, the cross-sectional area of the third stage 869 is half that of the second stage 868, which in turn is half that of the first stage 867. Here, the adjacent stages have a cross-sectional area ratio equal to about 0.5. In other embodiments it is possible to have a cross-sectional area ratio equal to approximately 1.0 while still keeping the specific membrane area ratio equal to about 1.41, for example, by increasing the number of channels in each subsequent stage by about 41%. Therefore, for embodiments in which the specific membrane area ratio increases it is possible to have the cross-sectional area ratio (a) decrease (as represented by FIG. 8B), stay the same or even increase, by changing the number of channels in each stage along the flow path.

The permeates from the three stages are collected together and the retentate from one stage becomes the feed to the adjacent following stage; more specifically, the retentate of the first stage 867 becomes the feed of the second stage 868, and the retentate of the second stage 868 becomes the feed of the third stage 869. The stages 867, 868 and 869 can be fluidly coupled using techniques known in the art. In general, any number of stages greater than two can be used in the internally-staged or externally staged embodiments of the present invention. In certain applications, the number of stages chosen is based on a tradeoff between module cost and the benefits of improved performance offered by an increased number of stages, for example higher flux and finer TMP control. Some embodiments have fewer than twenty stages, and other embodiments have fewer than ten stages. The ratio of the change in separation properties between stages is based on a number of factors including the number of stages and the overall separation objective desired for the system. In various embodiments of staging based on decreasing the cross-sectional area of stages, cross-sectional area ratios of about 0.3 to about 0.9 are used, with a ratio range of about 0.5 to about 0.8 in other embodiments. In various embodiments of staging based on increasing the specific membrane area of stages, specific membrane area ratios of about 1.2 to 3.0 are used, with a specific membrane area ratio range of about 1.3 to about 2.0 in other embodiments. In still other embodiments of staging based on increasing the retention of the membrane on each stage, the ratio of the sieving coefficient of the retained species, of about 0.1 to 0.75 are used, with a range of about 0.1 to about 0.50 in other embodiments.

High fluxes made possible by the use of modules, comprising filtration membranes channels, with $\sigma_c$ values of greater than about 40 cm$^{-1}$. It is beneficial to limit the value of $\lambda_{stage}$ for these modules in order to limit the change in fluid velocity or concentration in the stage and thus to make the transition to the next stage, where the next stage may have properties more suited to the reduced fluid velocity or higher concentration. However the value of $\lambda_{system}$ must be large enough to provide the desired concentration. One embodiment limits the value of $\lambda_{stage}$ to less than about 6,000, with the value of $\lambda_{system}$ being greater that about 4,000 in staged systems with channels having a $\sigma_c$ value of greater than about 40 cm$^{-1}$. There is no particular limit on the lowest value of $\lambda_{stage}$ aside from the complexity and expense of using a large number of short stages. The limitation on $\lambda_{stage}$ is also applicable to modules including hollow fiber membranes.

Figure 9A:
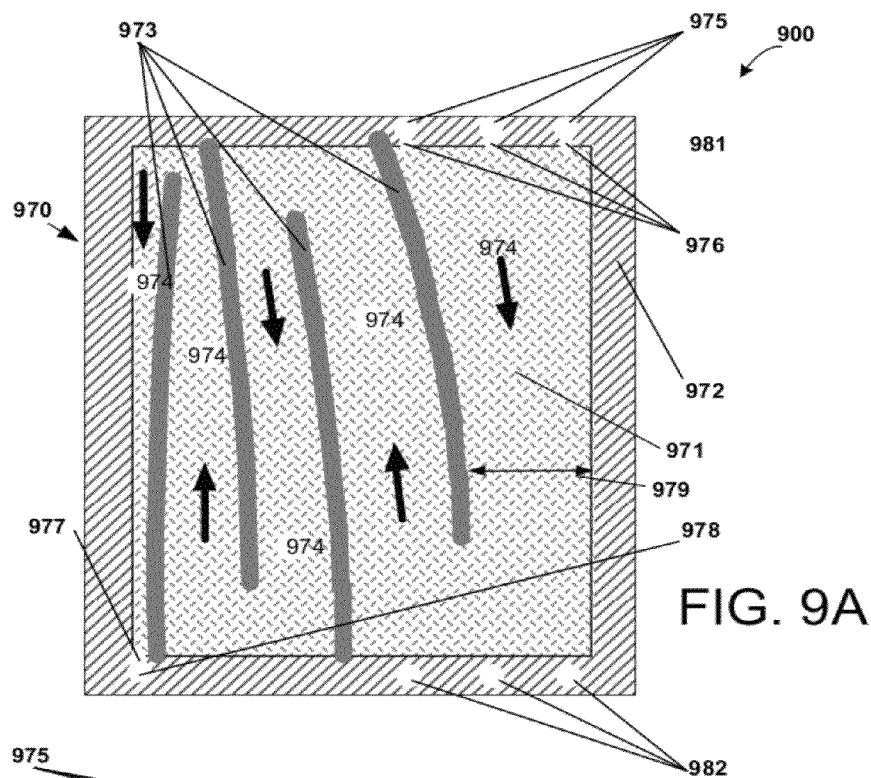
FIGS. 9A and 9B are schematic diagrams of feed and permeate compartments, respectively, of an internally-staged module comprising rectangular channels having decreasing cross-sectional area along the flow path according to the invention.

Referring now to FIG. 9A, a non-staged module 900 according to the invention has a substantially continuously changing physical property along the flow path. Module 900 includes a feed compartment 970 comprising a feed spacer 971 and a sealant forming shell 972. The module 900 includes a plurality of secondary flow passages 976, fluidly coupled to a plurality of feed primary flow passages 975. The module 900 further includes ribs 973 disposed adjacent the feed spacer 971 forming a channel 974 whose width diminishes along the channel length. In one embodiment the ribs 973 are molded into the feed spacer 971. The module 900 further includes secondary flow passage 977 fluidly coupled to retentate primary flow passage 978 and permeate primary passages 982 coupled to a permeate compartment. In one embodiment, the width of at least one channel 974 decreases by a factor greater than about two from an inlet of the channel 974 to an outlet of the channel 974. In one embodiment, the width of at least one channel 974 decreases by a factor greater than about four from an inlet of the channel 974 to an outlet of the channel 974 and additionally the channel has a dimensionless length greater than about 2,000 and in another embodiment greater than about 3,000, and in yet another embodiment greater than about 4,000.

Figure 9B:
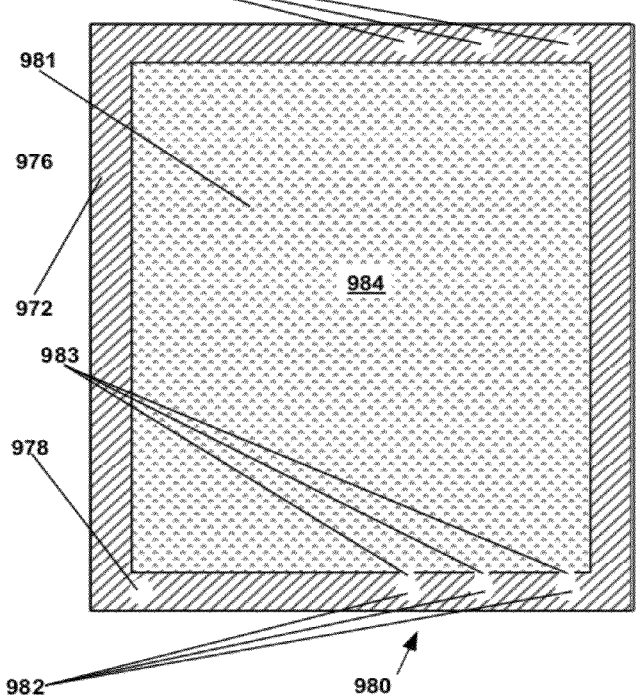

Referring to FIG. 9B, in which like elements are provided having like reference designations as in FIG. 9A a permeate compartment 980 is formed with a permeate spacer 981 and a sealant forming shell 972. The quantity, size and location of feed, retentate and permeate flow passages, is based on multiple factors such as, for example, the desired flow rates (which are in turn determined by the dimension of each stack and the number of stacks in each module), the desired location of the feed, retentate and permeate ports of the module, and by desired cleaning and purging considerations. The properties of the permeate spacer are selected, among other considerations, to minimize hold-up volume, provide adequate support to the membrane and to prevent excessive pressure differentials within the permeate compartment. The feed compartment 970 of FIG. 9A is aligned with the permeate compartment 980.

In operation, a feed stream is introduced into the feed compartment 970 through the plurality of secondary flow passages 976, fed in turn by feed primary flow passages 975, the latter can span the whole module and form a feed manifold for the module. The secondary flow passages 976 introduce the feed stream into inlet end of the channel 974, inducing tangential flow in the channel 974. The tangential velocity of the liquid within the channel, represented by the arrows, remains substantially constant along the channel length by virtue of the diminishing channel width 979. Retentate exits the channel 974 through the secondary flow passages 977 located at the outlet end of the channel 974, the secondary flow passages 977 further feeding retentate primary flow passage 978 which can span the entire module 900 and forming a retentate manifold. The permeate stream enters a permeate compartment 984 by permeating through a membrane (not shown) separating feed compartment 970 from adjacent permeate compartment 980. Permeate can be collected by means of a plurality of permeate secondary flow passages 983 which in turn feed permeate primary passages 982, which can span the whole module forming a permeate manifold. The module 900 with combined feed compartment 970 and permeate compartment 980 operates in SPF mode as described above in conjunction with FIG. 2.

The length of the channel 974, in one example, is approximately 5 times the length of the module 900 by virtue of the multiple twists-and-turns of the flow channel. Furthermore, channel width 979 diminishes by approximately a factor of ten from the inlet to the outlet end of the channel 974. The thickness and porosity of the feed spacer 971 affect the void volume of the channel 974 and in one embodiment is such that the specific membrane area of the flow channel is greater than about 40 cm$^{-1}$, in other embodiments greater than about 50 cm$^{-1}$, and in other embodiments greater than about 130 cm$^{-1}$. Other types of membranes (flat-sheet, hollow fiber, monoliths) can be used to construct a module similar to module 900. However, construction of such an element is facilitated by the use of flat-sheet membranes, where a reduction in cross-sectional area can more readily be obtained by reducing the width of the rectangular channels along the flow path.

Figure 10A:
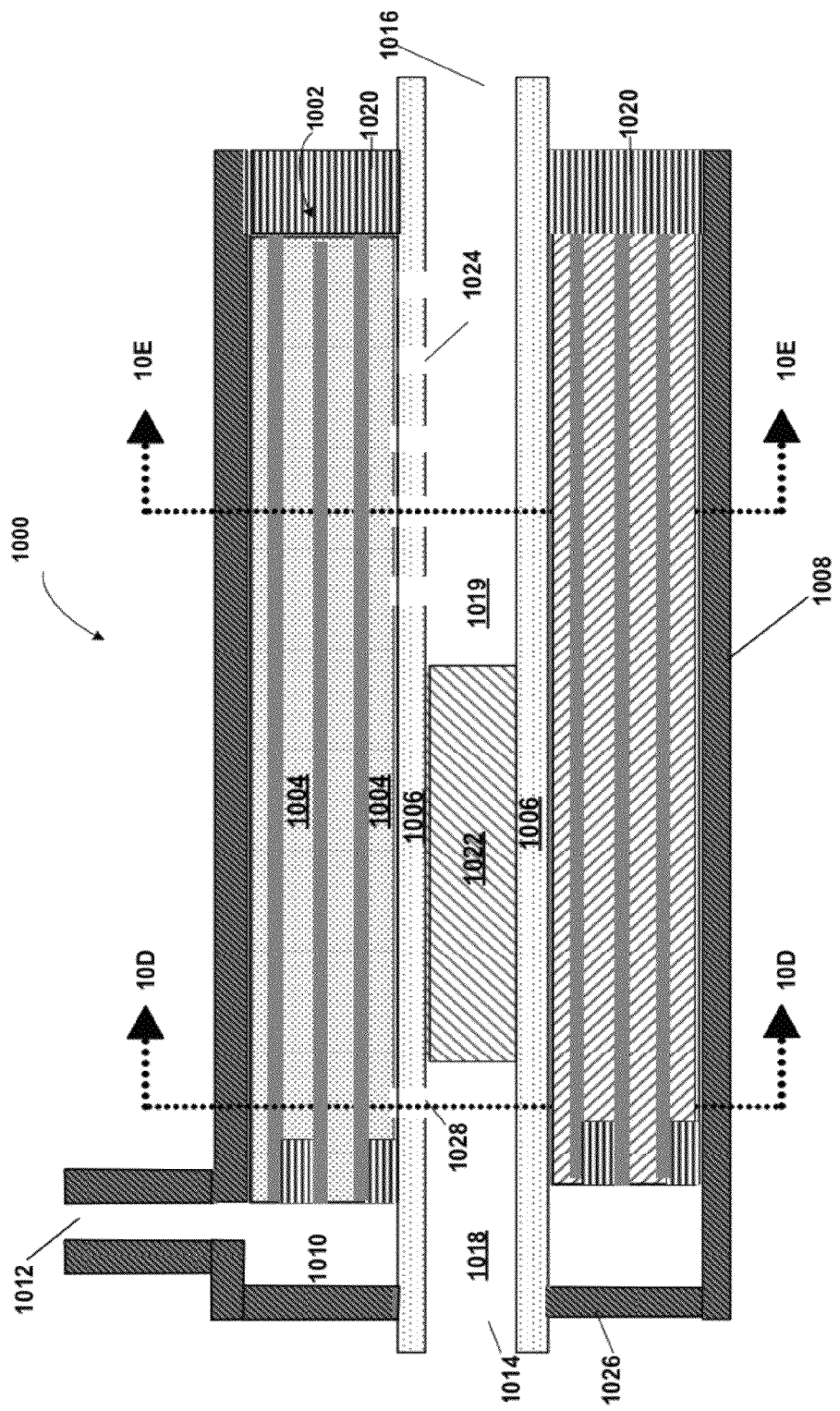
FIG. 10A is a schematic diagram of a single-leaf spirally-wound module according to the invention.
Figure 10B:
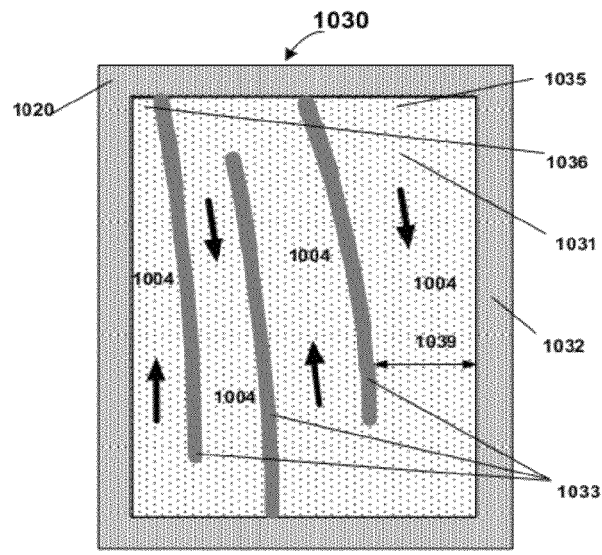
FIGS. 10B, 10C, 10D and 10E show multiple views of the spiral module of FIG. 10A including rectangular channels having decreasing cross-sectional area along the flow path.
Figure 10C:
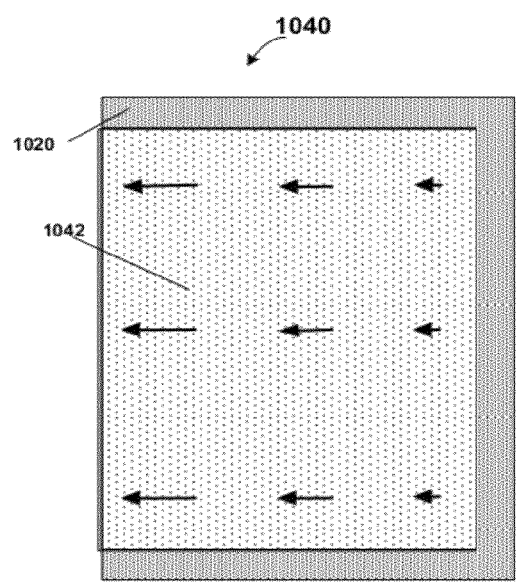
Figure 10D:
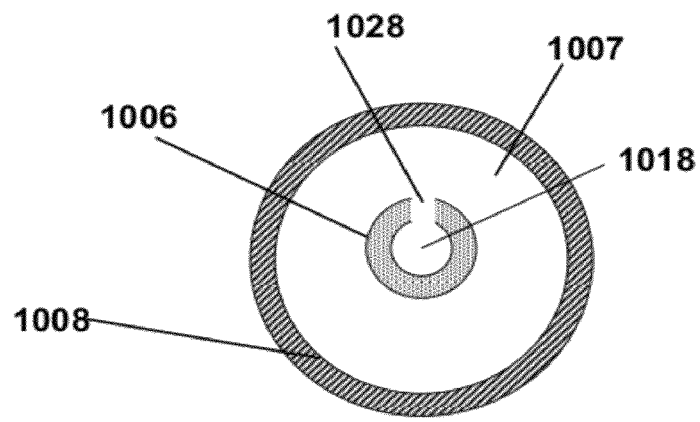
Figure 10E:
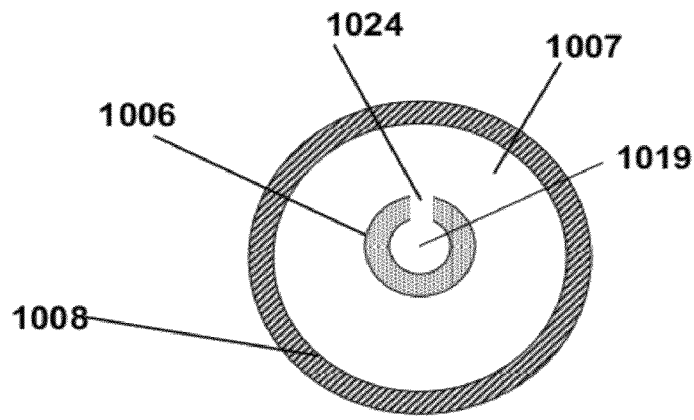

Referring to FIGS. 10A-10E, a spiral-wound separation module 1000 for the filtration of liquids, having similar channel features as module 900 of FIG. 9A, includes a spirally-wound membrane element 1002 coiled around a center tube 1006. The spiral element 1002 is formed by stacking a membrane (not shown), a feed compartment 1030, another membrane (not shown) and a permeate compartment 1040, and then winding this four-layer laminate around center tube 1006. In other words, one end of the center tube 1006 comprises primary and secondary flow passages 1019 and 1024, respectively, for the feed stream, whereas the other end comprises primary and secondary flow passages 1018 and 1028, respectively, for the retentate stream. The spiral-wound module 1000 further includes a tubular shell 1008 forming a cylindrical housing with a feed port 1016 on one end, a retentate port 1014 on the opposite end, and a permeate port 1012 on one side of tubular shell 1008. The center tube 1006 forms a coaxial retentate primary flow passage 1018 fluidly coupled to a secondary flow passage 1028 and forms a feed primary flow passage 1019 fluidly coupled to secondary flow passages 1024. The feed primary flow passage 1019 is disposed opposite the retentate primary flow passage 1018 with the plug 1022 interposed between passages 1018 and 1019. The spiral-wound module 1000 further includes a permeate collector 1010 fluidly coupled to the permeate port 1012 disposed in the tubular shell 1008. The tubular shell 1008 further includes seal 1020 disposed adjacent the feed port 1016 and an inlet end of the spiral element 1002 and end cap 1026 disposed adjacent the retentate port 1014. In an alternate embodiment, the location and orientation of the feed port 1016, retentate port 1014 and permeate port 1012 can be different according to the needs of the application. For example, the permeate collector 1010 could be located on the same end as the feed port 1016 by changing the location of the seals 1020 in the permeate compartment 1040 as shown in FIG. 10C. In another alternative embodiment, ports 1012, 1014 and 1016 can be located on the same end of the spiral-wound module 1000 which adds flexibility in designing separation systems utilizing these spiral-wound modules 1000 by placing all ports on the same end of the module. Referring again to FIG. 10B, the feed compartment 1030 comprises a feed spacer 1031 and the seal 1020. Ribs 1033 are embedded into the feed spacer 1031 forming a channel 1004 having an inlet end, an outlet end and a width 1039 which diminishes along the length of channel 1004. Referring to FIG. 10C, the permeate compartment 1040 includes a permeate spacer 1042 and the seal 1020.

In operation, a feed stream is introduced into the feed compartment 1030 through the plurality of secondary flow passages 1024, fed in turn by feed primary flow passage 1019 coupled to the feed port 1016. Secondary flow passages 1024 introduce the feed stream into the channel 1004, inducing tangential flow in the channel 1004. The tangential velocity of the liquid within the channel 1004, represented by arrows in FIG. 10B, remains substantially constant along the channel length by virtue of the diminishing channel width 1039. Retentate exits the channel 1004 through secondary flow passage 1028, which in turn fluidly connects into the retentate primary flow passage 1018, coupled to the retentate port 1014. In this embodiment, the length of the channel 1004 is approximately four times the length of the feed compartment 1030 by virtue of the multiple twists-and-turns of the channel 1004. Furthermore, channel width 1039 diminishes by approximately a factor of eight from the inlet end to the outlet end of channel 1004. The thickness and porosity of the feed spacer 1031 is selected to provide a specific membrane area of the channel 1004 greater than about 40 cm$^{-1}$, in other embodiments greater than about 80 cm$^{-1}$, and in other embodiments greater than about 50 cm$^{-1}$. In another embodiment, the specific membrane area of the channel 1004 is greater than about 130 cm$^{-1}$ and the width of the channel 1004 decreases by a factor greater than about two from the inlet of the channel 1004 to the outlet of the channel 1004.

A permeate stream enters the permeate compartment 1040 by permeating through the membrane separating the feed compartment 1030 from the permeate compartment 1040. Permeate velocity increases along the flow path as indicated by arrows, flowing to the end of the permeate compartment where the permeate is collected in the permeate collector 1010. The properties of the permeate spacer 1042 can be selected, for example, to minimize hold-up volume, provide adequate support to the membrane and to prevent excessive pressure differentials within the permeate compartment 1040. In an alternative embodiment, a retentate port can be provided on the same end as the feed port.

An alternate embodiment similar to spiral-wound separation module 1000 shown in FIGS. 10A-E can be used to provide an internally-staged SPF module suitable for diafiltration. In this embodiment, multiple spiral cartridges similar to those described in above, are serially coupled, each spiral element forming one stage of the multi-stage module. Diafiltrate is then introduced and distributed to the inlet of each stage by means of internal or external passageways. The diafiltration passageways are embedded within the center tube 1006 by means of a coaxial passageway concentric to the primary feed and retentate passageways 1019 and 1018, respectively. In still another embodiment conventional spiral cartridges (not shown) instead of module 1000 are serially coupled to form a multi-stage module. In this case the center tube carries the permeate instead of carrying the feed and retentate. The diafiltrate is introduced and distributed to the inlet of each stage by means of internal or external passageways.

Figure 11A:
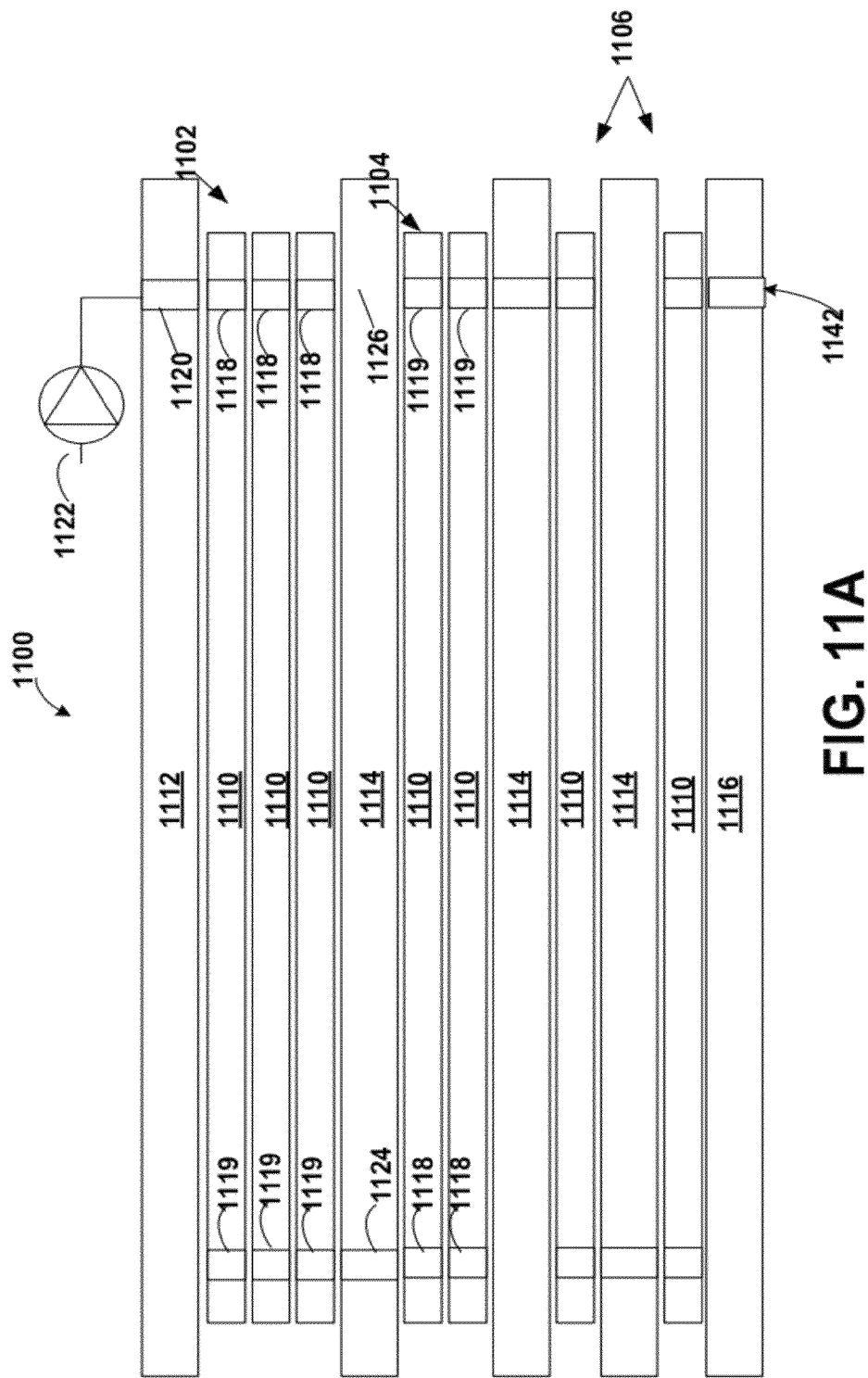
FIG. 11A is a schematic diagram of an exemplary staging plate and cassette system according to the invention.

Referring now to FIG. 11A, a single pass filter system 1100 includes a plurality of stages 1102, 1104, and 1106, each stage having one or more cassettes 1110, a top plate 1112, a plurality of staging plates 1114 and a bottom plate 1116 in a stacked configuration. The cassettes 1110 each have at least one channel (not shown) fluidly coupled to a feed manifold 1118, a retentate manifold 1119 and at least one permeate channel (not shown). The top plate 1112 includes a feed port 1120 in fluid communication with a feed pump 1122. The staging plate 1114 includes a pass through port 1124 disposed to align with corresponding feed manifolds 1118 and retentate manifolds 1119. The bottom plate 1116 includes a retentate port 1142 in fluid communication with the retentate manifold of the adjacent cassette 1110. The staging plates 1114 are disposed to fluidly couple at least one retentate manifold from the upstream stage to the feed manifold of the adjacent stage downstream thereby serializing the retentate flow while leaving the permeate channels coupled in parallel. In other embodiments the permeate from each stage 1102-1106 is separately collected by means of a permeate distributor. In one embodiment the cassettes 1110 are conventional cassettes, for example GE 30K polysulfone lab cassette Part #UFELA0030001ST; Pall Omega 10KD T2 0.2 sq ft Centramate™ cassette; Millipore Pellicon 3 MicroCassette 10K regenerated cellulose, Catalog No. P3C 010C00. Although conventional cassettes can be used, separation performance is enhanced by the use of cassettes having higher specific membrane areas. In one embodiment, the system 1100 has a 3,2,1,1 configuration (i.e., a stack including the top plate 1112, three cassettes 1110, staging plate 1114, two cassettes 1110, staging plate 1114, one cassette 1110, staging plate 1114, one cassette 1110, and the bottom plate 1116).

In operation, the system 1100 runs as a single-pass process similar to the process described in FIG. 2, and staging improves the performance of the separation process, including a flux enhancement. In each stage, for example stage 1102, the feed manifolds 1118 of each cassette 1110 are fluidly coupled in parallel, however the staging plate 1114 blocks the feed stream at point 1126 from entering the next stage 1104 as would occur in a conventional plate and frame assembly thereby serializing the flow through the retentate manifolds 1119, the pass through port 1124 in the staging plate 1114 and the feed manifolds 1118 in the cassettes 1110 comprising the next stage 1104. In one embodiment, the specific feed flow rate for this staged system 1100 is about 112 lmh and the dimensionless length for the system is about 5,200. Here the SPF operation with the low specific feed flow rate is enabled by the serialization of the channels of the cassettes 1110.

From the foregoing, it can be appreciated that the modules, systems and methods of the invention facilitate SPF operation. The invention will be further described in the following example, which is not exhaustive and does not limit the scope of the invention described in the claims.

EXAMPLE 1

In this example, a 1% solution of Bovine Serum Albumin in a pH 7.6 phosphate diafiltrate was concentrated using cassettes comprising membrane with a MWCO of 10,000 Daltons arranged in a system similar to system 1100. The system included four stages connected in series using staging plates similar to staging plate 1114; the feed to an adjacent following stage being the retentate of the adjacent preceding stage. The first stage included four cassettes in parallel, the second had three cassettes in parallel, the third stage had two cassettes in parallel and the fourth stage had a single cassette. Each cassette had a $\sigma_c$ value of about 70 cm$^{-1}$. The $\lambda_{stage}$ values of the stages were about 1,300 and by using the staging plates the $\lambda_{system}$ value of the system was about 5,040. A peristaltic pump supplied feed solution to the first stage and a valve on the outlet of the last stage controlled the retentate flow rate. In a series of experiments conversions of between 85% and 90% were achieved with fluxes of between 74 to 127 lmh corresponding to specific feed rates in the range of 81 to 140 lmh. These tests showed that it is possible to achieve high conversions, in a single pass, without needing to recirculate retentate to the feed. The combination of a high $\sigma_c$ value in combination with a maximum $\lambda_{stage}$ value and a minimum value of $\lambda_{system}$ makes possible the concentration or diafiltration of solutions at attractive fluxes and low diafiltration requirements when used for diafiltration.

Figure 11B:
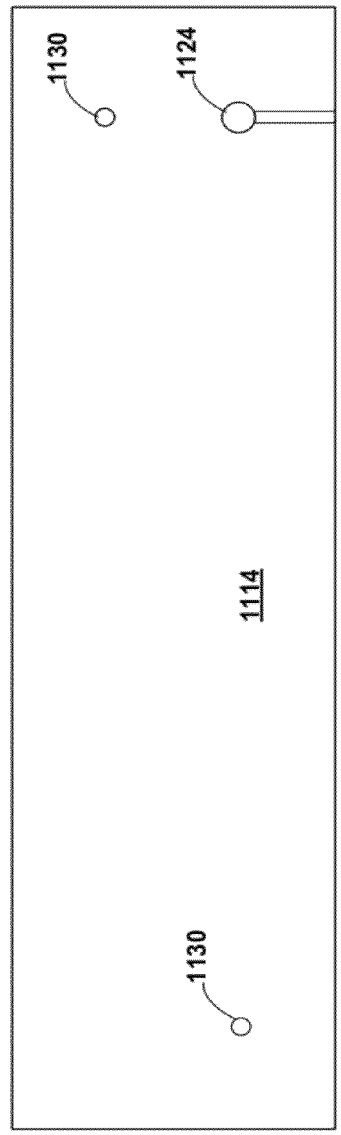
FIG. 11B is a schematic diagram of a staging plate assembly using the components of FIG. 11A.
Figure 11C:
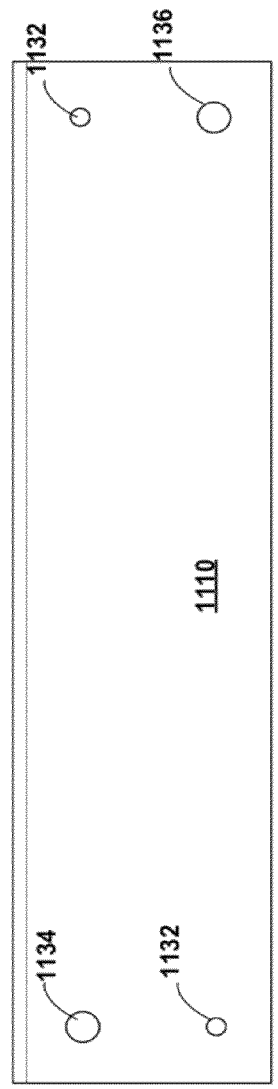
FIG. 11C is a schematic diagram of conventional cassette as used in the system of FIG. 11A.

Referring now to FIGS. 11B and 11C, in which like elements are provided having like reference designations as in FIG. 11A, the staging plate 1114 includes a pass through port 1124 and a plurality of permeate ports 1130. The standard lab-scale cassette 1110 includes a pair of feed passages 1134 and 1136 and a pair of permeate passages 1132. When the cassette 1110 is stacked adjacent the staging plate 1114, feed passage 1134 is blocked by the staging plate 1114 which in operation essentially serializes the flow by forcing the retentate from the cassettes 1110 as well as any additional cassettes 1110 stacked adjacent the cassette 1110 adjacent the staging plate 1114 to provide the feed to the following adjacent stage. The resulting flow path, represented by arrows, is shown in FIG. 11D.

The embodiment represented in FIG. 11D is an internally-staged module with a 3-2-1-1 configuration. This module effectively comprises three stages, the first and second stages having $\lambda_{stage}$ values of 1300, while the third stage has a $\lambda_{stage}$ value of 2600, resulting in a $\lambda_{system}$ value for the module of 5200. The last two cassettes 1110 and staging plate 1114 comprise a single stage 1106 because there is no physical property change and no stage transition between the two cassettes 1110 in stage 1106. In alternative embodiment similar to system 1100 of FIG. 11D, the system also has a 3-2-1-1 configuration and additionally includes a permeate distributor to control the permeate pressure in each stage at a predetermined value. In contrast to system 1100 this system has 4 stages, each stage having the same value of $\lambda_{stage}$ of about 1300.

Referring now to FIG. 11D, in which like elements are provided having like reference designations as in FIGS. 11A, 11B and 11C, the flow paths through system 1100 are shown. The feed stream flows through and enters the feed port 1120 of the top plate 1112. The feed stream then flows in parallel into the feed manifold 1118 of each cassette 1110. The feed stream then flows across the channel as indicated by arrow 1144 and flows into the retentate manifold 1119 of each cassette 1110 as indicated by flow arrows 1146. The retentate output of stage one then flows through the pass through port 1124 of the staging plate 1114 into the cassettes 1110 of stage two as indicated by flow arrows 1148. Note that at section 1126 of the staging plate 1114 the normally parallel feed flow is blocked. The flow continues in a similar manner until the flow reaches the bottom plate 1116 and the retentate exits through the retentate port 1142 as indicated by flow arrow 1166.

A comparison between a conventional batch TFF concentration process and the SPF concentration process obtained in a system similar to system 1100 is listed in Table 2. It is noted that although the process time is equivalent, the capital costs and the holdup volumes are much larger for the conventional batch system.

TABLE 2

Batch vs. SPF Concentration System
12,000 liters concentrated to 500 liters

| | BATCH | SPF |
|---|---|---|
| Membrane Area [m$^2$] | 40 | 40 |
| Process Time [hr] | 4 | 4 |
| Pump Capacity [L/hr] | 14,000 | 3,000 |
| Recirculation Loop | YES | Not Needed |
| No. of Pump Passes | 10-100 | 1 |
| Relative Holdup Volume | 4 | 1 |
| Relative Capital Cost | 2.5 | 1 |
| Feed Tank | YES | Not Needed |
| Heat Exchanger | Possibly Needed | Not Needed |

Figure 12:
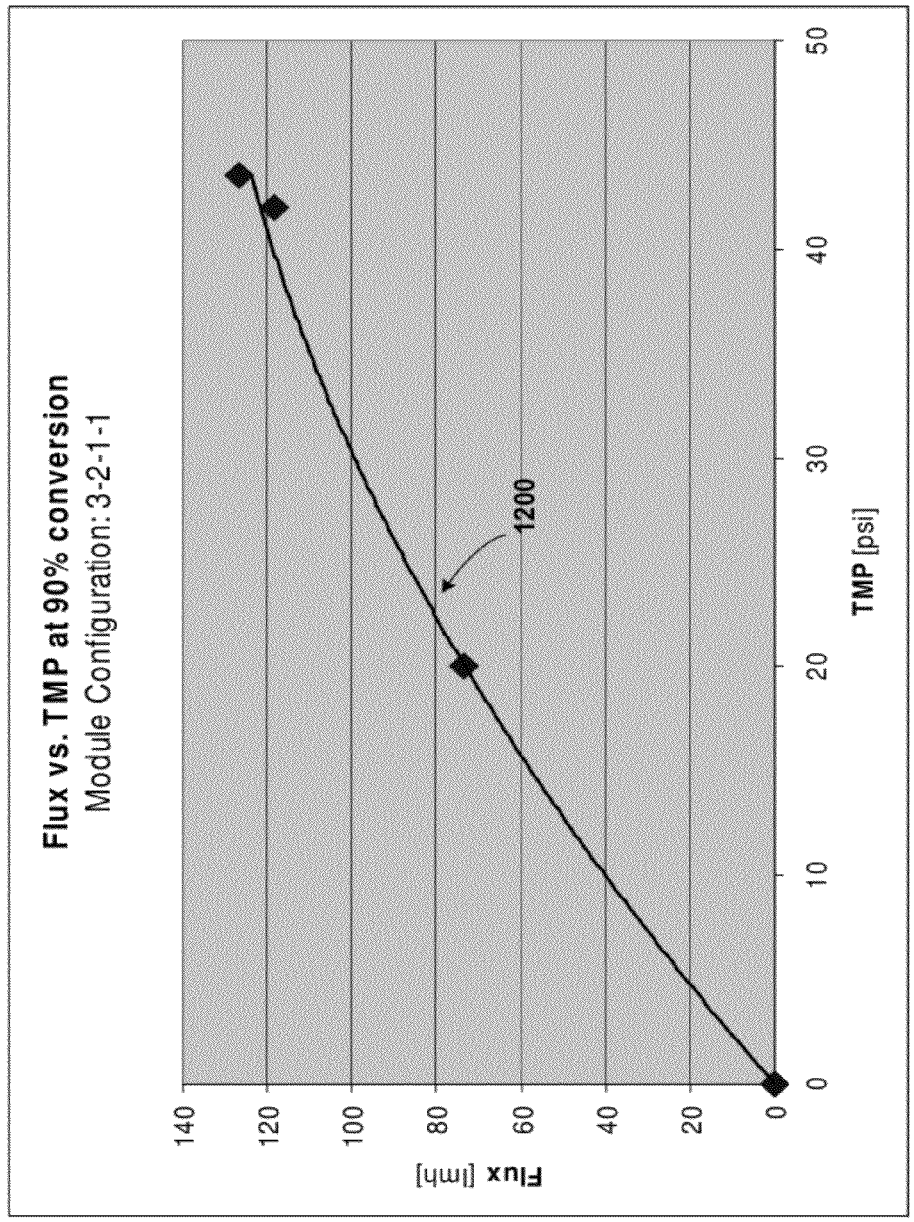
FIG. 12 is an exemplary flux profile for a concentration module similar to the module of FIG. 11A.

Now referring to FIG. 12, a graph of flux as a function of TMP for system 1100 of FIG. 11A is shown. Curve 1200 represents the average flux as a function of TMP measured with conversion set and maintained at 90%. The average flux was calculated by measuring the total permeation rate (i.e., for the four stages) and dividing it by the total membrane area for the stages of system 1100. The flux vs. TMP response is quite different from that obtained with conventional TFF. Conventional TFF is sometimes characterized by a maximum flux or a plateau that occurs at high values of TMP. In contrast, no such plateau is present in constant conversion SPF mode because an increase in TMP simultaneously results in an increase in cross-flow rate, which in turn increases the permeation capability of the module. Unlike some conventional TFF concentration processes, which attempt to maintain a constant TMP throughout the flow path, the improved SPF concentration process operates with a monotonically decreasing TMP (e.g., the highest TMP at the inlet and a decreasing TMP along the flow path).

Figure 13A:
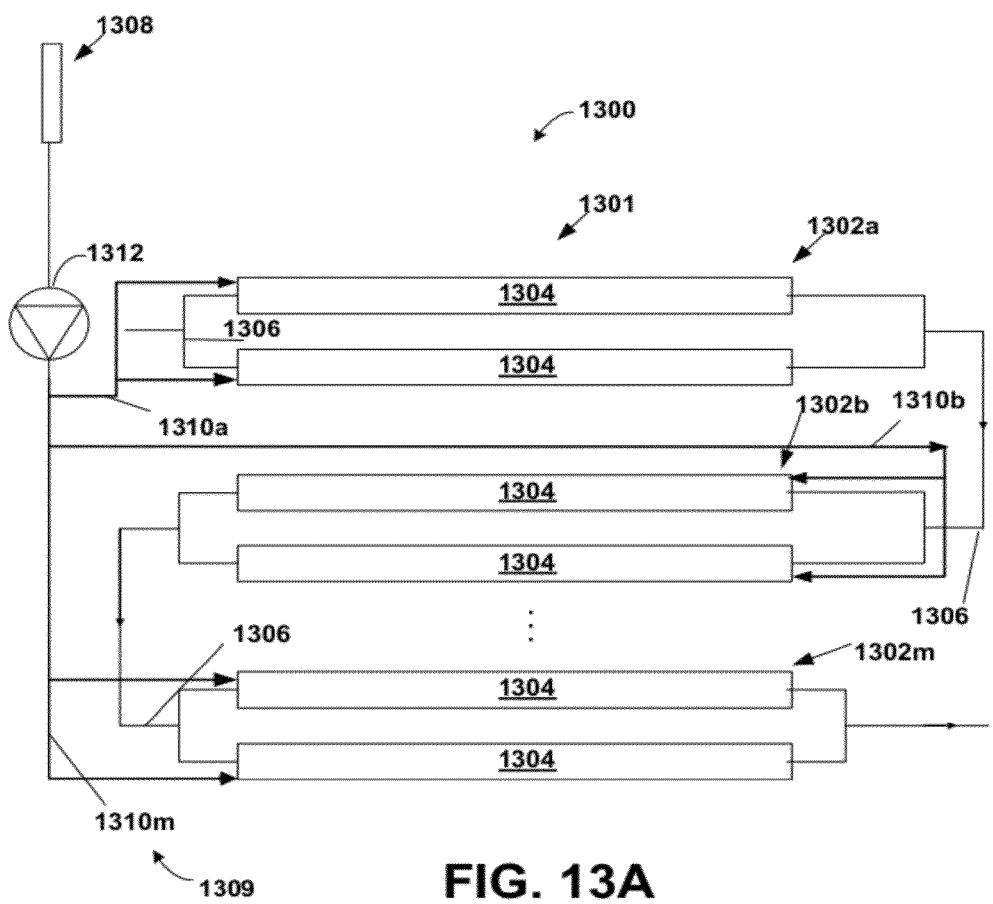
FIG. 13A is a schematic diagram of an internally staged diafiltration system suitable for diafiltration according to the invention.

Now referring to FIG. 13A, an internally-staged diafiltration system 1300 according to the invention includes diafiltration module 1301 having a plurality of stages 1302a-1302m (collectively referred to as stages 1302), each stage having a plurality of channels 1304. The stages 1302 are disposed such that each stage 1302 is in fluid communication with each adjacent stage 1302 preceding it and is in fluid communication with each adjacent stage 1302 that follows it. Each of the channels 1304 includes a filtration membrane (not shown). As described above, each of the channels 1304 has a length, a membrane area, a void volume, a specific membrane area expressed as a ratio of the membrane area to the void volume, and a dimensionless length expressed as a product of the channel length and the specific membrane area. The system 1300 further includes a diafiltrate source 1308 fluidly coupled to a pressure source 1312 which is fluidly coupled to at least one diafiltration distributor 1309 having a network of diafiltration flow passages 1310a-1310m with predetermined hydraulic resistances which are in turn fluidly coupled to corresponding manifolds 1306 which are fluidly coupled to corresponding stages 1302. It is understood that the number of channels 1304 in each stage 1302 could differ, the channels 1304 could be identical or could have different properties, each stage 1302 does not require connection to one of the diafiltration flow passages 1310, and that not every stage 1302 receives diafiltrate.

In operation, diafiltrate is introduced under pressure provided by the pressure source 1312 through the diafiltration flow passages 1310 of the diafiltration distributor 1309 and the manifolds 1306 into the channels 1304 of the stages 1302. The diafiltration process is operated as an SPF process similar to the process described in FIG. 2. In one embodiment the stages 1302 and channels 1304 are substantially identical and the pressure source 1312 is an external pump. SPF operation is provided in this embodiment by selecting a purification factor for the process and adjusting at least one of the diafiltration flow rate, the feed flow rate and the retentate flow rate until the desired purification is obtained. Table 3 shows a comparison between a conventional diafiltration process and a diafiltration process using a system similar to system 1300 operating in an SPF mode. Additional details of the introduction of the diafiltrate are described in conjunction with FIG. 13B. Generally the diafiltration stages 1302 are similar and correspondingly equal diafiltration rates are used for each stage 1302. However, in other embodiments combining concentration and diafiltration, stages may have different membrane areas, different numbers of channels (e.g., a 4-3-2-1 configuration) and different values of $\sigma_c$, and the diafiltrate may be supplied to selected stages at different rates.

Figure 13B:
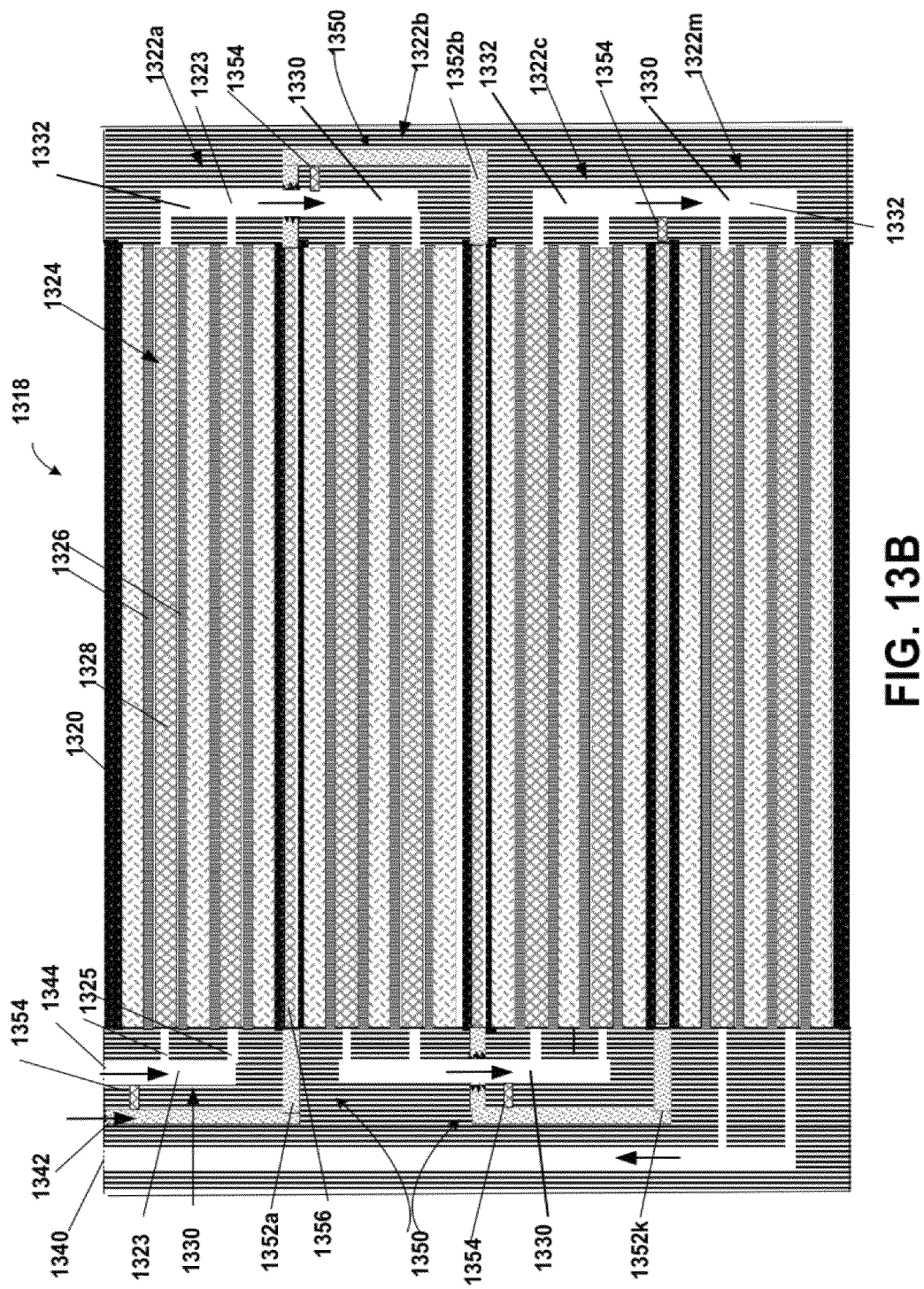
FIG. 13B is a schematic diagram of one embodiment of the system of FIG. 13A, including diafiltration hydraulic distributors.

Referring to FIG. 13B, an internally-staged diafiltration module 1318 similar to the diafiltration module 1301 in FIG. 13A includes a plurality of stages 1322a-1322m (collectively referred to as stages 1322), each stage having a plurality of channels 1324. Each channel 1324 comprises a membrane 1326 disposed adjacent to a feed spacer 1328 which provides support for the membrane 1326. In one embodiment, the channels 1324 have $\sigma_c$ values of greater than about 40 cm$^{-1}$ and $\lambda_{stage}$ values of less than about 6,000. In this embodiment, the $\lambda_{system}$ (i.e., the of the module) for module 1318 is greater than 2,000. The module 1318 further includes feed manifolds 1330 and retentate manifold 1332 fluidly coupled to the channels 1324 of the each stage 1322. Both the feed manifold 1330 and the retentate manifold 1332 have a primary flow passage 1323 and secondary flow passages 1325. The stages 1322 are disposed such that each stage is in fluid communication with each adjacent stage 1322 preceding it and is in fluid communication with each adjacent stage 1322 that follows it. The module 1318 further includes inlet port 1344 fluidly coupled to the feed manifold 1330 of stage 1322a and a retentate outlet port 1340 fluidly coupled to the last stage 1322m. The module 1318 further includes a diafiltration distributor 1350 which comprises a plurality of diafiltration flow passages 1352a-1352k (collectively referred to as diafiltration flow passages 1352) and a diafiltrate inlet port 1342 fluidly coupled to the diafiltration flow passage 1352a. The diafiltration distributor 1350 further comprises a plurality of diafiltration passageways 1354 fluidly coupling respective diafiltration flow passages 1352 to the corresponding feed manifolds 1330. The diafiltration flow passages 1352 include diafiltrate spacers 1356 having predetermined hydraulic resistances so as to introduce diafiltrate at a predetermined flow rate at a selected pressure into corresponding feed manifolds 1330.

In one embodiment, the diafiltration flow passages 1352 having a predetermined hydraulic resistance are formed with the spacers 1356 configured and stacked by means similar to those used for making the channels 1324. The hydraulic resistance of the diafiltration flow passage 1352 is a function of (a) the hydraulic diameter of the spacer 1356, (b) the width of the channel formed by the spacer 1356, and (c) the effective path length of the spacer 1356. The determination of the hydraulic resistance values is described in more detail in conjunction with FIGS. 14A, 14B and 15.

In operation, a feed stream flows through primary flow passage 1323 in the feed manifold 1330 of the first stage 1322a, which in turn feeds secondary flow passages 1325 which feeds channels 1324 of first stage 1322a. The retentate from the channels 1324 are collected through secondary flow passages 1325, which feed primary flow passage 1323 of the retentate manifold 1332 of the first stage 1322a. Diafiltration solution is introduced into diafiltrate flow distributor 1350 through the diafiltrate inlet port 1342 and into the diafiltration flow passage 1352a. Diafiltration distributor 1350 allows a predetermined fraction of the diafiltration stream to enter the feed manifold 1330 at a point upstream of secondary flow passages 1325 to promote the mixing of the diafiltrate with the feed stream before the diafiltrate enters channels 1324. The hydraulic resistance of the diafiltrate spacer 1356 in addition to the external pressure source controls the hydraulic pressure of the diafiltrate stream along the diafiltration flow passages 1352 in order to control the introduction of diafiltrate into the feed manifold 1330 of each stage 1322. In certain embodiments the diafiltration flow passages 1352 have differing hydraulic resistances.

In alternative embodiments, the inlet port 1344 and the retentate outlet port 1340 can be located in different places in the housing 1320 according the application requirements. In one embodiment, the module 1318 has ports 1340, 1342 and 1344 located on one face of the module, to conveniently facilitate the installation and replacement of each module in a separation system (not shown). The routing and location of the primary and secondary flow passages will be dictated by manufacturing considerations known to those skilled in the art. Limiting the value of $\lambda_{stage}$ results in the use of a larger number of stages for a given degree of impurity removal results in a lower consumption of diafiltrate. In one embodiment, the module 1318 includes an optional diafiltration spacer (not shown) disposed in the diafiltration flow passage 1352 providing a hydraulic resistance predetermined to further control the flow rate of a diafiltrate along the diafiltration flow passage 1352. A comparison between a conventional batch TFF diafiltration process and the SPF diafiltration process obtained using a system similar to system 1300 is listed in Table 3.

TABLE 3

Batch vs. SPF Diafiltration System - 1,000 liters diafiltrated 100-fold

| | BATCH | SPF |
|---|---|---|
| Membrane Area [$m^2$] | 15 | 15 |
| Process Time [hr] | 4 | 4 |
| Pump Capacity [L/hr] | 5,300 | 250 |
| Recirculation Loop | Needed | Not Needed |
| No. of Pump Passes | 20 or more | 1 |
| Diafiltrate Volume [L] | 4600 | 4600 |
| Diafiltrate Volume with counter flow of diafiltrate | Not practical | 3,800 |
| Internal Stages | 1 | 10 |
| Relative Holdup Volume | 4 | 1 |
| Relative Capital Cost | 2.5 | 1 |
| Feed Tank | Needed | Not Needed |
| Heat Exchanger | Needed | Not Needed |

The effect of the diafiltration process is to wash (i.e., purify) the retentate stream solution in an in-line fashion along the flow path. The channels in the four stages 1322 are included within a single internally-staged module. For example, if each stage provides 80% conversion, and one part of the retentate from each stage is diluted with about four parts of diafiltrate, the internally-staged module 1320 will remove low molecular weight impurities by almost 625-fold, a purification equivalent to a "6.44-volume" batch diafiltration process.

In the staged diafiltration module using a common source of diafiltrate, it is possible to distribute the diafiltrate to selected stages 1322 by providing the passive distributor 1350 including the network of diafiltration flow passages 1354 interposed between the common source of diafiltrate and the inlet of each selected stage 1322. The diafiltration flow passages 1354 of the diafiltration distributor 1350 have hydraulic resistances that result in a specified flow rate of diafiltrate to each selected stage 1322. Since the pressure at the inlet of each selected stage 1322 decreases in the direction of the feed flow, the hydraulic resistance of the each of the diafiltration flow passages 1354 needs to increase from stage to stage in the direction of flow in order to deliver a desired amount of diafiltrate in each stage 1322. For any given diafiltration pressure to the staged array and a given retentate pressure at the retentate of the staged array it is possible to specify the hydraulic resistance of each diafiltration flow passage 1354 in order to achieve a desired diafiltration rate to any selected stage 1322 even if the diafiltrate source is at a pressure different from the pressure at the inlet to one of the selected stages 1322.

In one embodiment, the internally-staged diafiltration module 1318 receives diafiltrate at a feed flow rate to the staged array equal to the retentate flow rate from the module 1318. Operating with this embodiment, the diafiltration flow rate to each stage should preferably be the same. This equality of diafiltrate flow rate can be arranged by providing suitable hydraulic resistances for each diafiltration flow passage 1352 of the distributor 1350, based on a known pressure at the inlet of each stage 1322. Should there be a deviation in the value of the pressures at the feed manifold 1330 of the stage 1322, the diafiltration flow rate to that stage 1322 may become greater or less than the diafiltration flow rate to other stages. This is an undesirable situation because unequal flow rates of diafiltrate to stages 1322 can result in an increase in the total volume of diafiltrate to achieve a given degree of impurity removal, which the diafiltration process is designed to achieve and can also result in overconcentration of the desired solute at one of the stages within the module. This undesirable effect can be mitigated when using a diafiltration distributor comprising a parallel network of resistors by supplying the diafiltrate at source pressure considerably higher than the pressures prevailing in the staged module 1318. This results in the distribution of diafiltrate among the stages 1322 being less sensitive to possible variations in the stage inlet pressures. The hydraulic resistances of the individual distributors are arranged to provide the desired diafiltrate flow rate to each stage, based on the value of the pressure of the common diafiltrate source. In one embodiment the diafiltrate is supplied to corresponding stages at a source pressure greater than about one and one half times the feed pressure to module 1318 such that the effect of varying channel pressures on diafiltrate flow rate are reduced. In another embodiment the diafiltrate is supplied to corresponding stages at a source pressure of about 10 psi greater than the feed pressure to module 1318 such that the effect of varying channel pressures on diafiltrate flow rate are reduced.

Figure 15:
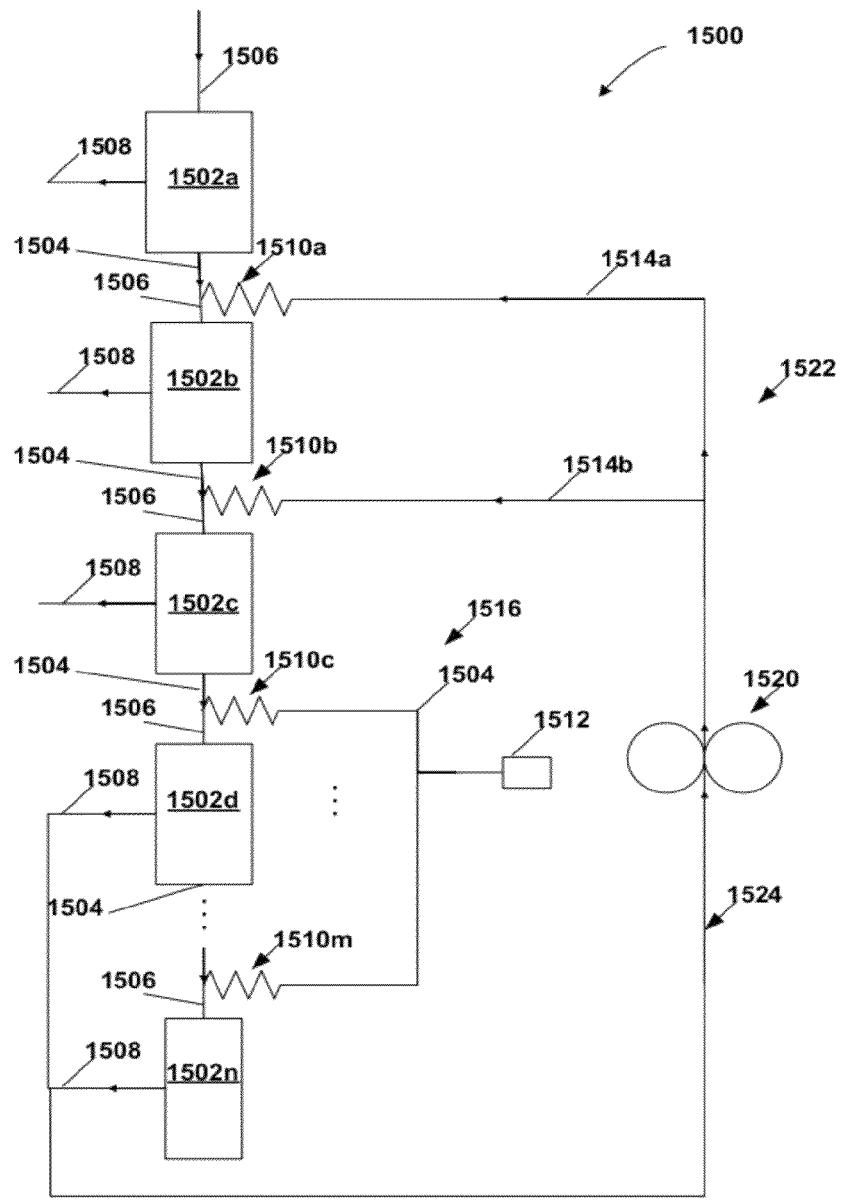
FIG. 15 is a schematic diagram of a counter current diafiltration module according to the invention showing the distributors as a parallel network of resistors coupled to a pump.
Figure 20:
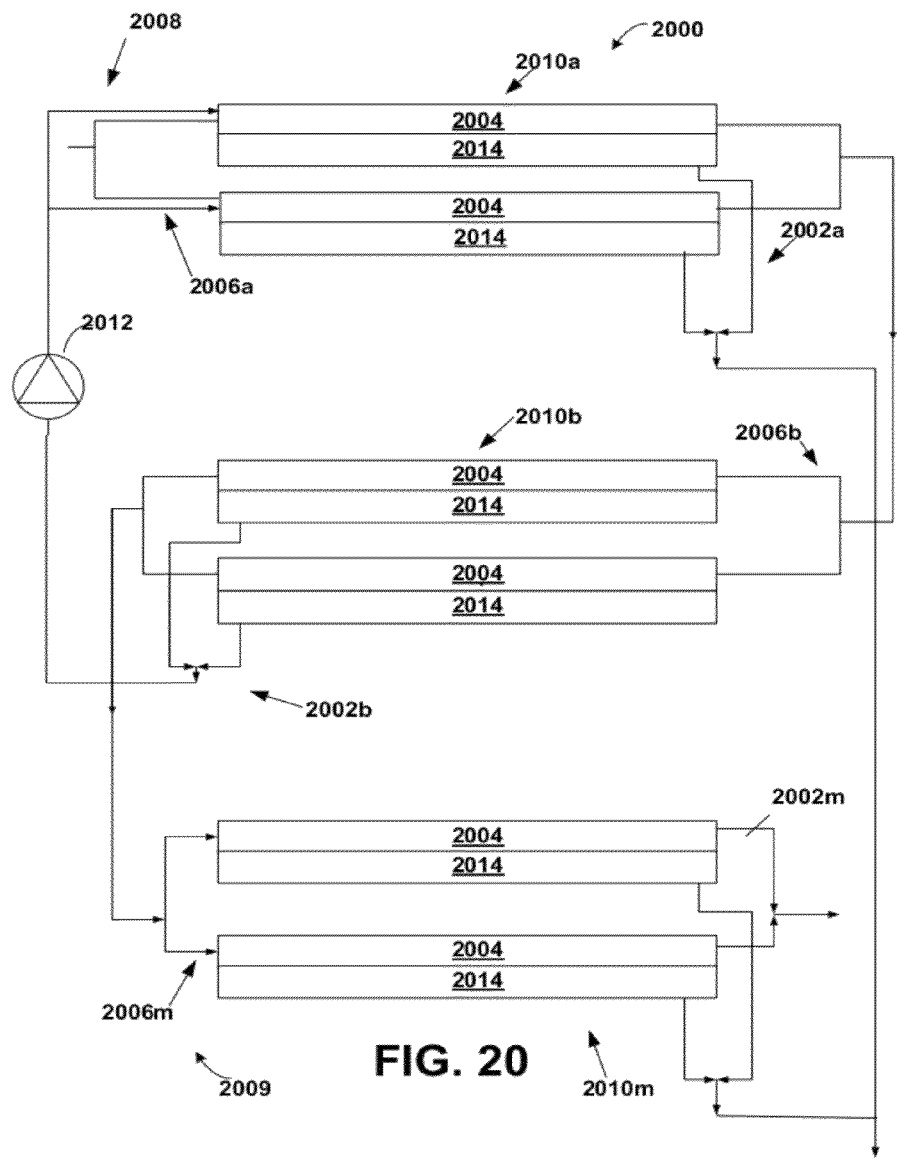
FIG. 20 is a schematic diagram of a staged module suitable for counter current diafiltration according to the invention.

It will also be appreciated that the diafiltration process can be operated in a counter current mode by fluidly coupling a permeate channel to at least one preceding flow channel. A counter current diafiltration module would be similar to module 1318 further including a diafiltration distributor but with a permeate compartment from at least one stage providing the source of diafiltrate to a preceding stage. A pump is needed to increase the pressure of the permeate to the pressure of said receiving flow channel as illustrated in FIGS. 15 and 20. The SPF diafiltration module with counter current diafiltration module generally reduces the quantity of fresh diafiltrate required for the process.

Figure 14A:
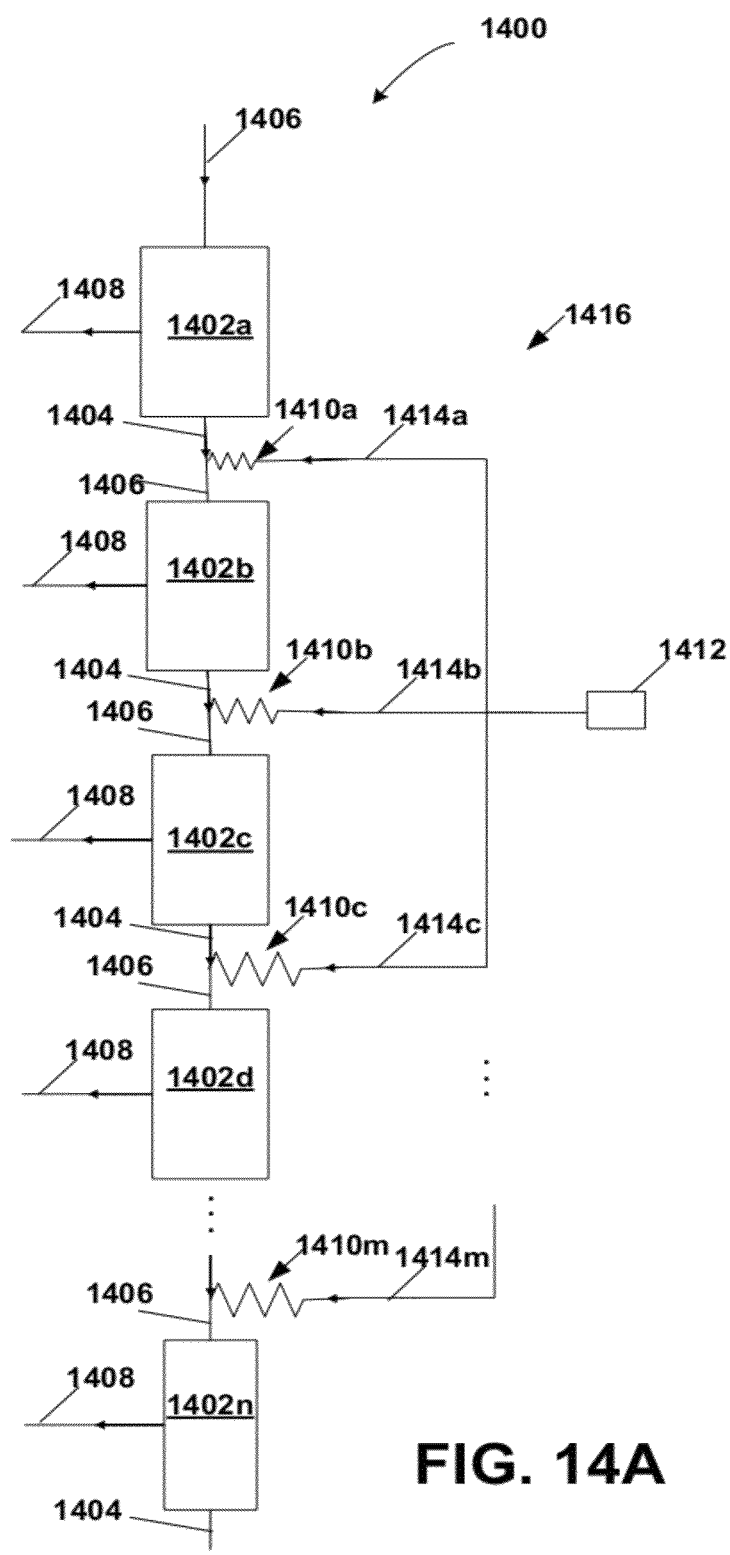
FIG. 14A is a schematic diagram of a diafiltration distributor similar to the distributor in the system of FIG. 13B implemented as a parallel resistance network of hydraulic resistors.
Figure 14B:
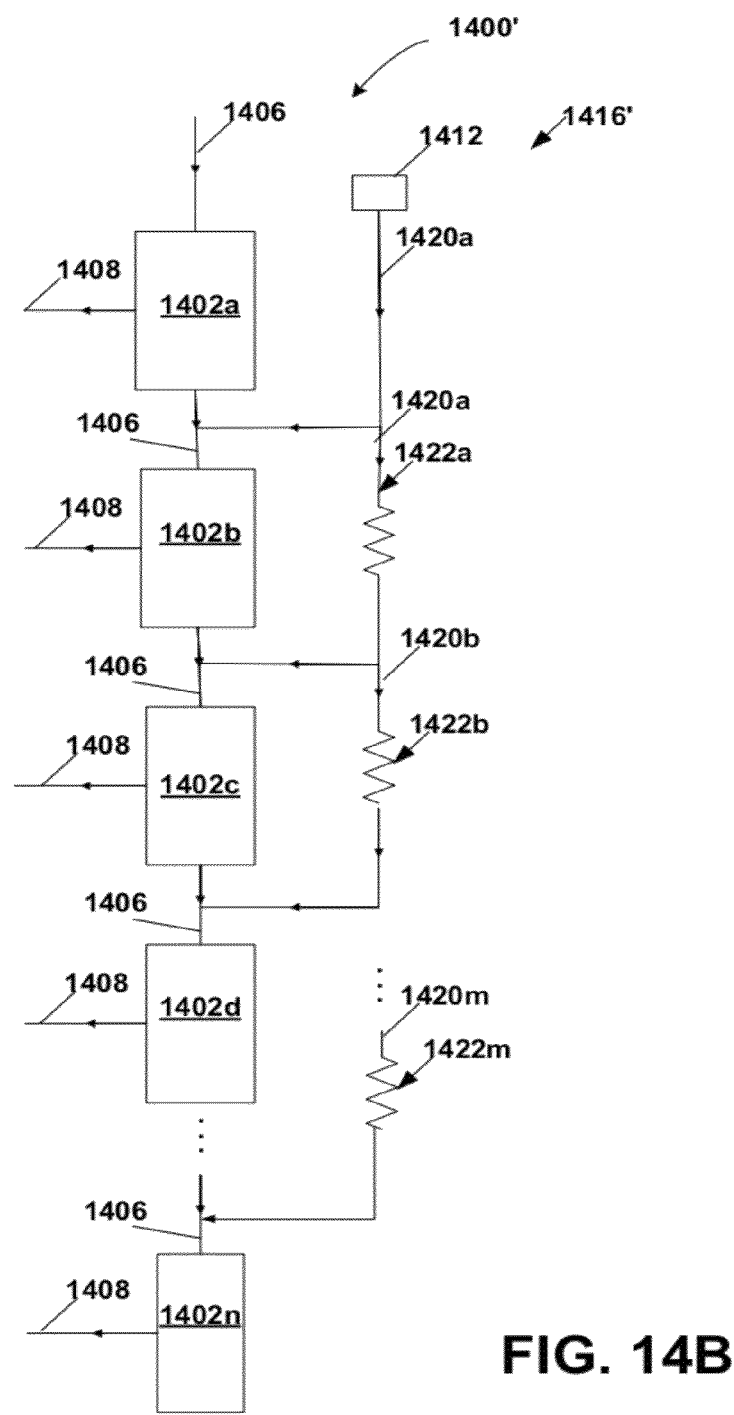
FIG. 14B is a schematic diagram of a diafiltration distributor similar to the distributor in the system of FIG. 13B implemented as a series resistance network of hydraulic resistors.
Figure 14C:
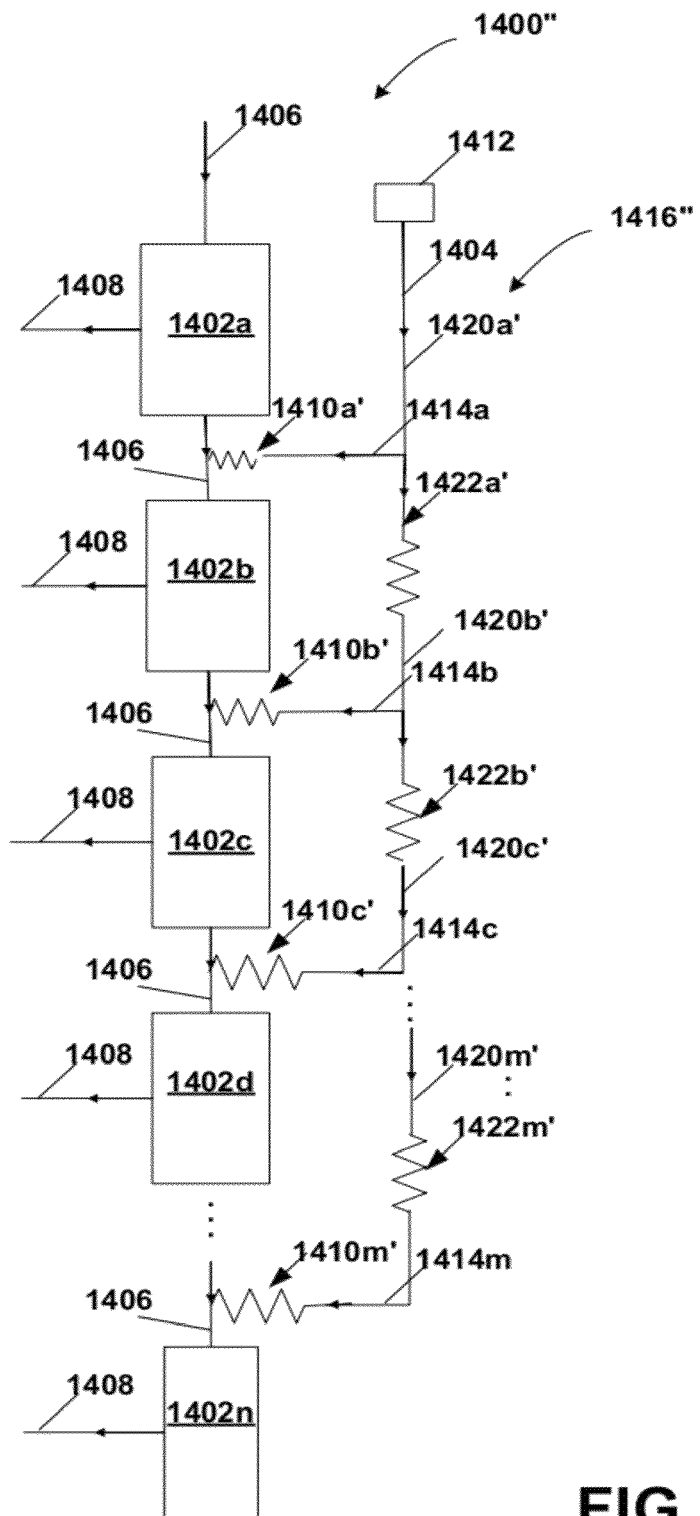
FIG. 14C is a schematic diagram of a diafiltration distributor similar to the distributor in the system of FIG. 13B implemented as a series-parallel resistance network of hydraulic resistors.

FIGS. 14A, 14B and 14C, in which like elements are provided having like reference designations throughout the several views, illustrate exemplary resistive models of the of the diafiltration distributor 1309 hydraulic resistances provided by the individual flow channels 1310 of FIG. 13A. Referring to FIG. 14A, an exemplary module 1400 with components shown as a resistive network includes a plurality of stages 1402a-1402n each having a retentate output 1404, a feed input 1406 and a permeate output 1408. The module 1400 further includes at least one diafiltration distributor 1416 having a plurality of diafiltration flow passages 1414a-1414m which are fluidly coupled to a pressurized diafiltrate source 1412. Resistances 1410a-1410m represent the predetermined hydraulic resistance of the corresponding diafiltration flow passages 1414 coupled in a parallel network and are used to control the flow rates of diafiltrate streams being fed to each stage receiving diafiltrate. The diafiltration flow passages 1414 fluidly couple the diafiltrate source 1412 to the corresponding feed input 1406 to each stage receiving diafiltrate.

The predetermined resistances of the diafiltration flow passages 1414 are based on the pressures prevailing in the feed to the various stages and the desired diafiltrate flow rate to each stage. A predetermined range of diafiltration supply pressures is selected to make the diafiltrate flow rate to each stage receiving diafiltrate insensitive to the variations in the feed pressures in those stages. The resistances of the diafiltration flow passages 1414 are formed physically, for example, by varying diameter and length of the diafiltration flow passages in an externally staged module or by providing channels having varying cross sections, by varying the hydraulic diameter of the diafiltration flow passages 1414, or by introducing orifices within the diafiltration flow passages 1414.

The resistive values are predetermined by modeling the performance of the system (e.g., numerically or using computer simulation) or can be determined empirically. In one embodiment values of the individual parallel resistances in module 1400 are chosen to add a substantially similar diafiltrate flow rate to each stage although the pressure at the inlet to the stage varies. Generally, larger values of hydraulic resistance are provided for downstream stages. In addition, supplying the diafiltrate at a substantially higher pressure than the feed pressures to the stages reduces the effect of varying channel pressures on diafiltration flow rates. In one embodiment the diafiltrate pressure is supplied to selected stages at a source pressure greater than about one and one half times the feed pressure to the module 1400 so the effect of varying feed pressures on diafiltrate flow rate is reduced. In another embodiment the diafiltrate pressure is supplied to selected stages at a source pressure of about 10 psi greater than the feed pressure to the module 1400.

Now referring to FIG. 14B, an exemplary module 1400' includes at least one diafiltration distributor 1416' having a plurality of diafiltration flow passages 1420a-1420m which are fluidly coupled to the pressurized diafiltrate source 1412. Resistors 1422a-1422m represent the predetermined hydraulic resistance of the corresponding diafiltration flow passages 1414 coupled in a series network and are used to control the flow rate of a diafiltrate stream to each stage 1402. The diafiltration flow passages 1420 fluidly couple the diafiltrate source 1412 to the corresponding feed input 1406 of each stage receiving diafiltrate. The diafiltration distributor 1416' is similar to the series diafiltration distributor 1309 of FIG. 13A. A benefit of the series configuration is the ease of integration in some embodiments of SPF modules and systems. One benefit of the parallel configuration is that any partial blockage of a channel has less impact on the performance of the entire distributor, and the parallel configuration facilitates the use of higher diafiltrate source pressures to reduce the sensitivity of the performance of the distributor to variations in feed pressures to the stages.

Now referring to FIG. 14C, an exemplary module 1400" includes at least one diafiltration distributor 1416" having a plurality of diafiltration flow passages 1420a'-1420m' which are fluidly coupled (sometimes through the corresponding resistor) to the pressurized diafiltrate source 1412. Resistors 1422a'-1422m' and 1410a'-1410m' represent the predetermined hydraulic resistance of the corresponding diafiltration flow passages 1414 coupled in a series-parallel network and are used to control the flow rate of each diafiltrate stream. The diafiltration flow passages 1414 and 1420' fluidly couple the diafiltrate source 1412 to the corresponding feed inputs 1406 to each stage. One method of implementing the diafiltration distributor in an externally staged system is to use tubing with the hydraulic resistance being provided by the length and diameter of each tubing section. The series-parallel configuration combines some of the features of the series and parallel configurations at the cost of some additional complexity.

Referring to FIG. 15, a counter current diafiltration module 1500 according to the invention includes components having hydraulic properties shown as a resistive network. The module 1500 includes a plurality of stages 1502a-1502n each having a retentate output 1504, a feed input 1506 and a permeate output 1508. The module 1500 further includes at least one diafiltration distributor 1516 similar to the diafiltration distributor 1416 of FIG. 14A and a pressurized diafiltrate source 1512. The module 1500 further includes at least one counter current diafiltration distributor 1522 and a pump 1520 fluidly coupled to a one or more permeate outputs 1508 supplying the permeate as a diafiltrate source. Resistors 1510a-1510b represent the predetermined hydraulic resistance of the corresponding counter current diafiltration flow passages 1514a-1514b coupled in a parallel network and are used to control the flow rate of the counter current diafiltrate stream to each stage. The pump 1520 is used to raise the pressure of the permeate from one or more stages 1502, here stages 1502*d* and 1502*n*, to be supplied as the diafiltrate to one or more preceding stages, here stages 1502*b* and 1502*c*. The counter current diafiltration distributor 1522 provides diafiltrate from following stages to channels in preceding stages. In one embodiment, diafiltrate is optionally added to the first stage 1502*a* (not shown).

Figure 16A:
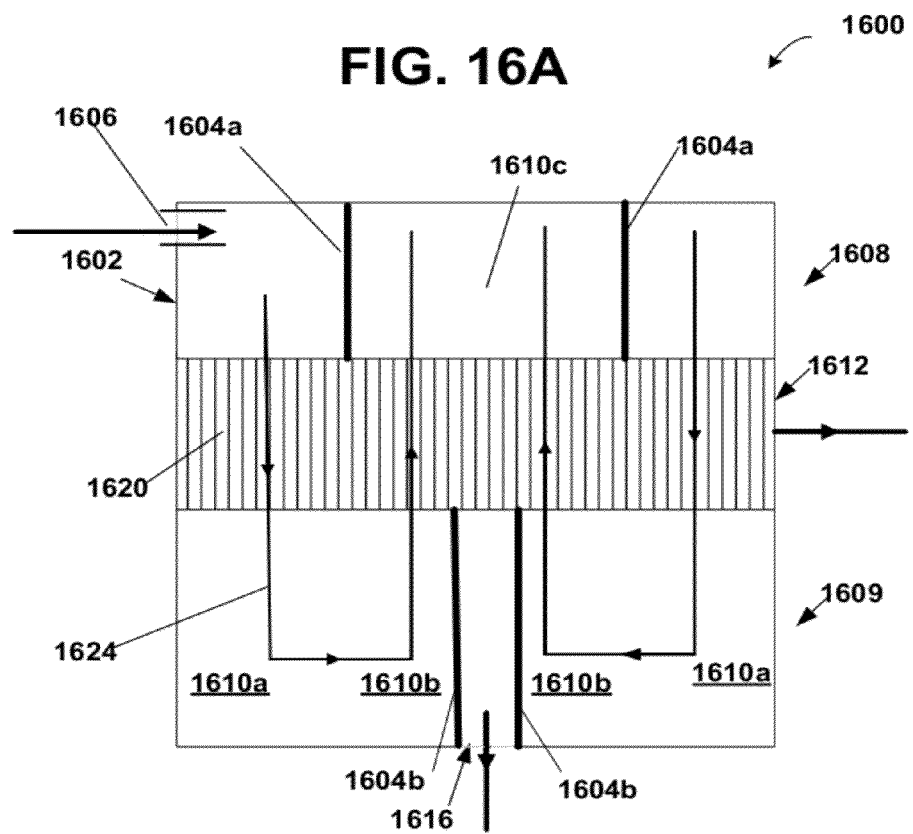
FIG. 16A is a schematic diagram of internally staged hollow fiber module according to the invention.

Referring to FIG. 16A an internally staged hollow fiber module 1600 includes a plurality of annular stages 1610*a*-1610*c* (collectively referred to as stages 1610) disposed within a cylindrical housing 1602, also referred to as a hollow fiber cartridge, having an upper end cap 1608 and lower end cap 1609. Each stage 1610 includes a plurality of channels, here hollow fiber membranes 1620 (also referred to as hollow fibers 1620), and the number of hollow fiber membranes 1620 can be the same in each stage 1610 or can be different as shown in FIG. 16A. In one embodiment the hollow fibers 1620 are disposed in an annular ring around an axis of the module 1600 forming a cylinder as shown in more detail in conjunction with FIG. 16B. The module 1600 further includes a plurality of cylindrical flow diverters 1604*a*-1604*b* (collectively referred to as cylindrical flow diverter 1604) disposed within the upper and lower end caps 1608, 1609, substantially parallel to the hollow fiber membranes 1620 and segregating the hollow fiber membranes 1620 so as to form the stages 1610, an inlet port 1606 disposed in the housing, a retentate port 1616 disposed in the housing and a permeate port 1612 disposed in the housing. In one embodiment, flow diverters 1604 form a fluid seal with a tube sheet (not shown) attached to the hollow fiber membranes 1620 within the upper and lower end caps 1608, 1609. In another embodiment, each of the channels, here the hollow fiber membranes 1620, has a dimensionless length, $\lambda_{stage}$, lower than about 6,000 a specific membrane area greater than about 50 cm$^{-1}$, and a dimensionless length, $\lambda_{system}$, for the module of at least about 2,000.

In operation, the hollow fiber membranes 1620 are arranged as a cylinder, and in the embodiment of FIG. 16A are divided into four stages 1610 by the cylindrical flow diverters 1604. A feed enters the outermost stage 1610*a* through the inlet port 1606, and flows through the lumens of the hollow fiber membranes 1620 as shown by flow path 1624. The feed stream enters a bottom section of stage 1610*a*, and then is directed in upward flow by the cylindrical flow diverters 1604*a*, into the second, middle, stage 1610*b*. On leaving the middle stage 1610*b*, in the upper section of the module 1600, the flow is diverted downward through the inner most, cylindrical, stage, 1610*n*. The retentate is directed out of the module 1600 through retentate port 1616. The permeate from the three stages 1610 exits the module 1600 through the permeate port 1612. The hollow fiber membranes 1620 are coupled together and the module 1600 includes seals (not shown) using hollow fiber encapsulation techniques known in the art to separate and fluidly couple the stages 1610.

Figure 16B:
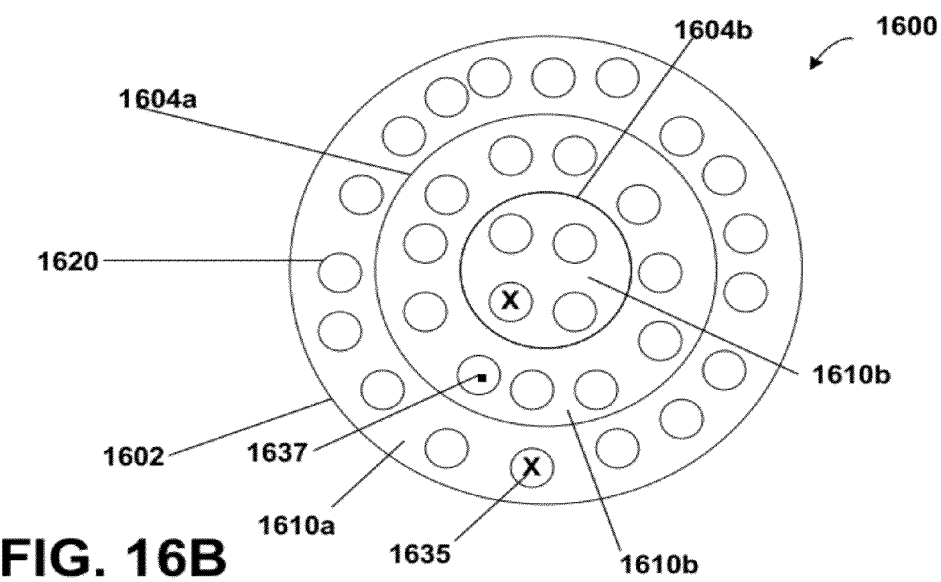
FIG. 16B is a schematic cross section diagram of the internally staged hollow fiber module of FIG. 16A.

Referring to FIG. 16B, in which like elements are provided having like reference designations as in FIG. 16A, the internally staged hollow fiber module 1600 shown in cross section along the axes of the hollow fiber membranes 1620 includes the cylindrical flow diverters 1604 dividing the hollow fiber membranes 1620 into stages 1610. The "X" 1635 indicates a flow directed into the page and the dot 1637 indicates flow out of the page illustrating that the flow in the hollow fiber membranes 1620 alternates direction in adjacent stages 1610. The module 1600 can be manufactured using techniques known in the art including end caps and tube sheets and other arrangements described in conjunction with FIG. 18A. Other embodiments of internally staged modules, comprising hollow fiber membranes in which the feed and retentate flow though the lumen of the hollow fibers, can be configured in various topologies. For example, the individual stages can be arranged in the form of cylindrical discs, within a cylindrical housing. The feed and retentate flows are in the axial direction from one stage to the next stage. It is also possible to arrange the individual stages in the form of sectors within a cylindrical housing. A feed stream enters a first sector and the retentate from the module leaves from the last sector. Such a device includes suitable passageways to conduct the retentate from one sector to the feed port of the next sector.

Figure 17:
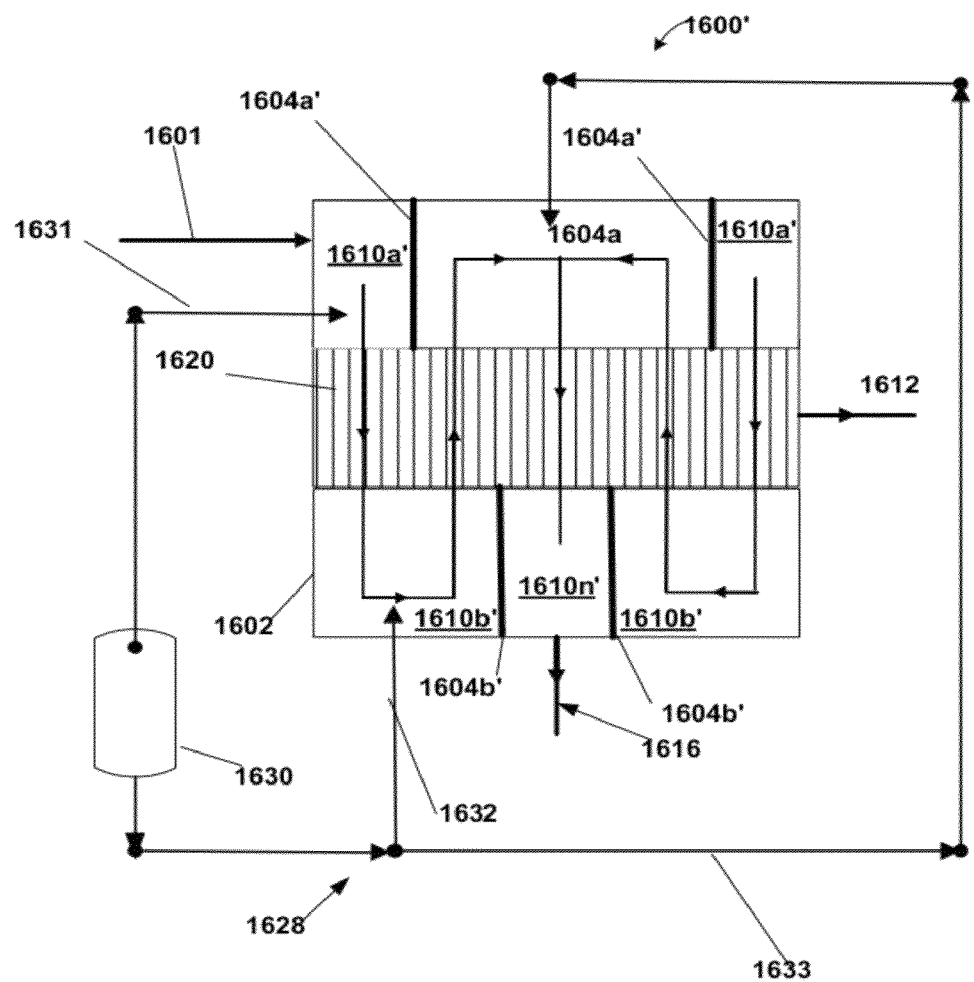
FIG. 17 is a schematic cross section diagram of an internally staged hollow fiber module suitable for diafiltration according to the invention.

Referring to FIG. 17, in which like elements are provided having like reference designations as in FIG. 16A, a hollow fiber module 1600' similar to module 1600 in FIG. 16A with the addition of at least one diafiltration distributor 1628 fluidly coupled to a pressurized source of diafiltrate 1630. The diafiltration distributor 1628 includes diafiltration flow passages 1631 and 1632. In one embodiment the stages 1610*a*'-1610*n*' (collectively referred to as stages 1610') are substantially identical having the approximately the same number of hollow fiber membranes 1620 unlike the stages 1610 in FIG. 16A. The module 1600' includes a plurality of cylindrical flow diverters 1604*a*'-1604*b*' (collectively referred to as cylindrical flow diverter 1604') disposed within the housing substantially parallel to the hollow fiber membranes 1620 and segregating the hollow fiber membranes 1620 so as to form the stages 1610'.

In operation, the diafiltration distributor 1628 is connected to the inlet of the stages 1610'. The diafiltrate to the first stage 1610*a*' flows through diafiltration flow passage 1631, to the second stage 1610*b*' through diafiltration flow passages 1632 and to the third stage 1610*n*' through diafiltration flow passages 1633. It will be appreciated that alternative embodiments could supply diafiltrate to less than all the stages 1610'. In one embodiment, diafiltration flow passage 1631 has predetermined hydraulic resistances to provide an approximately equal amount of diafiltrate to compensate for stage pressures variations.

Figure 18A:
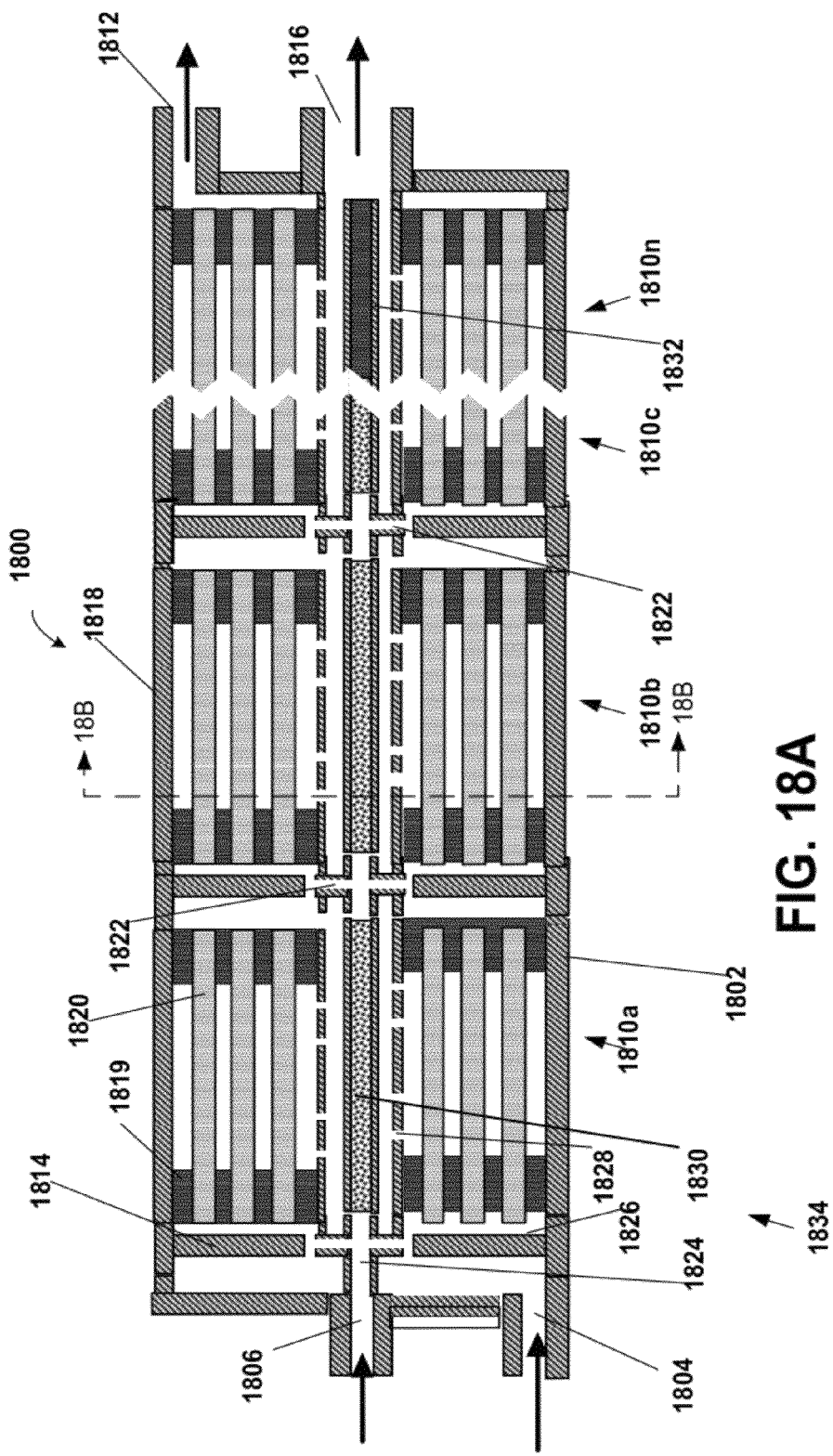
FIG. 18A is a longitudinal cross section view of an internally staged hollow fiber module suitable for diafiltration according to the invention.
Figure 18B:
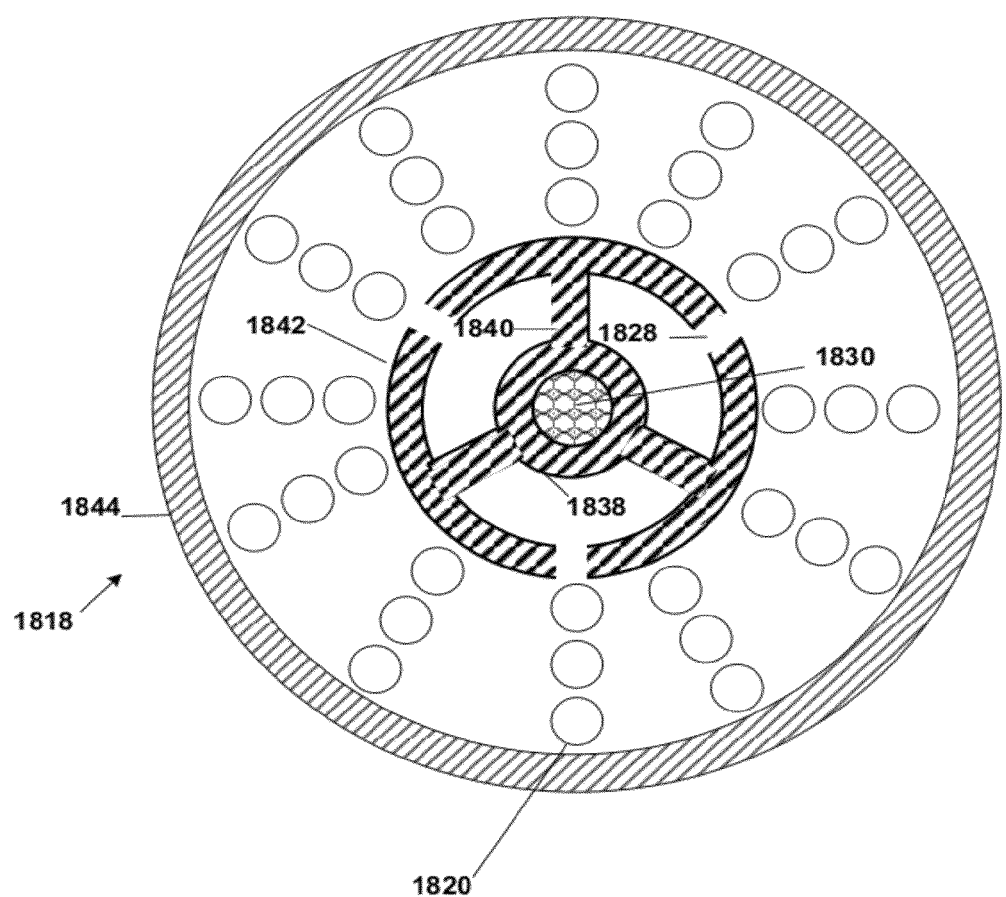
FIG. 18B is an axial cross section view of the internally staged hollow fiber module of FIG. 18A through line 18B.

Now referring to FIG. 18A, an alternative internally staged hollow fiber module 1800 suitable for diafiltration according to the invention includes a plurality stages 1810*a*-1810*n* (collectively referred to as stages 1810) disposed within a cylindrical housing 1802. Each stage 1810 includes a plurality of hollow fiber membranes 1820, and the number of hollow fiber membranes 1820, here, are the same in each stage 1810. In one embodiment the hollow fiber membranes 1820 are disposed in an annular ring (shown more clearly in FIG. 18B) forming a cylinder. The hollow fiber membranes 1820 are joined and segregated in one embodiment by a tube sheet 1819 formed using potting compounds as is known in the art so as to form the stages 1810. The module 1800 further includes a feed port 1804 disposed in the housing 1802, a retentate port 1812 disposed in the housing 1802, permeate perforations 1828 and a permeate port 1816 disposed in the housing 1802. The permeate perforations 1828 are disposed to direct the permeate to the permeate port 1816. In one embodiment, each of the stages 1810, here comprising the hollow fiber membranes 1820, has a dimensionless length, $\lambda_{stage}$, less than about 6,000, hollow fibers with specific membrane areas greater than about 50 cm$^{-1}$, and a dimensionless length of the module 1800, $\lambda_{system}$, greater than about 2,000.

The module 1800 further includes further includes a diafiltration distributor 1834 which comprises a diafiltration flow passage 1824 and a diafiltrate inlet port 1806 fluidly coupled to the diafiltration flow passage 1824. The diafiltration distributor 1834 further comprises a plurality of diafiltration passageways 1822 fluidly coupling the diafiltration flow passage 1824 to the corresponding stages 1810. The diafiltration flow passage 1824 includes a plurality of hydraulic resistors 1830 providing predetermined hydraulic resistances so as to introduce diafiltrate at a predetermined flow rate at a selected pressure into corresponding stages 1810. Now referring to FIG. 18B, in which like elements are provided having like reference designations as in FIG. 18A, the internally staged hollow fiber module 1800 further includes an annular center core 1838 comprising a plurality of radial supports 1840 coupled to an inner annular support ring 1842 around which the hollow fibers 1820 are disposed. The center core 1838 and the support ring 1842 extend axially along the module 1800. The perforations 1828 are disposed in the inner annular support ring 1842. The housing 1818 further comprises an outer shell 1844, and the hollow fibers 1820 are disposed between the outer shell 1844 and the inner annular support ring 1842. In one embodiment, the hydraulic resistors 1830 comprise a porous plug, and the housing 1818, supports 1840, the outer shell 1844 and the inner annular support ring 1842 are formed by an extrusion process as is known in the art.

In operation, diafiltrate is added via the diafiltration flow passages 1824 of the diafiltration distributor 1834. The hydraulic resistors 1830 provide the predetermined hydraulic resistance of the corresponding diafiltration flow passage 1824 similar to the SPF operation of the module 1318 of FIG. 13B. The diafiltration flow is terminated by plug 1832 in the last stage 1810n. The permeate is collected in the space between the hollow fibers 1820 and flows through the perforations 1828 to the permeate port 1816. The feed/retentate flows through the lumens of the hollow fibers 1820 in each stage 1810 after mixing with the diafiltrate and finally flows out the retentate port 1812.

Figure 19A:
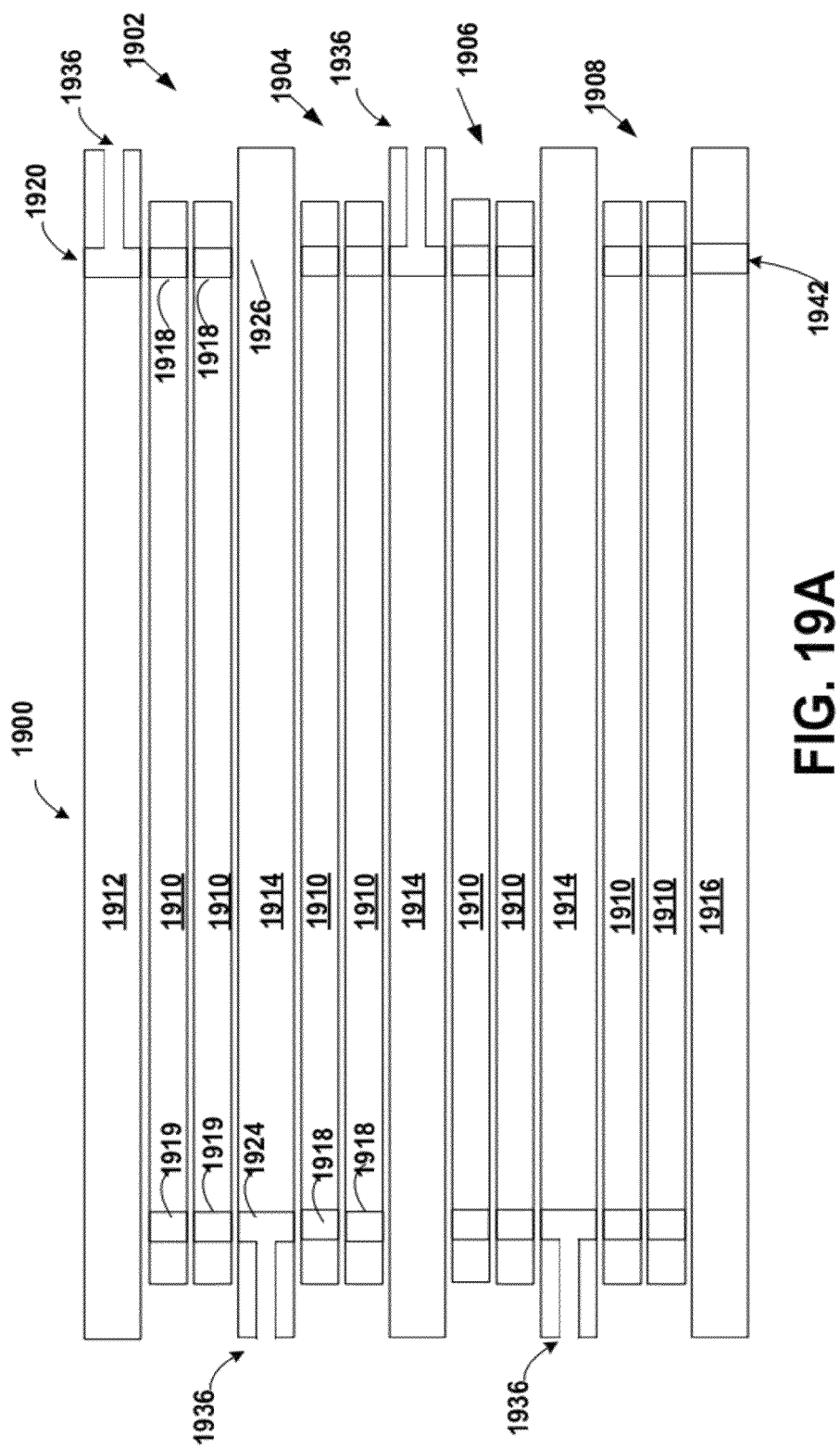
FIG. 19A is schematic diagram of an internally staged module including a staging plate suitable for cross current diafiltration according to the invention.

Referring to FIG. 19A, a single pass diafiltration system 1900 includes a plurality of stages 1902, 1904, 1906, and 1908 each stage having one or more cassettes 1910, a top plate 1912, a plurality of staging plates 1914 and a bottom plate 1916 in a stacked configuration. The cassettes 1910 each have at least one flow channel (not shown) fluidly coupled to a feed manifold 1918, a retentate manifold 1919 and at least one permeate channel (not shown). The top plate 1912 includes a feed port 1920 in fluid communication with a feed pump 1922 and a diafiltration distributor 1936 fluidly coupled to the feed inlet port 1920. The staging plate 1914 includes a pass through port 1924 disposed to align with corresponding feed manifolds 1918 and retentate manifolds 1919. The staging plate 1914 also includes a diafiltration distributor 1936 fluidly coupled to the pass through port 1924. The bottom plate 1916 includes a retentate port 1942 in fluid communication with the adjacent cassette 1910. The staging plates 1914 are disposed to serialize the retentate flow while leaving the permeate channels coupled in parallel. In one embodiment the cassettes 1910 are conventional cassettes similar to the cassettes used in system 1100 in FIG. 11A. Although conventional cassettes can be used, performance is enhanced by the use of cassettes with higher specific membrane areas.

In one embodiment, the system 1900 has a 2,2,2,2 configuration (i.e., a stack including the top plate 1912, two cassettes 1910, staging plate 1914, two cassettes 1910, staging plate 1914, two cassettes 1910, staging plate 1914, two cassettes 1910, and the bottom plate 1916). In this embodiment, the effect of staging is to enable diafiltration with flux and buffer consumption comparable to batch diafiltration.

In operation, the system 1900 runs as an SPF process similar to the process described in FIGS. 2, 11A and 13A. In each stage 1902, 1904 and 1906, for example stage 1902, the feed manifolds 1918 of each cassette 1910 are fluidly coupled in parallel however the staging plate 1914 blocks the feed stream at point 1926 from entering stage 1904 as would occur in a conventional plate and frame assembly thereby serializing the flow through the retentate manifolds 1919 and the pass through port 1924 in the staging plate 1914. Here the low specific feed flow rate is enabled by the serialization of the flow channels of the cassettes 1910. In addition, diafiltrate is added at each stage in a process similar to the process described above in conjunction with FIGS. 13A and 13B. Here however the diafiltrate is added through the feed port 1920 in the first stage 1902 and through the pass through port 1924 in the other stages 1904, 1906 and 1908. Diafiltrate is optionally added to the first stage 1902.

Figure 19B:
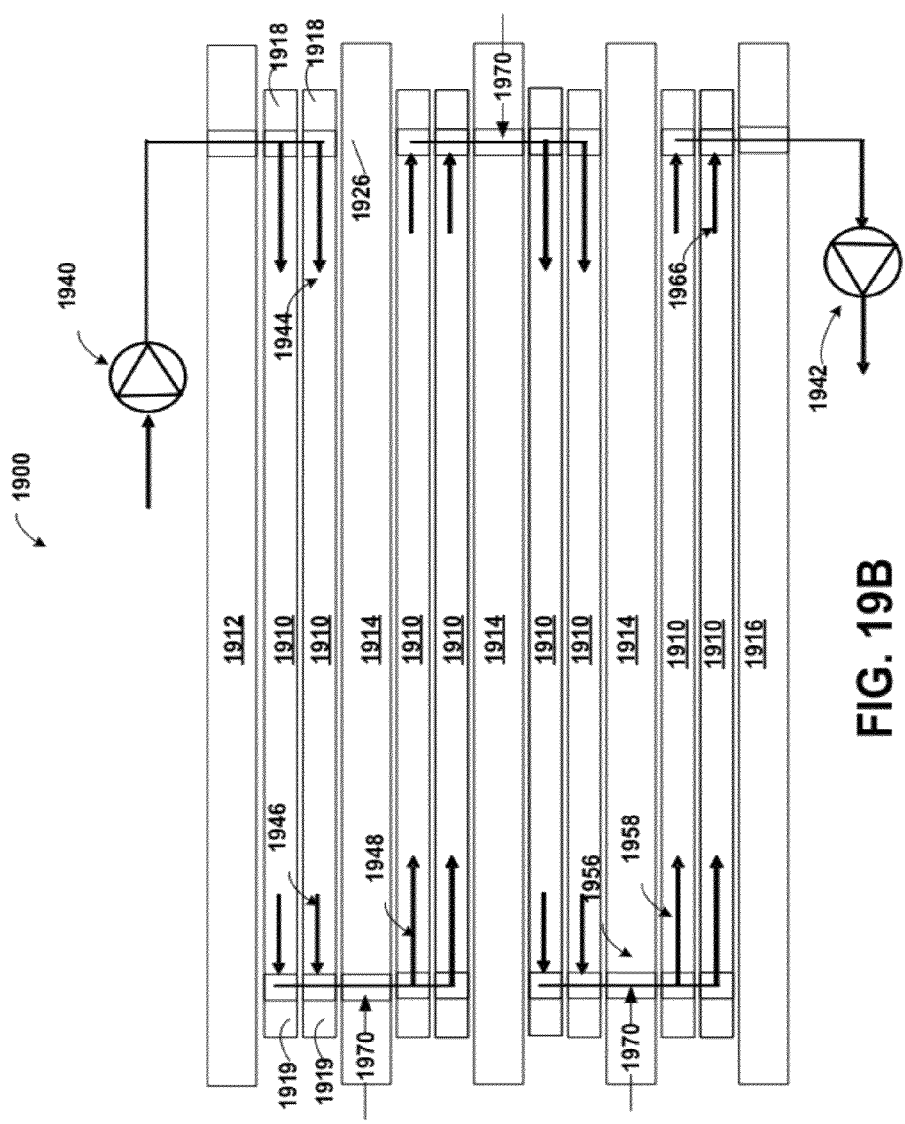
FIG. 19B is a flow diagram showing the feed stream in the four-stage module of FIG. 19A.

Referring to FIG. 19B, in which like elements are provided having like reference designations as in FIG. 19A, the flow paths through system 1900 are shown. The feed stream flows through and enters the feed port 1920 of the top plate 1912. The feed stream then flows in parallel into the feed manifold 1918 of each cassette 1910. The feed stream then flows across the channel as indicated by flow arrow 1944 and flows into the retentate manifold 1919 of each cassette 1910 as indicated by flow arrow 1946. The retentate of stage one then flows through the pass through port 1924 of the staging plate 1914 into the cassettes 1910 of stage two as indicated by flow arrow 1948. The diafiltrate is added into the pass through port 1924 of distributor 1936 as indicated by flow arrow 1970. Note that at section 1926 of the staging plate 1914 the feed manifold of the first stage 1906 is blocked. The flow continues in a similar manner until the flow reaches the bottom plate 1916 and the retentate exits through the retentate port 1942 as indicated by flow arrow 1966. It is understood that the system 1900 can include fewer or more than four stages and that diafiltrate can be added at some or all the stages.

Now Referring to FIG. 20, a staged counter current diafiltration module 2000 according to the invention includes a plurality of stages 2010a-2010n (collectively referred to as stages 2010) each of the stages 2010 having a plurality of channels 2004 and a plurality of permeate compartments 2014 fluidly coupled to permeate distributor 2002a and 2002b (collectively referred to as permeate distributors 2002). Permeate distributor 2002b is fluidly coupled to a pressure source 2012 which is fluidly coupled to a feed manifold 2006a. Diafiltration passageways connecting the pressure source 2012 to the feed manifold 2006a are arranged to insure good mixing.

In operation, the permeate distributor 2002b provides diafiltrate from stage 2010b to the preceding stage 2010a. In other embodiments, the counter current diafiltration module can include more than one permeate distributor 2002, and the permeate distributor can combine the output from one or more permeate compartments 2014. Furthermore, each permeate distributor 2002 can supply diafiltrate to one or more stages 2010. A pressure source, for example, a pump, is provided for each permeate distributor 2002 and corresponding counter current diafiltration network.

Figure 21:
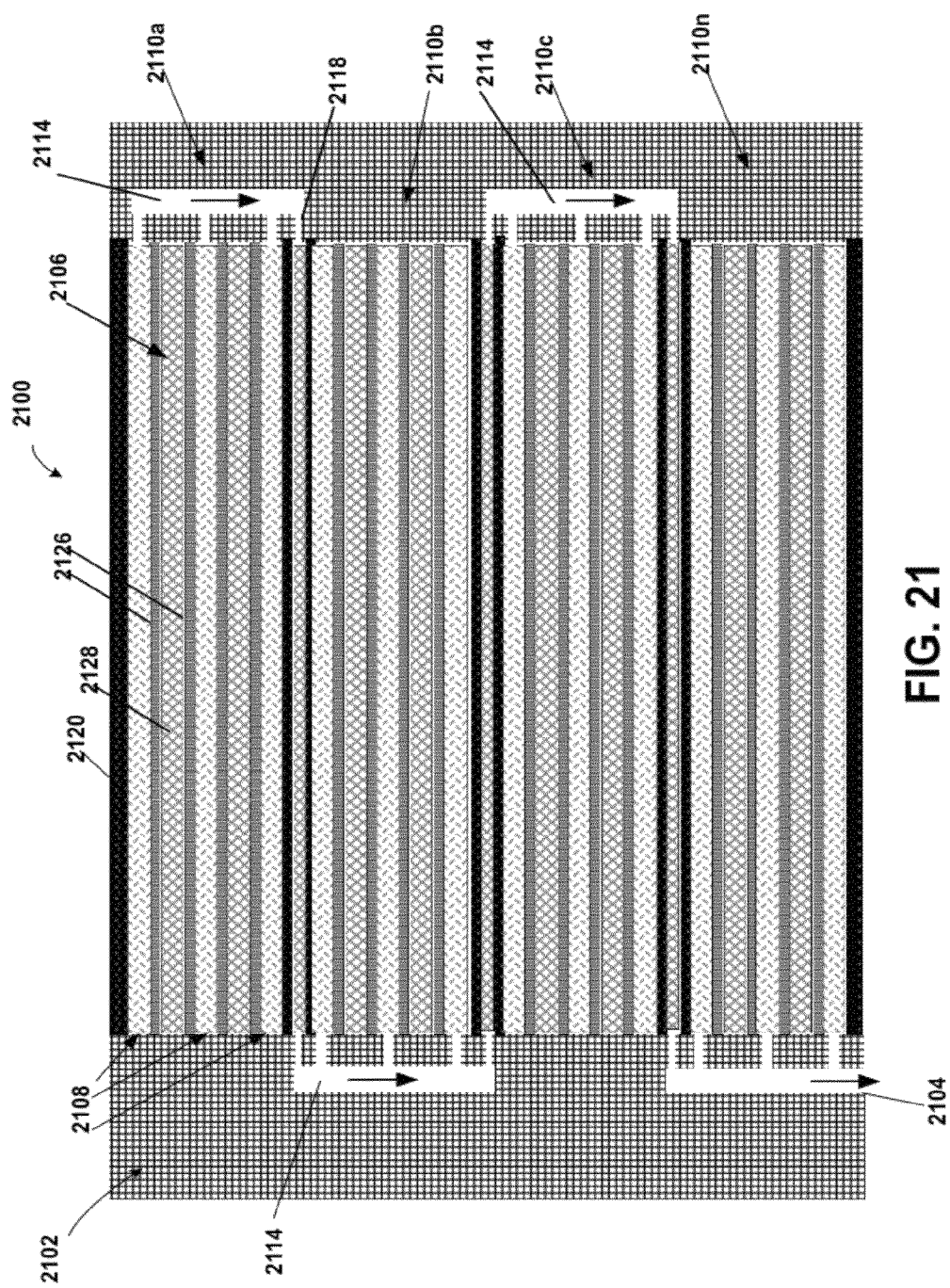
FIG. 21 is a schematic diagram of permeate distributor according to the invention.

Referring now to FIG. 21, an internally staged SPF system 2100 with permeate control according to the invention, includes a plurality of stages 2110a-2110n (collectively referred to as stages 2110) each of the stages 2110 having a plurality of channels 2106 and a plurality of permeate compartments 2108 fluidly coupled to a permeate distributor 2102. Each channel 2106 comprises a membrane 2126 disposed adjacent to a feed spacer 2128 which provides support for the membrane 2126. In one embodiment, the channels 2106 have $\sigma_c$ values of greater than about 40 cm$^{-1}$ and the stages 2110 have $\lambda_{stage}$ values of less than about 6,000. In this embodiment, the $\lambda_{system}$ for system 2100 is greater than 2,000. The permeate distributor 2102 includes a plurality of permeate manifolds 2114 fluidly coupled to the plurality of permeate compartments 2108 through a plurality of permeate flow passages 2118. The permeate distributor 2102 further includes a permeate outlet port 2104 coupled to the permeate manifold 2114 of the last stage 2110*n*. The permeate distributor 2102 further includes a permeate collector (not shown) fluidly coupled to the permeate outlet port 2104. The permeate distributor 2102 provides a network of hydraulic resistors analogous to the diafiltration distributor networks of modules 1400 and 1400' described in conjunction with FIGS. 14A and 14B.

The stages 2110 are disposed such that each stage is in fluid communication with each adjacent stage preceding it and is in fluid communication with each adjacent stage that follows it (i.e. the retentate from the $i^{th}$ stage feeds the feed of the $(i+1)^{th}$ stage). Each of the channels 2106 includes a filtration membrane. As described above, each of the channels 2106 has a length, a membrane area, a void volume, a specific membrane area expressed as a ratio of the membrane area to the void volume, and a dimensionless length expressed as a product of the channel length and the specific membrane area.

In operation, the predetermined hydraulic resistances of the flow passages 2118 of the permeate distributor 2102 provides a pressure in the permeate compartments 2108 of each stage thereby providing a target TMP in the channels 2106 of each stage 2110, which in turn provides a predetermined permeation rate in each stage 2110. In one embodiment, it is desirable to maintain the same TMP in the channels 2106 of each stage 2110 in spite of the fact that the feed pressure in each stage 2110 decreases along the flow path. In this manner the TMP along the whole flow path remains approximately constant in spite of the long flow path. In another embodiment, the predetermined permeation rate decreases monotonically from the first to the last stage. While the feed pressure, and therefore the TMP naturally decreases along the flow path, the permeate distributor 2102 enables the control of the TMP in a predetermined manner independently of the pressure drop occurring in the channels 2106. Controlling the TMP in the upstream stages to values lower than what would be obtained without a permeate distributor prevents the over concentration of solute and thereby a more effective separation process. In still another embodiment, high inlet feed pressures are used while controlling the TMP below a desired value by means of the permeate distributor 2102; in this manner very long channels 2106 are used without incurring in excessive TMP anywhere in the flow path.

In general, TMP control by means of the permeate distributor 2102 provides an additional degree of freedom in the design of SPF modules and processes to meet the needs of differing applications, for example, different concentrations and viscosities. Advantages in operating in SPF mode with TMP control by means of permeate distributors includes but is not limited to a reduction in membrane fouling, a reduction in damage of sensitive molecules, maintaining the selectivity of the membrane separation process, and avoidance of rapid deterioration of the module. In one embodiment the conversion is set to a predetermined value by controlling the ratio of the feed stream flow rate to the permeate stream flow rate. In another embodiment the conversion is set to a predetermined value by controlling the ratio of the feed stream flow rate to the retentate stream flow rate. In yet another embodiment the TMP in each stage is controlled independently of the feed pressures in the stages 2110 by using the permeate distributor 2102 to control the permeate flow in the stages 2110.

In general, the practice of SPF uses modules made with long and thin channels. The length can be characterized by the dimensionless length, $\lambda$, while the thickness of the channels can be characterized by the specific membrane area of the channel, $\sigma_c$. Mathematical modeling of SPF processes utilizing staged modules show that the flux of an SPF module increases with increasing $\sigma_c$, thereby allowing the use of a correspondingly smaller dimensionless channel length, $\lambda$, for a fixed conversion. This means that some SPF embodiments with sufficiently large $\sigma_c$ may operate with values of $\lambda$ lower than about 2,000. In general, the minimum value of $\lambda$ used to meet the desired conversion shows the following dependence on the value of $\sigma_c$:

$$\lambda_{MIN} \approx \frac{B}{\sigma_C^n}; \tag{12}$$

where the values of the parameters n and B depend on the properties of the solution and the desired conversion, as well as on the type of channel. More specifically, the value of the parameter B varies with the desired conversion, the higher the desired conversion the higher the value of B.

For one example of a SPF process for concentrating BSA, utilizing staged SPF cassettes having existing feed spacers, starting with BSA concentrations of 5-10 g/L, and for desired conversions exceeding 80%, the values of the parameters n and B are estimated to be about 0.57 and about 30,000, respectively, to yield the following operational formula derived from equation 12 as follows:

$$\lambda > \lambda_{MIN} = \frac{30{,}000}{\sigma_C^{0.57}}; \tag{13}$$

where the value of $\sigma_c$ is expressed in units of $cm^{-1}$. Table 4 shows the relationship between $\sigma_c$ and $\lambda$, that results from equation 13, demonstrating that some modules having channels with a value of $\sigma_c$ exceeding about 126 $cm^{-1}$ may use channels having dimensionless lengths lower than about 2000. The third column in Table 4 shows the value of a minimum channel length, $L_{MIN}$, which decreases even faster than $\lambda_{MIN}$, demonstrating that SPF modules with channel lengths similar to those of existing cassettes (about 18 cm) could be used to effect high conversion processes if such modules are made with channels having a value of $\sigma_c$ exceeding about 126 $cm^{-1}$.

TABLE 4

| σC [$cm^{-1}$] | λ [ ] | $L_{MIN}$ Length cm |
|---|---|---|
| 40 | 3,802 | 95 |
| 50 | 3,355 | 67 |
| 80 | 2,579 | 32 |
| 100 | 2,276 | 23 |
| 126 | 2,000 | 16 |
| 300 | 1,230 | 4 |

Utilizing similar mathematical models, similar relationships can be derived for other applications and channel types. It is believed that for one set of applications, in which the target product is a protein similar to BSA, the value of n ranges from about 0.3 to about 1 and that of B ranges from approximately about 10,000 to about 1,000,000. There is no particular limit to how high $\sigma_c$ can be, aside from possible plugging problems associated with very small channel dimensions. If the fluids being treated are substantially free of particulate matter, $\sigma_c$ can be very large and $\lambda$ can be correspondingly lower.

It is understood that although the embodiments described herein relate specifically to separations of interest in biomolecular applications, the principles, practice and designs described herein are also useful in other applications. All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way. While the present invention has been described in conjunction with various embodiments and examples, it is not intended that the present teachings be limited to such embodiments or examples. On the contrary, the present invention encompasses various alternatives, modifications, and equivalents, as will be appreciated by those of skill in the art. While the teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto are claimed. The descriptions and diagrams of the methods of the present teachings should not be read as limited to the described order of elements unless stated to that effect.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. A single-pass tangential-flow filtration system comprising:
    a plurality of substantially identical stages, each stage having a plurality of channels;
    each of the channels has a length, a membrane area, a void volume, a specific membrane area $\sigma_C$ expressed as a ratio of the membrane area to the void volume, and a dimensionless length $\lambda$ expressed as a product of the channel length and the specific membrane area; and
    a dimensionless length of the system is greater than about 2,000;
    a dimensionless length of at least one of the plurality of substantially identical stages is less than about 6,000 to provide relatively short flow paths for individual stages; and
    wherein each of the substantially identical stages comprises a cassette.

2. The filtration system of claim 1, wherein each of the substantially identical stages includes a series-parallel arrangement of channels.

3. The filtration system of claim 1, wherein a specific membrane area of a channel in one of a plurality of substantially identical stages, is greater than about 40 cm$^{-1}$.

4. The filtration system of claim 1, wherein the dimensionless length of the system is greater than about 4,000 and the dimensionless length of the at least one of the plurality of stages is less than about 3,500.

5. The system of claim 1, wherein at least one cassette in a first stage comprises a feed manifold, a retentate manifold, at least one permeate channel, and at least one flow channel fluidly coupled to the feed manifold;
    wherein at least one cassette in a second stage comprises a feed manifold and a retentate manifold;
    further comprising a staging plate disposed between the at least one cassette in a first stage and the at least one cassette in a second stage; and
    wherein the staging plate fluidly couples the retentate manifold of the at least one cassette in a first stage to the feed manifold of the at least one cassette in a second stage and blocks flow from the feed manifold of the at least one cassette in a first stage, thereby serializing retentate flow through the system.

6. The system of claim 5, wherein the staging plate comprises a feed blocking plate separating the at least one cassette in a first stage and the at least one cassette in a second stage and which couples a retentate manifold of the at least one cassette in a first stage to a corresponding feed manifold of the at least one cassette in a second stage and blocks a flow from the feed manifold of the at least one cassette in a first stage.

7. The system of claim 6 wherein the feed blocking plate further comprises at least one pass through port aligned with the corresponding retentate manifold of the at least one cassette in a first stage and the corresponding feed manifold of the at least one cassette in a second stage.

8. The filtration system of claim 1, wherein the dimensionless length of each stage is substantially equal to the dimensionless length of the longest serial flow path of each stage.

9. A single-pass tangential-flow filtration system comprising:
    a plurality of substantially identical stages, each stage having a plurality of channels;
    each of the channels has a length, a membrane area, a void volume, a specific membrane area $\sigma_C$ expressed as a ratio of the membrane area to the void volume, and a dimensionless length $\lambda$ expressed as a product of the channel length and the specific membrane area; and
    a dimensionless length of the system is greater than about 2,000;
    a dimensionless length of at least one of the plurality of substantially identical stages is less than about 6,000 to provide relatively short flow paths for individual stages;
    wherein the dimensionless length of each of the plurality of substantially identical stages is substantially identical; and
    wherein a specific membrane area of a channel in one of a plurality of substantially identical stages, is greater than about 40 cm$^{-1}$.

10. The filtration system of claim 9, wherein each of the substantially identical stages includes a series-parallel arrangement of channels.

11. The filtration system of claim 9, wherein each of the substantially identical stages comprises a cassette.

12. The filtration system of claim 9, wherein the dimensionless length of the system is greater than about 4,000 and the dimensionless length of the at least one of the plurality of stages is less than about 3,500.

* * * * *